United States Patent [19]
Rochus et al.

[11] Patent Number: 6,110,920
[45] Date of Patent: Aug. 29, 2000

[54] THIENOPYRIMIDINES

[75] Inventors: Jonas Rochus, Darmstadt; Pierre Schelling, Mühltal; Franz-Werner Kluxen, Darmstadt; Maria Christadler, Rödermark, all of Germany

[73] Assignee: Merck Patent Gesellschaft mit beschrankter Haftung, Germany

[21] Appl. No.: 09/230,806

[22] PCT Filed: Jul. 30, 1997

[86] PCT No.: PCT/EP97/04139

§ 371 Date: Feb. 9, 1999

§ 102(e) Date: Feb. 9, 1999

[87] PCT Pub. No.: WO89/06722

PCT Pub. Date: Feb. 19, 1998

[30] Foreign Application Priority Data

Aug. 12, 1996 [DE] Germany .................. 196 32 423

[51] Int. Cl.⁷ ...................... A61K 31/519; C07D 495/04
[52] U.S. Cl. .................. 514/258; 514/267; 544/278; 544/250
[58] Field of Search .................. 544/278, 250; 514/258, 267

[56] References Cited

U.S. PATENT DOCUMENTS 4,146,716  3/1979  Cox et al. .................. 544/278
4,196,207  4/1980  Webber .................. 424/251

FOREIGN PATENT DOCUMENTS 579496  1/1994  European Pat. Off. .
728759  8/1996  European Pat. Off. .

*Primary Examiner*—Richard L. Raymond
*Assistant Examiner*—Sudhaker B. Patel
*Attorney, Agent, or Firm*—Millen, White, Zelano & Branigan, P.C.

[57] ABSTRACT

Thienopyrimidines of the formula I

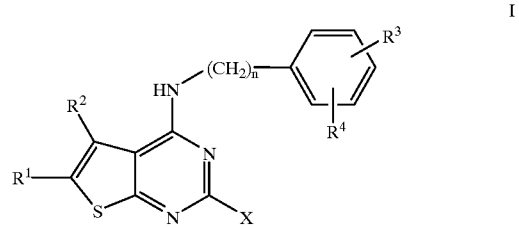

and the physiologically acceptable salts thereof in which $R^1, R^2, R^3, R^4$, X and n have the meanings given in Claim 1 inhibit phosphodiesterase V and can be employed for the treatment of diseases of the cardiovascular system and for the therapy of impaired potency.

19 Claims, No Drawings

THIENOPYRIMIDINES

This application is a 371 of PCT/EP97/04139, filed Jul. 30, 1997.

The invention relates to compounds of the formula I

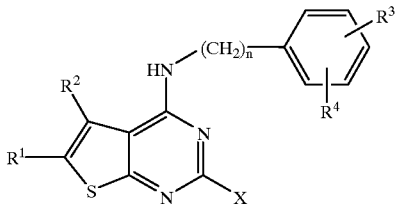

in which

R$^1$, R$^2$ in each case independently of one another are H, A, OA, alkenyl, alkinyl, NO$_2$, CF$_3$ or Hal, where one of the radicals R$^1$ or R$^2$ is always ≠H, R$^1$ and R$^2$ together are also alkylene having 3–5 C atoms, R$^3$, R$^4$ in each case independently of one another are H, A, OA, Hal, NO$_2$, NH$_2$, NHA or NAA', R$^3$ and R$^4$ together are also —O—CH$_2$—CH$_2$—, —O—CH$_2$—O or —O—CH$_2$—CH$_2$—O—, A, A' in each case independently of one another are alkyl having 1 to 6 C atoms, X is an unsaturated 5–7-membered heterocycle having 1–4 N, O and/or S atoms which is unsubstitued or mono-, di- or trisubstituted by A, Hal or CF$_3$ and in which additionally further CH$_2$ groups can be replaced by NH, NA, S or O bonded via N or C, Hal is F, Cl, Br or I and n is 0, 1, 2 or 3, and the physiologically acceptable salts thereof.

Pyrimidine derivatives are disclosed, for example, in EP 201 188 or in WO 93/06104.

The invention was based on the object of finding novel compounds which have valuable properties, in particular those which can be used for the preparation of pharmaceuticals.

It has been found that the compounds of the formula I and their salts have very valuable pharmacological properties combined with good tolerance.

In particular, they show specific inhibition of cGMP phosphodiesterase (PDE V).

Quinazolines which have cGMP phosphodiesterase-inhibitory activity are described, for example, in J. Med. Chem. 36, 3765 (1993) and ibid. 37, 2106 (1994).

The biological activity of the compounds of the formula I can be determined by methods as they are described, for example, in Wo 93/06104. The affinity of the compounds according to the invention for cGMP and cAMP phosphodiesterase is determined by determining their IC$_{50}$ values (concentration of inhibitor required for achieving a 50% inhibition of enzyme activity). To carry out the determinations, enzymes which have been isolated by customary methods may be used (for example W. J. Thompson et al., Biochem. 1971, 10, 311). To carry out the experiments, a modified batch method of W. J. Thompson and M. M. Appleman (Biochem. 1979, 18, 5228) may be used.

Thus, the compounds are suitable for treating diseases of the cardiovascular system, in particular cardiac insufficiency, and for the therapy of impaired potency.

The compounds of the formula I can be employed as pharmaceutically active ingredients in human and veterinary medicine. Furthermore, they can be employed as intermediates for the preparation of other pharmaceutically active ingredients.

Accordingly, the invention relates to the compounds of the formula I and to a process for the preparation a) of compounds of the formula I according to Claim 1 and salts thereof in which X is bonded via N, characterized in that a compound of the formula II

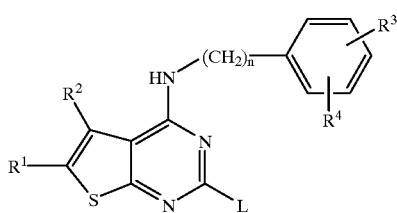

in which

R$^1$, R$^2$, R$^3$, R$^4$ and n have the abovementioned meanings and L is Cl, Br, OH, SCH$_3$ or a reactive esterified OH group is reacted with an unsaturated 5–7-membered heterocycle which has at least one NH group and which is unsubstituted or mono-, di- or trisubstituted by A, Hal or CF$_3$ and in which additionally further CH$_2$ groups can be replaced by NH, NA, S or O, or b) of compounds of the formula I according to Claim 1 and salts thereof in which X is bonded via C, characterized in that a compound of the formula III

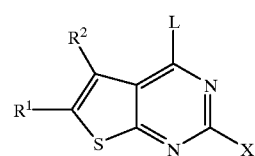

in which

R$^1$, R$^2$ and X have the abovementioned meanings, and L is Cl, Br, OH, SCH$_3$ or a reactive esterified OH group with a compound of the formula IV

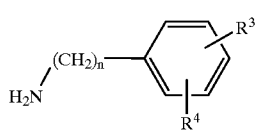

in which

R$^3$, R$^4$ and n have the abovementioned meanings, or c) in that, in a compound of the formula I, a radical R$^1$, R$^2$, R$^3$ and/or R$^4$ is converted into a different radical R$^1$, R$^2$, R$^3$ and/or R$^4$ by reducing a nitro group, by converting a primary or a secondary amino group into an alkylated amine by reductive amination or by acylating such an amino group, and/or in that a basic compound of the formula I is converted into a salt thereof by treatment with an acid.

The radicals R$^1$, R$^2$, R$^3$, R$^4$, X, L and n hereinabove and hereinbelow have the meanings given in formulae I, II, III, IV and V unless other details are given expressly.

A and A' are by preference in each case independently of one another alkyl having 1–6 C atoms.

In the above formulae, alkyl is preferably unbranched and has 1, 2, 3, 4, 5 or 6 C atoms, preferably 1, 2, 3, 4 or 5 C atoms, and is preferably methyl, ethyl or propyl, furthermore preferably isopropyl, butyl, isobutyl, sec-butyl or tert-butyl, but also n-pentyl, neopentyl or isopentyl.

Alkylene is by preference unbranched and is preferably propylene, butylene or pentylene.

Amongst the radicals $R^1$ and $R^2$, one is by preference H while the other is preferably propyl or butyl, but especially preferably ethyl or methyl. Furthermore, $R^1$ and $R^2$ together are also preferably propylene, butylene or pentylene.

Hal is by preference F, Cl or Br, but also I.

Alkenyl is by preference vinyl, 1- or 2-propenyl, 1-butenyl, isobutenyl, sec-butenyl, and is furthermore preferably 1-pentenyl, iso-pentenyl or 1-hexenyl.

Alkynyl is by preference ethynyl, propyn-1-yl, furthermore but-yn-1-yl, butyn-2-yl, pentin-1-yl, pentyn-2-yl or pentyn-3-yl.

The radicals $R^3$ and $R^4$ can be identical or different and are by preference in the 3- or 4-position of the phenyl ring. For example, they are in each case independently of one another H, alkyl, alkoxy, nitro, amino, alkylamino such as, for example, methylamino, dialkylamino such as, for example, dimethylamino, F, Cl, Br or I, or together are ethyleneoxy, methylene-dioxy or ethylenedioxy. They are also in each case preferably alkoxy such as, for example, methoxy, ethoxy or propoxy.

The radical X is by preference 2- or 3-furyl, 2- or 3-thienyl, 1-, 2- or 3-pyrrolyl, 1-, 2-, 4- or 5-imidazolyl, 2-methyl-1-imidazol-1-yl, 1-, 3-, 4- or 5-pyrazolyl, 2-, 4- or 5-oxazolyl, 3-, 4-, or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1- , -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl or pyrazinyl, each of which is unsubstituted or mono-, di- or trisubstituted by alkyl Hal, or $CF_3$.

The rule that all radicals which occur more than once can be identical or different, i.e. are independent of one another, applies to the entire invention.

Accordingly, the invention relates in particular to those compounds of the formula I in which at least one of the abovementioned radicals has one of the meanings given above as being preferred. Some preferred groups of compounds can be expressed by the following sub-formulae Ia to Ie, which correspond to the formula I and in which the radicals which are not described in greater detail have the meanings given for formula I, but in which

| | | |
|---|---|---|
| in Ia | X | is imidazolyl or pyridinyl; |
| in Ib | $R^1, R^2$ | in each case independently of one another are H, A, OA, $NO_2$, $CF_3$ or Hal, where at least one of the radicals $R^1$ or $R^2$ is always ≠ H, |
| | $R^3$ and $R^4$ | together are —O—$CH_2$—$CH_2$—, —O—$CH_2$—O— or —O—$CH_2$—$CH_2$—O, |
| | X | is imidazolyl or pyridinyl and |
| | n | is 1; |
| in Ic | $R^1, R^2$ | in each case independently of one another are H, A, OA, $NO_2$. $CF_3$ or Hal, where at least one of the radicals $R^1$ or $R^2$ is always ≠ H, |
| | $R^3, R^4$ | in each case independently of one another are H, A, OA, Hal, $NO_2$, $NH_2$, NHA or NAA', |
| | X | is imidazolyl or pyridinyl and |
| | n | is 1; |
| In Id | $R^1$ and $R^2$ | together are alkylene having 3–5 C atoms, |
| | $R^3$ and $R^4$ | together are —O—$CH_2$—$CH_2$—, —O—$CH_2$—O— or —O—$CH_2$—$CH_2$—O, |
| | X | is imidazolyl or pyridinyl and |
| | n | is 1; |
| in Ie | $R^1$ and $R^2$ | together are alkylene having 3–5 C atoms, |
| | $R^3, R^4$ | in each case independently of one another are H, A, OA, Hal, $NO_2$, $NH_2$, NHA or NAA', |
| | X | is imidazolyl or pyridinyl and |
| | n | is 1. |

Besides, the compounds of the formula I and also the starting materials for their preparation are prepared by methods known per se and they are described in the literature (for example in the standard publications such as Houben-Weyl, Methoden der organischen Chemie [Methods in Organic Chemistry], Georg-Thieme-Verlag, Stuttgart), under reaction conditions which are known and suitable for the abovementioned reactions. It is also possible to make use of variants which are known per se and not mentioned in greater detail in the present text.

In the compounds of the formulae II, III and IV, $R^1$, $R^2$, $R^3$, $R^4$, X and n have the abovementioned meanings, in particular the abovementioned preferred meanings.

If L is a reactive esterified OH group, then this is by preference alkylsulfonyloxy having 1–6 C atoms (preferably methylsulfonyloxy) or arylsulfonyloxy having 6–10 C atoms (preferably phenyl- or p-tolyl-sulfonyloxy, furthermore also 2-naphthalenesulfonyloxy).

If desired, the starting materials may also be formed in situ, so that they are not isolated from the reaction mixture but immediately reacted further to give the compounds of the formula I. On the other hand, it is possible to carry out the reaction stepwise.

The compounds of the formula I in which X is bonded to the thienopyrimidine ring system via N can be obtained by preference by reacting compounds of the formula II with an unsaturated 5–7-membered heterocycle which has at least one NH group and which is unsubstituted or mono-, di- or trisubstituted by A, Hal or $CF_3$ and in which additionally further $CH_2$ groups can be replaced by NH, NA, S or O.

Some of the starting materials of the formula II are known. If they are not known, they can be prepared by methods known per se.

Precursors of the compounds of the formula II can be prepared for example by cyclization and halogenation analogously to the procedure described in J. Med. Chem. 24, 374 (1981). Subsequent reaction with arylalkylamines gives the compounds of the formula II.

In detail, the reaction of the compounds of the formula II with the NH-containing heterocycle is carried out in the presence or absence of an inert solvent at temperatures between approximately −20 and approximately 150°, preferably between 20 and 100°.

Addition of an acid-binding agent, for example an alkali metal hydroxide, alkali metal carbonate, alkali metal bicarbonate, alkaline earth metal hydroxide, alkaline earth metal carbonate or alkaline earth metal bicarbonate, or of another salt of a weak acid of the alkali metal or alkaline earth metals, preferably of potassium, sodium or calcium, or an addition of an organic base such as triethylamine, dimethylamine or pyridine or quinoline or of an excess of the amine component may be advantageous.

Examples of suitable inert solvents are hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl ether, ethylene glycol monoethyl ether (methylglycol or ethylglycol) or ethylene glycol dimethyl ether (diglyme); ketones such as acetone or butanone; amides such as acetamide, dimethylacetamide or dimethyl-formamide (DMF); nitriles such as acetonitrile; sulfoxides such as dimethyl sulfoxide (DMSO); nitro compounds such as nitromethane or nitrobenzene; esters such as ethyl acetate, or mixtures of the abovementioned solvents.

Compounds of the formula I in which X is bonded to the thienopyrimidine ring system via C can furthermore be obtained by reacting compounds of the formula III with compounds of the formula IV. As a rule, the starting compounds of the formulae IV and V are known. If they are not known, they can be prepared by methods known per se.

Compounds of the formula III can be obtained for example by means of reaction with $POCl_3$, starting from compounds which are synthesized from thiophene derivatives and CN-substituted heterocycles (Eur. J. Med. Chem. 23, 453 (1988).

The reaction of the compounds of the formula III with compounds of the formula IV is carried out under similar conditions regarding reaction time, temperature and solvent as has been described for the reaction of the compounds of the formula II with NH-containing heterocycles.

It is furthermore possible to convert a radical $R^3$ and/or $R^4$ in a compound of the formula I into a different radical $R^3$ and/or $R^4$, for example by reducing the nitro groups to amino groups (for example by hydrogenation on Raney nickel or Pd/charcoal in an inert solvent such as methanol or ethanol) or to hydrolyze cyano groups to give COOH groups.

Furthermore, free amino groups can be acylated in the customary manner with an acid chloride or acid anhydride or free amino groups alkylated in the customary manner with an unsubstituted or substituted alkyl halide, expediently in an inert solvent such as dichloromethane or THF and/or in the presence of a base such as triethylamine or pyridine at temperatures between −60 and +30°.

A base of the formula I may be converted with an acid to give the corresponding acid addition salt, for example by reacting equivalent amounts of the base and of the acid in an inert solvent such as ethanol, followed by evaporation. Particularly suitable acids for this reaction are those which give physiologically acceptable salts. Thus, it is possible to use inorganic acids, for example sulfuric acid, nitric acid, hydrohalic acids such as hydrochloric acid or hydrobromic acid, phosphorus acids such as orthophosphoric acid, sulfamic acid, furthermore organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedi-sulfonic acid, 2-hydroxyethanesulfonic acid, benzene-sulfonic acid, p-toluenesulfonic acid, naphthalenemono- and -disulfonic acids, laurylsulfuric acid. Salts with acids which are physiologically not acceptable, e.g. picrates, can be used for isolating and/or purifying the compounds of the formula I.

On the other hand, the free bases of the formula I may, if desired, be liberated from their salts by using bases (e.g. sodium hydroxide, sodium carbonate, potassum hydroxide or potassium carbonate).

The invention further relates to the use of the compounds of the formula I and/or their physiologically acceptable salts for the preparation of pharmaceutical products, in particular by non-chemical routes. They can be brought into a suitable pharmaceutical form together with at least one solid, liquid and/or semi-liquid excipient or auxiliary and, if appropriate, in combination with one or more other active ingredients.

The invention also relates to pharmaceuticals of the formula I and to their physiologically acceptable salts as phosphodiesterase V inhibitors.

The invention furthermore relates to pharmaceutical products comprising at least one compound of the formula I and/or a physiologically acceptable salt thereof.

These products can be used as pharmaceuticals in human or veterinary medicine. Suitable excipients are organic or inorganic substances which are suitable for enteral (e.g. oral), parenteral or topical adminstration and which do not react with the novel compounds, for example water, vegetable oils, benzyl alcohols, alkylene glycols, polyethylene glycols, glycerol triacetate, gelatin, carbohydrates such as lactose or starch, magnesium stearate, talc, petroleum jelly. Forms which are used for oral administration are, in particular, tablets, pills, sugar-coated tablets, capsules, powders, granules, syrups, liquids or drops, forms for rectal administration are, in particular suppositories, forms for parenteral administration are, in particular, solvents, preferably oily or aqueous solutions, furthermore suspensions, emulsions or implants, and forms for topical administration are ointments, creams or powders. The novel compounds may also be lyophilized and the resulting lyophilisates used for example for the preparation of injectable products. The abovementioned products can be in sterilized form and/or comprise auxiliaries such as glidants, preservatives, stabilizers and/or wetting agents, emulsifiers, salts for modifying the osmotic pressure, buffer substances, colourings, flavourings and/or other active ingredients, e.g. one or more vitamins.

The compounds of the formula I and their physiologically acceptable salts can be employed for combating diseases in which a raised cGMP (cyclo-guanosine monophosphate) level leads to the inhibition or prevention of inflammations and to muscular relaxation. The compounds according to the invention can be used especially in the treatment of diseases of the cardiovascular system and for the therapy of impaired potency.

All temperatures hereinabove and hereinbelow are given in ° C. In the examples which follow, "customary work-up" means: if required, water is added, if required, the pH is brought to between 2 and 10—-depending on the constitution of the end product—, the mixture is extracted with ethyl acetate or dichloromethane, and the organic phase is separated off, dried over sodium sulfate and evaporated, and the residue is purified by chromatography on silica gel and/or by crystallization.

Mass spectrometry (MS): EI (electron impact ionization) M+ FAB (fast atom bombardment) $(M+H)^+$

EXAMPLE 1

3.02 g of 3,4-methylenedioxybenzylamine ("A") are added to a solution of 3.29 g of 2,4-dichloro-6-methylthieno

[2,3-d]pyrimidine in 80 ml of dichloro-methane, and, after 1.52 g of triethylamine have been added, the mixture is stirred for 12 hours at room temperature. The solvent is removed and worked up as customary. This gives 3.38 g of 2-chloro-6-methyl-4-(3,4-methylenedioxybenzylamino) thieno[2,3-d]pyrimidine, m.p. 162°.

The following are obtained analogously by reacting "A":

with 2,4-dichloro-5-methylthieno[2,3-d]pyrimidine, 2-chloro-5-methyl-4-(3,4-methylenedioxybenzylamino) thieno[2,3-d]pyrimidine;
with 2,4-dichloro-5,6,7,8-tetrahydro[1]benzothieno[2,3-d] pyrimidine, 2-chloro-5,6,7,8-tetrahydro-4-(3,4-methylenedioxybenzylamino)[1]benzothieno[2,3-d] pyrimidine, m.p. 222°;
with 2,4-dichloro-5,6-cyclopenteno[1]benzothieno[2,3-d] pyrimidine, 2-chloro-5,6-cyclopenteno-4-(3,4-methylenedioxybenzylamino)thieno[2,3-d]pyrimidine;
with 2,4-dichloro-5,6-cyclohepteno[1]benzothieno[2,3-d] pyrimidine, 2-chloro-5,6-cyclohepteno-4-(3,4-methylenedioxybenzylamino)thieno[2,3-d]pyrimidine;
with 2,4-dichloro-6-ethylthieno[2,3-d]pyrimidine, 2-chloro-6-ethyl-4-(3,4-methylenedioxybenzylamino)thieno[2,3-d]pyrimidine, m.p. 148°;
with 2,4,6-trichlorothieno[2,3-d]pyrimidine, 2,6-dichloro-4-(3,4-methylenedioxybenzylamino)thieno[2,3-d]pyrimidine;
with 2,4,5-trichloro-6-methylthieno[2,3-d]pyrimidine, 2,5-dichloro-6-methyl-4-(3,4-methylenedioxybenzylamino)thieno[2,3-d]pyrimidine;
with 2,4-dichloro-6-nitrothieno[2,3-d]pyrimidine, 2-chloro-6-nitro-4-(3,4-methylenedioxybenzylamino)thieno[2,3-d]pyrimidine;
with 2,4-dichloro-5,6-dimethylthieno[2,3-d]pyrimidine, 2-chloro-5,6-dimethyl-4-(3,4-methylenedioxybenzylamino)thieno[2,3-d]pyrimidine;
with 2,4-dichloro-6-trifluoromethylthieno[2,3-d]pyrimidine, 2-chloro-6-trifluoromethyl-4-(3,4-methylenedioxybenzylamino)thieno[2,3-d]pyrimidine.

The following are obtained analogously by reaction of 3-chloro-4-methoxybenzylamine:

with 2,4-dichloro-6-methylthieno[2,3-d]pyrimidine, 2-chloro-6-methyl-4-(3-chloro-4-methoxybenzylamino) thieno[2,3-d]pyrimidine;
with 2,4-dichloro-5-methylthieno[2,3-d]pyrimidine, 2-chloro-5-methyl-4-(3-chloro-4-methoxybenzylamino) thieno[2,3-d]pyrimidine;
with 2,4-dichloro-5,6,7,8-tetrahydro[1]benzothieno[2,3-d] pyrimidine, 2-chloro-5,6,7,8-tetrahydro-4-(3-chloro-4-methoxybenzylamino)[1]benzothieno[2,3-d]pyrimidine;
with 2,4-dichloro-5,6-cyclopenteno[1]benzothieno[2,3-d] pyrimidine, 2-chloro-5,6-cyclopenteno-4-(3-chloro-4-methoxybenzylamino)thieno[2,3-d]pyrimidine;
with 2,4-dichloro-5,6-cyclohepteno[1]benzothieno[2,3-d] pyrimidine, 2-chloro-5,6-cyclohepteno-4-(3-chloro-4-methoxybenzylamino)thieno[2,3-d]pyrimidine;
with 2,4-dichloro-6-ethylthieno[2,3-d]pyrimidine, 2-chloro-6-ethyl-4-(3-chloro-4-methoxybenzylamino)thieno[2,3-d]pyrimidine;
with 2,4,6-trichlorothieno[2,3-d]pyrimidine, 2,6-dichloro-4-(3-chloro-4-methoxybenzylamino)thieno[2,3-d] pyrimidine;
with 2,4,5-trichloro-6-methylthieno[2,3-d]pyrimidine, 2,5-dichloro-6-methyl-4-(3-chloro-4-methoxybenzylamino) thieno[2,3-d]pyrimidine;
with 2,4-dichloro-6-nitrothieno[2,3-d]pyrimidine, 2-chloro-6-nitro-4-(3-chloro-4-methoxybenzylamino)thieno[2,3-d]pyrimidine;
with 2,4-dichloro-5,6-dimethylthieno[2,3-d]pyrimidine, 2-chloro-5,6-dimethyl-4-(3-chloro-4-methoxybenzylamino)thieno[2,3-d]pyrimidine;
with 2,4-dichloro-6-trifluoromethylthieno[2,3-d] pyrimidine; 2-chloro-6-trifluoromethyl-4-(3-chloro-4-methoxybenzylamino)thieno[2,3-d]pyrimidine.

The following are obtained analogously by reaction of 3,4-dimethoxybenzylamine:

with 2,4-dichloro-6-methylthieno[2,3-d]pyrimidine, 2-chloro-6-methyl-4-(3,4-dimethoxybenzylamino)thieno [2,3-d]pyrimidine;
with 2,4-dichloro-5-methylthieno[2,3-d]pyrimidine, 2-chloro-5-methyl-4-(3,4-dimethoxybenzylamino)thieno [2,3-d]pyrimidine;
with 2,4-dichloro-5,6,7,8-tetrahydro[1]benzothieno[2,3-d] pyrimidine, 2-chloro-5,6,7,8-tetrahydro-4-(3,4-dimethoxybenzylamino)[1]benzothieno[2,3-d] pyrimidine;
with 2,4-dichloro-5,6-cyclopenteno[1]benzothieno[2,3-d] pyrimidine, 2-chloro-5,6-cylopenteno-4-(3,4-dimethoxybenzylamino)thieno[2,3-d]pyrimidine;
with 2,4-dichloro-5,6-cyclohepteno[1]benzothieno[2,3-d] pyrimidine, 2-chloro-5,6-cylohepteno-4-(3,4-dimethoxybenzylamino)thieno[2,3-d]pyrimidine;
with 2,4-dichloro-6-ethylthieno[2,3-d]pyrimidine, 2-chloro-6-ethyl-4-(3,4-dimethoxybenzylamino)thieno[2,3-d] pyrimidine;
with 2,4,6-trichlorothieno[2,3-d]pyrimidine, 2,6-dichloro-4-(3,4-dimethoxybenzylamino)thieno[2,3-d]pyrimidine;
with 2,4,5-trichloro-6-methylthieno[2,3-d]pyrimidine, 2,5-dichloro-6-methyl-4-(3,4-dimethoxybenzylamino)thieno [2,3-d]pyrimidine;
with 2,4-dichloro-6-nitrothieno[2,3-d]pyrimidine, 2-chloro-6-nitro-4-(3,4-dimethoxybenzylamino)thieno[2,3-d] pyrimidine;
with 2,4-dichloro-5,6-dimethylthieno[2,3-d]pyrimidine, 2-chloro-5,6-dimethyl-4-(3,4-dimethoxybenzylamino) thieno[2,3-d]pyrimidine;
with 2,4-dichloro-6-trifluoromethylthieno[2,3-d]pyrimidine, 2-chloro-6-trifluoromethyl-4-(3,4-dimethoxybenzylamino)thieno[2,3-d]pyrimidine.

The following are obtained analogously by reaction of benzylamine:

with 2,4-dichloro-6-methylthieno[2,3-d]pyrimidine, 2-chloro-6-methyl-4-benzylamino-thieno[2,3-d] pyrimidine;
with 2,4-dichloro-5-methylthieno[2,3-d]pyrimidine, 2-chloro-5-methyl-4-benzylaminothieno[2,3-d] pyrimidine;
with 2,4-dichloro-5,6,7,8-tetrahydro[1]benzothieno[2,3-d] pyrimidine, 2-chloro-5,6,7,8-tetrahydro-4-benzylamino [1]benzothieno[2,3-d]pyrimidine;
with 2,4-dichloro-5,6-cyclopenteno[1]benzothieno[2,3-d] pyrimidine, 2-chloro-5,6-cyclopenteno-4-benzylaminothieno[2,3-d]pyrimidine;
with 2,4-dichloro-5,6-cyclohepteno[1]benzothieno[2,3-d] pyrimidine, 2-chloro-5,6-cyclohepteno-4-benzylaminothieno[2,3-d]pyrimidine;
with 2,4-dichloro-6-ethylthieno[2,3-d]pyrimidine, 2-chloro-6-ethyl-4-benzylaminothieno[2,3-d]pyrimidine, with 2,4,6-trichlorothieno[2,3-d]pyrimidine, 2,6-dichloro-4-benzylaminothieno[2,3-d]pyrimidine;

with 2,4,5-trichloro-6-methylthieno[2,3-d]pyrimidine, 2,5-dichloro-6-methyl-4-benzylaminothieno[2,3-d]pyrimidine;

with 2,4-dichloro-6-nitrothieno[2,3-d]pyrimidine, 2-chloro-6-nitro-4-benzylaminothieno[2,3-d]pyrimidine;

with 2,4-dichloro-5,6-dimethylthieno[2,3-d]pyrimidine, 2-chloro-5,6-dimethyl-4-benzylaminothieno[2,3-d]pyrimidine;

with 2,4-dichloro-6-trifluoromethylthieno[2,3-d]pyrimidine, 2,4-chloro-6-trifluoromethyl-4-benzylaminothieno[2,3-d]pyrimidine.

The following are obtained analogously by reaction of 4-fluoro-benzylamine:

with 2,4-dichloro-6-methylthieno[2,3-d]pyrimidine, 2-chloro-6-methyl-4-(4-fluorobenzylamino)thieno[2,3-d]pyrimidine;

with 2,4-dichloro-5-methylthieno[2,3-d]pyrimidine, 2-chloro-5-methyl-4-(4-fluorobenzylamino)thieno[2,3-d]pyrimidine;

with 2,4-dichloro-5,6,7,8-tetrahydro[1]benzothieno[2,3-d]pyrimidine, 2-chloro-5,6,7,8-tetrahydro-4-(4-fluorobenzylamino)[1]benzothieno[2,3-d]pyrimidine;

with 2,4-dichloro-5,6-cyclopenteno[1]benzothieno[2,3-d]pyrimidine, 2-chloro-5,6-cyclopenteno-4-(4-fluorobenzylamino)thieno[2,3-d]pyrimidine;

with 2,4-dichloro-5,6-cycloheptreno[1]benzothieno[2,3-d]pyrimidine, 2-chloro-5,6-cyclohepteno-4-(4-fluorobenzylamino)thieno[2,3-d]pyrimidine;

with 2,4-dichloro-6-ethylthieno[2,3-d]pyrimidine, 2-chloro-6-ethyl-4-(4-fluorobenzylamino)thieno[2,3-d]pyrimidine;

with 2,4,6-trichlorothieno[2,3-d]pyrimidine, 2,6-dichloro-4-(4-fluorobenzylamino)thieno[2,3-d]pyrimidine;

with 2,4,5-trichloro-6-methylthieno[2,3-d]pyrimidine, 2,5-dichloro-6-methyl-4-(4-fluorobenzylamino)thieno[2,3-d]pyrimidine;

with 2,4-dichloro-6-nitrothieno[2,3-d]pyrimidine, 2-chloro-6-nitro-4-(4-fluorobenzylamino)thieno[2,3-d]pyrimidine;

with 2,4-dichloro-5,6-dimethylthieno[2,3-d]pyrimidine, 2-chloro-5,6-dimethyl-4-(4-fluorobenzylamino)thieno[2,3-d]pyrimidine;

with 2,4-dichloro-6-trifluoromethylthieno[2,3-d]pyrimidine, 2-chloro-6-trifluoromethyl-4-(4-fluorobenzylamino)thieno[2,3-d]pyrimidine.

The following are obtained analogously by reaction of 3,4-dichlorobenzylamine:

with 2,4-dichloro-6-methylthieno[2,3-d]pyrimidine, 2-chloro-6-methyl-4-(3,4-dichlorobenzylamino)thieno[2,3-d]pyrimidine;

with 2,4-dichloro-5-methylthieno[2,3-d]pyrimidine, 2-chloro-5-methyl-4-(3,4-dichlorobenzylamino)thieno[2,3-d]pyrimidine;

with 2,4-dichloro-5,6,7,8-tetrahydro[1]benzothieno[2,3-d]pyrimidine, 2-chloro-5,6,7,8-tetrahydro-4-(3,4-dichlorobenzylamino)[1]benzothieno[2,3-d]pyrimidine;

with 2,4-dichloro-5,6-cyclopenteno[1]benzothieno[2,3-d]pyrimidine, 2-chloro-5,6-cyclopenteno-4-(3,4-dichlorobenzylamino)thieno[2,3-d]pyrimidine;

with 2,4-dichloro-5,6-cycloheptreno[1]benzothieno[2,3-d]pyrimidine, 2-chloro-5,6-cyclohepteno-4-(3,4-dichlorobenzylamino)thieno[2,3-d]pyrimidine;

with 2,4-dichloro-6-ethylthieno[2,3-d]pyrimidine, 2-chloro-6-ethyl-4-(3,4-dichlorobenzylamino)thieno[2,3-d]pyrimidine;

with 2,4,6-trichlorothieno[2,3-d]pyrimidine, 2,6-dichloro-4-(3,4-dichlorobenzylamino)thieno[2,3-d]pyrimidine;

with 2,4,5-trichloro-6-methylthieno[2,3-d]pyrimidine, 2,5-dichloro-6-methyl-4-(3,4-dichlorobenzylamino)thieno[2,3-d]pyrimidine;

with 2,4-dichloro-6-nitrothieno[2,3-d]pyrimidine, 2-chloro-6-nitro-4-(3,4-dichlorobenzylamino)thieno[2,3-d]pyrimidine;

with 2,4-dichloro-5,6-dimethylthieno[2,3-d]pyrimidine, 2-chloro-5,6-dimethyl-4-(3,4-dichlorobenzylamino)thieno[2,3-d]pyrimidine;

with 2,4-dichloro-6-trifluoromethylthieno[2,3-d]pyrimidine, 2-chloro-6-trifluoromethyl-4-(3,4-dichlorobenzylamino)thieno[2,3-d]pyrimidine.

The following are obtained analogously by reaction of 3-nitrobenzylamine:

with 2,4-dichloro-6-methylthieno[2,3-d]pyrimidine, 2-chloro-6-methyl-4-(3-nitrobenzylamino)thieno[2,3-d]pyrimidine;

with 2,4-dichloro-5-methylthieno[2,3-d]pyrimidine, 2-chloro-5-methyl-4-(3-nitrobenzylamino)thieno[2,3-d]pyrimidine;

with 2,4-dichloro-5,6,7,8-tetrahydro[1]benzothieno[2,3-d]pyrimidine, 2-chloro-5,6,7,8-tetrahydro-4-(3-nitrobenzylamino)[1]benzothieno[2,3-d]pyrimidine;

with 2,4-dichloro-5,6-cyclopenteno[1]benzothieno[2,3-d]pyrimidine, 2-chloro-5,6-cyclopenteno-4-(3-nitrobenzylamino)thieno[2,3-d]pyrimidine;

with 2,4-dichloro-5,6-cyclopenteno[1]benzothieno[2,3-d]pyrimidine, 2-chloro-5,6-cyclohepteno-4-(3-nitrobenzylamino)thieno[2,3-d]pyrimidine;

with 2,4-dichloro-6-ethylthieno[2,3-d]pyrimidine, 2-chloro-6-ethyl-4-(3-nitrobenzylamino)thieno[2,3-d]pyrimidine;

with 2,4,6-trichlorothieno[2,3-d]pyrimidine, 2,6-dichloro-4-(3-nitrobenzylamine)thieno[2,3-d]pyrimidine;

with 2,4,5-trichloro-6-methylthieno[2,3-d]pyrimidine, 2,5-dichloro-6-methyl-4-(3-nitrobenzylamino)thieno[2,3-d]pyrimidine;

with 2,4-dichloro-6-nitrothieno[2,3-d]pyrimidine, 6-chloro-6-nitro-4-(3-nitrobenzylamino)thieno[2,3-d]pyrimidine;

with 2,4-dichloro-5,6-dimethylthieno[2,3-d]pyrimidine, 2-chloro-5,6-dimethyl-4-(3-nitrobenzylamino)thieno[2,3-d]pyrimidine;

with 2,4-dichloro-6-trifluoromethylthieno[2,3-d]pyrimidine, 2-chloro-6-trifluoromethyl-4-(3-nitrobenzylamino)thieno[2,3-d]pyrimidine.

The following are obtained analogously by reaction of 3,4-methylenedioxyphenethylamine:

with 2,4-dichloro-6-methylthieno[2,3-d]pyrimidine, 2-chloro-6-methyl-4-(3,4-methylenephenethylamino)thieno[2,3-d]pyrimidine;

with 2,4-dichloro-5-methylthieno[2,3-d]pyrimidine, 2-chloro-5-methyl-4-(3,4-methylenedioxyphenethylamino)thieno[2,3-d]pyrimidine;

with 2,4-dichloro-5,6,7,8-tetrahydro[1]benzothieno[2,3-d]pyrimidine, 2-chloro-5,6,7,8-tetrahydro-4-(3,4-methylenedioxyphenethylamino)[1]benzothieno[2,3-d]pyrimidine;

with 2,4-dichloro-5,6-cyclopenteno[1]benzothieno[2,3-d]pyrimidine, 2-chloro-5,6-cyclopenteno-4-(3,4-methylenedioxyphenethylamino)thieno[2,3-d]pyrimidine;

with 2,4-dichloro-5,6-cyclohepteno[1]benzothieno[2,3-d]
pyrimidine, 2-chloro-5,6-cyclohepteno-4-(3,4-
methylenedioxyphenethylamino)thieno[2,3-d]
pyrimidine;

with 2,4-dichloro-6-ethylthieno-[2,3-d]pyrimidine,
2-chloro-6-ethyl-4-(3,4-methylenedioxyphenethylamino)
thieno[2,3-d]pyrimidine;

with 2,4,6-trichlorothieno[2,3-d]pyrimidine, 2,6-dichloro-4-
(3,4-methylenedioxyphenethylamino)thieno[2,3-d]
pyrimidine;

with 2,4,5-trichloro-6-methylthieno[2,3-d]pyrimidine, 2,5-
dichloro-6-methyl-4-(3,4-
methylenedioxyphenethylamino)thieno[2,3-d]
pyrimidine;

with 2,4-dichloro-6-nitrothieno[2,3-d]pyrimidine, 2-chloro-
6-nitro-4-(3,4-methylenedioxyphenethylamino)thieno[2,
3-d]pyrimidine;

with 2,4-dichloro-5,6-dimethylthieno[2,3-d]pyrimidine,
2-chloro-5,6-dimethyl-4-(3,4-
methylenedioxyphenethylamino)thieno[2,3-d]
pyrimidine;

with 2,4-dichloro-6-trifluoromethylthieno[2,3-d]pyrimidine,
2-chloro-6-trifluoromethyl-4-(3,4-
methylenedioxyphenethylamino)thieno[2,3-d]
pyrimidine;

The following are obtained analogously by reaction of
3,4-ethylenedioxybenzylamine:

with 2,4-dichloro-6-methylthieno[2,3-d]pyrimidine,
2-chloro-6-methyl-4-(3,4-ethylenedioxybenzylamino)
thieno[2,3-d]pyrimidine;

with 2,4-dichloro-5-methylthieno[2,3-d]pyrimidine,
2-chloro-5-methyl-4-(3,4-ethylenedioxybenzylamino)
thieno[2,3-d]pyrimidine;

with 2,4-dichloro-5,6,7,8-tetrahydro[1]benzothieno[2,3-d]
pyrimidine, 2-chloro-5,6,7,8-tetrahydro-4-(3,4-
ethylenedioxybenzylamino)[1]benzothieno[2,3-d]
pyrimidine;

with 2,4-dichloro-5,6-cyclopenteno[1]benzothieno[2,3-d]
pyrimidine, 2-chloro-5,6-cyclopenteno-4-(3,4-
ethylenedioxybenzylamino)thieno[2,3-d]pyrimidine;

with 2,4-dichloro-5,6-cyclohepteno[1]benzothieno[2,3-d]
pyrimidine, 2-chloro-5,6-cyclohepteno-4-(3,4-
ethylenedioxybenzylamino)thieno[2,3-d]pyrimidine;

with 2,4-dichloro-6-ethylthieno-[2,3-d]pyrimidine,
2-chloro-6-ethyl-4-(3,4-ethylenedioxybenzylamino)
thieno[2,3-d]pyrimidine;

with 2,4,6-trichlorothieno[2,3-d]pyrimidine, 2,6-dichloro-4-
(3,4-ethylenedioxybenzylamino)thieno[2,3-d]pyrimidine;

with 2,4,5-trichloro-6-methylthieno[2,3-d]pyrimidine, 2,5-
dichloro-6-methyl-4-(3,4-ethylenedioxybenzylamino)-
thieno[2,3-d]pyrimidine;

with 2,4-dichloro-6-nitrothieno[2,3-d]pyrimidine, 2-chloro-
6-nitro-4-(3,4-ethylenedioxybenzylamino)thieno[2,3-d]
pyrimidine;

with 2,4-dichloro-5,6-dimethylthieno[2,3-d]pyrimidine,
2-chloro-5,6-dimethyl-4-(3,4-
ethylenedioxybenzylamino)thieno[2,3-d]pyrimidine;

with 2,4-dichloro-6-trifluoromethylthieno[2,3-d]pyrimidine,
2-chloro-6-trifluoromethyl-4-(3,4-
ethylenedioxybenzylamino)thieno[2,3-d]pyrimidine;

EXAMPLE 2

1.67 g of 2-chloro-6-methyl-4-(3,4-
methylenedioxybenzylamino)thieno[2,3-d]pyrimidine, 1.02
g of imidazole and 2 g of phenol are heated for 5 hours at
150°. After cooling, the residue is dissolved in dichloromethane and worked as customary. This gives 1.0 g of
2-(imidazol-1-yl)-6-methyl-4-(3,4-
methylenedioxybenzylamino)thieno[2,3-d]pyrimidine, m.p.
248–250°.

The following compounds are obtained analogously by
reacting imidazole with the 2-chlorothieno[2,3-d]pyrimidine
derivatives obtained in Example 1, which are
arylalkylamino-substituted in the 4-position:

2-(imidazol-1-yl)-5-methyl-4-(3,4-
methylenedioxybenzylamino)thieno[2,3-d]pyrimidine,
m.p. 238°;

2-(imidazol-1-yl)-5,6,7,8-tetrahydro-4-(3,4-
methylenedioxybenzylamino)[1]benzothieno[2,3-d]
pyrimidine, m.p. 218°;

2-(imidazol-1-yl)-5,6-cyclopenteno-4-(3,4-
methylenedioxybenzylamino)thieno[2,3-d]pyrimidine,
m.p. 260°;

2-(imidazol-1-yl)-5,6-cyclohepteno-4-(3,4-
methylenedioxybenzylamino)thieno[2,3-d]pyrimidine,
m.p. 210°;

2-(imidazol-1-yl)-6-ethyl-4-(3,4-
methylenedioxybenzylamino)thieno[2,3-d]pyrimidine
methanesulfonate, m.p. 201°;

2-(imidazol-1-yl)-6-chloro-4-(3,4-
methylenedioxybenzylamino)thieno[2,3-d]pyrimidine;

2-(imidazol-1-yl)-5-chloro-6-methyl-4-(3,4-
methylenedioxybenzylamino)thieno[2,3-d]pyrimidine;

2-(imidazol-1-yl)-6-nitro-4-(3,4-
methylenedioxybenzylamino)thieno[2,3-d]pyrimidine;

2-(imidazol-1-yl)-5,6-dimethyl-4-(3,4-
methylenedioxybenzylamino)thieno[2,3-d]pyrimidine,
m.p. 245°;

2-(imidazol-1-yl)-6-trifluoromethyl-4-(3,4-
methylenedioxybenzylamino)thieno[2,3-d]pyrimidine;

2-(imidazol-1-yl)-6-methyl-4-(3-chloro-4-
methoxybenzylamino)thieno[2,3-d]pyrimidine;

2-(imidazol-1-yl)-5-methyl-4-(3-chloro-4-
methoxybenzylamino)thieno[2,3-d]pyrimidine;

2-(imidazol-1-yl)-5,6,7,8-tetrahydro-4-(3-chloro-4-
methoxybenzylamino)[1]benzothieno[2,3-d]pyrimidine;

2-(imidazol-1-yl)-5,6-cyclopenteno-4-(3-chloro-4-
methoxybenzylamino)thieno[2,3-d]pyrimidine;

2-(imidazol-1-yl)-5,6-cyclohepteno-4-(3-chloro-4-
methoxybenzylamino)thieno[2,3-d]pyrimidine;

2-(imidazol-1-yl)-6-ethyl-4-(3-chloro-4-
methoxybenzylamino)thieno[2,3-d]pyrimidine;

2-(imidazol-1-yl)-6-chloro-4-(3-chloro-4-
methoxybenzylamino)thieno[2,3-d]pyrimidine;

2-(imidazol-1-yl)-5-chloro-6-methyl-4-(3-chloro-4-
methoxybenzylamino)thieno[2,3-d]pyrimidine;

2-(imidazol-1-yl)-6-nitro-4-(3-chloro-4-
methoxybenzylamino)thieno[2,3-d]pyrimidine;

2-(imidazol-1-yl)-5,6-dimethyl-4-(3-chloro-4-
methoxybenzylamino)thieno[2,3-d]pyrimidine;

2-(imidazol-1-yl)-6-trifluoromethyl-4-(3-chloro-4-
methoxybenzylamino)thieno[2,3-d]pyrimidine;

2-(imidazol-1-yl)-6-methyl-4-(3,4-dimethoxy-
benzylamino)thieno[2,3-d]pyrimidine;

2-(imidazol-1-yl)-5-methyl-4-(3,4-dimethoxy-
benzylamino)thieno[2,3-d]pyrimidine;

2-(imidazol-1-yl)-5,6,7,8-tetrahydro-4-(3,4-
dimethoxybenzylamino)[1]benzothieno[2,3-d]
pyrimidine;

2-(imidazol-1-yl)-5,6-cyclopenteno-4-(3,4-
dimethoxybenzylamino)thieno[2,3-d]pyrimidine;

2-(imidazol-1-yl)-5,6-cycloheptено-4-(3,4-dimethoxybenzylamino)thieno[2,3-d]pyrimidine;
2-(imidazol-1-yl)-6-ethyl-4-(3,4-dimethoxybenzylamino)thieno[2,3-d]pyrimidine;
2-(imidazol-1-yl)-6-chloro-4-(3,4-dimethoxybenzylamino)thieno[2,3-d]pyrimidine;
2-(imidazol-1-yl)-5-chloro-6-methyl-4-(3,4-dimethoxybenzylamino)thieno[2,3-d]pyrimidine;
2-(imidazol-1-yl)-6-nitro-4-(3,4-dimethoxybenzylamino)thieno[2,3-d]pyrimidine;
2-(imidazol-1-yl)-5,6-dimethyl-4-(3,4-dimethoxybenzylamino)thieno[2,3-d]pyrimidine;
2-(imidazol-1-yl)-6-trifluoromethyl-4-(3,4-dimethoxybenzylamino)thieno[2,3-d]pyrimidine;
2-(imidazol-1-yl)-6-methyl-4-(3,4-dimethoxybenzylamino)thieno[2,3-d]pyrimidine;
2-(imidazol-1-yl)-6-methyl-4-benzylaminothieno[2,3-d]pyrimidine, m.p. 207°;
2-(imidazol-1-yl)-5-methyl-4-benzylaminothieno[2,3-d]pyrimidine;
2-(imidazol-1-yl)-5,6,7,8-tetrahydro-4-benzylamino[1]benzothieno[2,3-d]pyrimidine;
2-(imidazol-1-yl)-5,6-cyclopenteno-4-benzylaminothieno[2,3-d]pyrimidine;
2-(imidazol-1-yl)-5,6-cyclohepteno-4-benzylaminothieno[2,3-d]pyrimidine, m.p. 197°;
2-(imidazol-1-yl)-6-ethyl-4-benzylaminothieno[2,3-d]pyrimidine;
2-(imidazol-1-yl)-6-chloro-4-benzylaminothieno[2,3-d]pyrimidine;
2-(imidazol-1-yl)-5-chloro-6-methyl-4-benzylaminothieno[2,3-d]pyrimidine;
2-(imidazol-1-yl)-6-nitro-4-benzylaminothieno[2,3-d]pyrimidine;
2-(imidazol-1-yl)-5,6-dimethyl-4-benzylaminothieno[2,3-d]pyrimidine;
2-(imidazol-1-yl)-6-trifluoromethyl-4-benzylaminothieno[2,3-d]pyrimidine;
2-(imidazol-1-yl)-6-methyl-4-(4-fluorobenzylamino)thieno[2,3-d]pyrimidine;
2-(imidazol-1-yl)-5-methyl-4-(4-fluorobenzylamino)thieno[2,3-d]pyrimidine;
2-(imidazol-1-yl)-5,6,7,8-tetrahydro-4-(4-fluorobenzylamino)[1]benzothieno[2,3-d]pyrimidine;
2-(imidazol-1-yl)-5,6-cyclopenteno-4-(4-fluorobenzylamino)thien[2,3-d]pyrimidine;
2-(imidazol-1-yl)-5,6-cyclohepteno-4-(4-fluorobenzylamino)thieno[2,3-d]pyrimidine;
2-(imidazol-1-yl)-6-ethyl-4-(4-fluorobenzylamino)thieno[2,3-d]pyrimidine, m.p. 199°;
2-(imidazol-1-yl)-6-chloro-4-(4-fluorobenzylamino)thieno[2,3-d]pyrimidine;
2-(imidazol-1-yl)-5-chloro-6-methyl-4-(4-fluorobenzylamino)thieno[2,3-d]pyrimidine;
2-(imidazol-1-yl)-6-nitro-4-(4-fluorobenzylamino)thieno[2,3-d]pyrimidine,
2-(imidazol-1-yl)-5,6-dimethyl-4-(4-fluorobenzylamino)thieno[2,3-d]pyrimidine,
2-(imidazol-1-yl)-6-trifluoromethyl-4-(4-fluorobenzylamino)thieno[2,3-d]pyrimidine,
2-(imidazol-1-yl)-6-methyl-4-(3,4-dichlorobenzylamino)thieno[2,3-d]pyrimidine;
2-(imidazol-1-yl)-5-methyl-4-(3,4-dichlorobenzylamino)thieno[2,3-d]pyrimidine;
2-(imidazol-1-yl)-5,6,7,8-tetrahydro-4-(3,4-dichlorobenzylamino)[1]benzothieno[2,3-d]pyrimidine;
2-(imidazol-1-yl)-5,6-cyclopenteno-4-(3,4-dichlorobenzylamino)thieno[2,3-d]pyrimidine;
2-(imidazol-1-yl)-5,6-cyclohepteno-4-(3,4-dichlorobenzylamino)thieno[2,3-d]pyrimidine;
2-(imidazol-1-yl)-6-ethyl-4-(3,4-dichlorobenzylamino)thieno[2,3-d]pyrimidine;
2-(imidazol-1-yl)-6-chloro-4-(3,4-dichlorobenzylamino)thieno[2,3-d]pyrimidine;
2-(imidazol-1-yl)-5-chloro-6-methyl-4-(3,4-dichlorobenzylamino)thieno[2,3-d]pyrimidine;
2-(imidazol-1-yl)-6-nitro-4-(3,4-dichlorobenzylamino)thieno[2,3-d]pyrimidine;
2-(imidazol-1-yl)-5,6-dimethyl-4-(3,4-dichlorobenzylamino)thieno[2,3-d]pyrimidine;
2-(imidazol-1-yl)-6-trifluoromethyl-4-(3,4-dichlorobenzylamino)thieno[2,3-d]pyrimidine;
2-(imidazol-1-yl)-6-methyl-4-(3-nitrobenzylamino)thieno[2,3-d]pyrimidine;
2-(imidazol-1-yl)-5-methyl-4-(3-nitrobenzylamino)thieno[2,3-d]pyrimidine;
2-(imidazol-1-yl)-5,6,7,8-tetrahydro-4-(3-nitrobenzylamino)[1]benzothieno[2,3-d]pyrimidine;
2-(imidazol-1-yl)-5,6-cyclopenteno-4-(3-nitrobenzylamino)thieno[2,3-d]pyrimidine;
2-(imidazol-1-yl)-5,6-cyclohepteno-4-(3-nitrobenzylamino)thieno[2,3-d]pyrimidine;
2-(imidazol-1-yl)-6-ethyl-4-(3-nitrobenzylamino)thieno[2,3-d]pyrimidine;
2-(imidazol-1-yl)-6-chloro-4-(3-nitrobenzylamino)thieno[2,3-d]pyrimidine;
2-(imidazol-1-yl)-5-chloro-6-methyl-4-(3-nitrobenzylamino)thieno[2,3-d]pyrimidine;
2-(imidazol-1-yl)-6-nitro-4-(3-nitrobenzyl-amino)thieno[2,3-d]pyrimidine;
2-(imidazol-1-yl)-5,6-dimethyl-4-(3-nitrobenzylamino)thieno[2,3-d]pyrimidine;
2-(imidazol-1-yl)-6-trifluoromethyl-4-(3-nitrobenzylamino)thieno[2,3-d]pyrimidine;
2-(imidazol-1-yl)-6-methyl-4-(3,4-methylenedioxyphenethylamino)thieno[2,3-d]pyrimidine;
2-(imidazol-1-yl)-5-methyl-4-(3,4-methylenedioxyphenethylamino)thieno[2,3-d]pyrimidine;
2-(imidazol-1-yl)-5,6,7,8-tetrahydro-4-(3,4-methylenedioxyphenethylamino)[1]benzothieno[2,3-d]pyrimidine;
2-(imidazol-1-yl)-5,6-cyclopenteno-4-(3,4-methylenedioxyphenethylamino)thieno[2,3-d]pyrimidine;
2-(imidazol-1-yl)-5,6-cyclohepteno-4-(3,4-methylenedioxyphenethylamino)thieno[2,3-d]pyrimidine;
2-(imidazol-1-yl)-6-ethyl-4-(3,4-methylenedioxyphenethylamino)thieno[2,3-d]pyrimidine;
2-(imidazol-1-yl)-6-chloro-4-(3,4-methylenedioxyphenethylamino)thieno[2,3-d]pyrimidine;
2-(imidazol-1-yl)-5-chloro-6-methyl-4-(3,4-methylenedioxyphenethylamino)thieno[2,3-d]pyrimidine;
2-(imidazol-1-yl)-6-nitro-4-(3,4-methylenedioxyphenethylamino)thieno[2,3-d]pyrimidine;
2-(imidazol-1-yl)-5,6-dimethyl-4-(3,4-methylenedioxyphenethylamino)thieno[2,3-d]pyrimidine;
2-(imidazol-1-yl)-6-trifluoromethyl-4-(3,4-methylenedioxyphenethylamino)thieno[2,3-d]pyrimidine;

2-(imidazol-1-yl)-6-methyl-4-(3,4-ethylenedioxyphenethylamino)thieno[2,3-d]pyrimidine;
2-(imidazol-1-yl)-5-methyl-4-(3,4-ethylenedioxybenzylamino)thieno[2,3-d]pyrimidine;
2-(imidazol-1-yl)-5,6,7,8-tetrahydro-4-(3,4-ethylenedioxybenzylamino)[1]benzothieno[2,3-d]pyrimidine;
2-(imidazol-1-yl)-5,6-cyclopenteno-4-(3,4-ethylenedioxybenzylamino)thieno[2,3-d]pyrimidine;
2-(imidazol-1-yl)-5,6-cyclohepteno-4-(3,4-ethylenedioxybenzylamino)thieno[2,3-d]pyrimidine;
2-(imidazol-1-yl)-6-ethyl-4-(3,4-ethylenedioxybenzylamino)thieno[2,3-d]pyrimidine;
2-(imidazol-1-yl)-6-chloro-4-(3,4-ethylenedioxybenzylamino)thieno[2,3-d]pyrimidine;
2-(imidazol-1-yl)-5-chloro-6-methyl-4-(3,4-ethylenedioxybenzylamino)thieno[2,3-d]pyrimidine;
2-(imidazol-1-yl)-6-nitro-4-(3,4-ethylenedioxybenzylamino)thieno[2,3-d]pyrimidine;
2-(imidazol-1-yl)-5,6-dimethyl-4-(3,4-ethylenedioxybenzylamino)thieno[2,3-d]pyrimidine;
2-(imidazol-1-yl)-6-trifluoromethyl-4-(3,4-ethylenedioxybenzylamino)thieno[2,3-d]pyrimidine;

The following compounds are obtained analogously by reacting pyrazole with the 2-chlorothieno[2,3-d]pyrimidine derivatives obtained in Example 1, which are arylalkylamino-substituted in the 4-position:

2-(pyrazol-1-yl)-5-methyl-4-(3,4-methylenedioxybenzylamino)thieno[2,3-d]pyrimidine;
2-(pyrazol-1-yl)-5,6,7,8-tetrahydro-4-(3,4-methylenedioxybenzylamino)[1]benzothieno[2,3-d]pyrimidine, m.p. 210°;
2-(pyrazol-1-yl)-5,6-cyclopenteno-4-(3,4-methylenedioxybenzylamino)thieno[2,3-d]pyrimidine;
2-(pyrazol-1-yl)-5,6-cyclohepteno-4-(3,4-methylenedioxybenzylamino)thieno[2,3-d]pyrimidine;
2-(pyrazol-1-yl)-6-ethyl-4-(3,4-methylenedioxybenzylamino)thieno[2,3-d]pyrimidine;
2-(pyrazol-1-yl)-6-chloro-4-(3,4-methylenedioxybenzylamino)thieno[2,3-d]pyrimidine;
2-(pyrazol-1-yl)-5-chloro-6-methyl-4-(3,4-methylenedioxybenzylamino)thieno[2,3-d]pyrimidine;
2-(pyrazol-1-yl)-6-nitro-4-(3,4-methylenedioxybenzylamino)thieno[2,3-d]pyrimidine;
2-(pyrazol-1-yl)-5,6-dimethyl-4-(3,4-methylenedioxybenzylamino)thieno[2,3-d]pyrimidine;
2-(pyrazol-1-yl)-6-trifluoromethyl-4-(3,4-methylenedioxybenzylamino)thieno[2,3-d]pyrimidine;
2-(pyrazol-1-yl)-6-methyl-4-(3-chloro-4-methoxybenzylamino)thieno[2,3-d]pyrimidine;
2-(pyrazol-1-yl)-5-methyl-4-(3-chloro-4-methoxybenzylamino)thieno[2,3-d]pyrimidine;
2-(pyrazol-1-yl)-5,6,7,8-tetrahydro-4-(3-chloro-4-methoxybenzylamino)[1]benzothieno[2,3-d]pyrimidine;
2-(pyrazol-1-yl)-5,6-cyclopenteno-4-(3-chloro-4-methoxybenzylamino)thieno[2,3-d]pyrimidine;
2-(pyrazol-1-yl)-5,6-cyclohepteno-4-(3-chloro-4-methoxybenzylamino)thieno[2,3-d]pyrimidine;
2-(pyrazol-1-yl)-6-ethyl-4-(3-chloro-4-methoxybenzylamino)thieno[2,3-d]pyrimidine;
2-(pyrazol-1-yl)-6-chloro-4-(3-chloro-4-methoxybenzylamino)thieno[2,3-d]pyrimidine;
2-(pyrazol-1-yl)-5-chloro-6-methyl-4-(3-chloro-4-methoxybenzylamino)thieno[2,3-d]pyrimidine;
2-(pyrazol-1-yl)-6-nitro-4-(3-chloro-4-methoxybenzylamino)thieno[2,3-d]pyrimidine;
2-(pyrazol-1-yl)-5,6-dimethyl-4-(3-chloro-4-methoxybenzylamino)thieno[2,3-d]pyrimidine;
2-(pyrazol-1-yl)-6-trifluoromethyl-4-(3-chloro-4-methoxybenzylamino)thieno[2,3-d]pyrimidine;
2-(pyrazol-1-yl)-6-methyl-4-(3,4-dimethoxybenzylamino)thieno[2,3-d]pyrimidine;
2-(pyrazol-1-yl)-5-methyl-4-(3,4-dimethoxybenzylamino)thieno[2,3-d]pyrimidine;
2-(pyrazol-1-yl)-5,6,7,8-tetrahydro-4-(3,4-dimethoxybenzylamino)[1]benzothieno[2,3-d]pyrimidine;
2-(pyrazol-1-yl)-5,6-cyclopenteno-4-(3,4-dimethoxybenzylamino)thieno[2,3-d]pyrimidine;
2-(pyrazol-1-yl)-5,6-cyclohepteno-4-(3,4-dimethoxybenzylamino)thieno[2,3-d]pyrimidine;
2-(pyrazol-1-yl)-6-ethyl-4-(3,4-dimethoxybenzylamino)thieno[2,3-d]pyrimidine;
2-(pyrazol-1-yl)-6-chloro-4-(3,4-dimethoxybenzylamino)thieno[2,3-d]pyrimidine
2-(pyrazol-1-yl)-5-chloro-6-methyl-4-(3,4-dimethoxybenzylamino)thieno[2,3-d]pyrimidine;
2-(pyrazol-1-yl)-6-nitro-4-(3,4-dimethoxybenzylamino)thieno[2,3-d]pyrimidine
2-(pyrazol-1-yl)-5,6-dimethyl-4-(3,4-dimethoxybenzylamino)thieno[2,3-d]pyrimidine;
2-(pyrazol-1-yl)-6-trifluoromethyl-4-(3,4-dimethoxybenzylamino)thieno[2,3-d]pyrimidine;
2-(pyrazol-1-yl)-6-methyl-4-(3,4-dimethoxybenzylamino)thieno[2,3-d]pyrimidine;
2-(pyrazol-1-yl)-5-methyl-4-benzylaminothieno[2,3-d]pyrimidine;
2-(pyrazol-1-yl)-5,6,7,8-tetrahydro-4-benzylamino[1]benzothieno[2,3-d]pyrimidine;
2-(pyrazol-1-yl)-5,6-cyclopenteno-4-benzylaminothieno[2,3-d]pyrimidine;
2-(pyrazol-1-yl)-5,6-cyclohepteno-4-benzylaminothieno[2,3-d]pyrimidine;
2-(pyrazol-1-yl)-6-ethyl-4-benzylaminothieno[2,3-d]pyrimidine;
2-(pyrazol-1-yl)-6-chloro-4-benzylaminothieno[2,3-d]pyrimidine;
2-(pyrazol-1-yl)-5-chloro-6-methyl-4-benzylaminothieno[2,3-d]pyrimidine;
2-(pyrazol-1-yl)-6-nitro-4-benzylaminothieno[2,3-d]pyrimidine;
2-(pyrazol-1-yl)-5,6-dimethyl-4-benzylaminothieno[2,3-d]pyrimidine;
2-(pyrazol-1-yl)-6-trifluoromethyl-4-benzylaminothieno[2,3-d]pyrimidine;
2-(pyrazol-1-yl)-6-methyl-4-(4-fluorobenzylamino)thieno[2,3-d]pyrimidine;
2-(pyrazol-1-yl)-5-methyl-4-(4-fluorobenzylamino)thieno[2,3-d]pyrimidine;
2-(pyrazol-1-yl)-5,6,7,8-tetrahydro-4-(4-fluorobenzylamino)[1]benzothieno[2,3-d]pyrimidine;
2-(pyrazol-1-yl)-5,6-cyclopenteno-4-(4-fluorobenzylamino)thieno[2,3-d]pyrimidine;
2-(pyrazol-1-yl)-5,6-cyclohepteno-4-(4-fluorobenzylamino)thieno[2,3-d]pyrimidine;
2-(pyrazol-1-yl)-6-ethyl-4-(4-fluorobenzylamino)thieno[2,3-d]pyrimidine;
2-(pyrazol-1-yl)-6-chloro-4-(4-fluorobenzylamino)thieno[2,3-d]pyrimidine;
2-(pyrazol-1-yl)-5-chloro-6-methyl-4-(4-fluorobenzylamino)thieno[2,3-d]pyrimidine;
2-(pyrazol-1-yl)-6-nitro-4-(4-fluorobenzylamino)thieno[2,3-d]pyrimidine;

2-(pyrazol-1-yl)-5,6-dimethyl-4-(4-fluorobenzylamino) thieno[2,3-d]pyrimidine;
2-(pyrazol-1-yl)-6-trifluoromethyl-4-(4-fluorobenzylamino) thieno[2,3-d]pyrimidine;
2-(pyrazol-1-yl)-6-methyl-4-(3,4-dichlorobenzylamino) thieno[2,3-d]pyrimidine;
2-(pyrazol-1-yl)-5-methyl-4-(3,4-dichlorobenzylamino) thieno[2,3-d]pyrimidine;
2-(pyrazol-1-yl)-5,6,7,8-tetrahydro-4-(3,4-dichlorobenzylamino)[1]benzothieno[2,3-d]pyrimidine;
2-(pyrazol-1-yl)-5,6-cyclopenteno-4-(3,4-dichlorobenzylamino)thieno[2,3-d]pyrimidine;
2-(pyrazol-1-yl)-5,6-cyclohepteno-4-(3,4-dichlorobenzylamino)thieno[2,3-d]pyrimidine;
2-(pyrazol-1-yl)-6-ethyl-4-(3,4-dichlorobenzylamino) thieno[2,3-d]pyrimidine;
2-(pyrazol-1-yl)-6-chloro-4-(3,4-dichlorobenzylamino) thieno[2,3-d]pyrimidine;
2-(pyrazol-1-yl)-5-chloro-6-methyl-4-(3,4-dichlorobenzylamino)thieno[2,3-d]pyrimidine;
2-(pyrazol-1-yl)-6-nitro-4-(3,4-dichlorobenzylamino)thieno[2,3-d]pyrimidine;
2-(pyrazol-1-yl)-5,6-dimethyl-4-(3,4-dichlorobenzylamino) thieno[2,3-d]pyrimidine;
2-(pyrazol-1-yl)-6-trifluoromethyl-4-(3,4-dichlorobenzylamino)thieno[2,3-d]pyrimidine;
2-(pyrazol-1-yl)-6-methyl-4-(3-nitrobenzylamino)thieno[2,3-d]pyrimidine;
2-(pyrazol-1-yl)-5-methyl-4-(3-nitrobenzylamino)thieno[2,3-d]pyrimidine;
2-(pyrazol-1-yl)-5,6,7,8-tetrahydro-4-(3-nitrobenzylamino)[1]benzothieno[2,3-d]pyrimidine;
2-(pyrazol-1-yl)-5,6-cyclopenteno-4-(3-nitrobenzylamino) thieno[2,3-d]pyrimidine;
2-(pyrazol-1-yl)-5,6-cyclohepteno-4-(3-nitrobenzylamino) thieno[2,3-d]pyrimidine;
2-(pyrazol-1-yl)-6-ethyl-4-(3-nitrobenzylamino)thieno[2,3-d]pyrimidine;
2-(pyrazol-1-yl)-6-chloro-4-(3-nitrobenzylamino)thieno[2,3-d]pyrimidine;
2-(pyrazol-1-yl)-5-chloro-6-methyl-4-(3-nitrobenzylamino) thieno[2,3-d]pyrimidine;
2-(pyrazol-1-yl)-6-nitro-4-(3-nitrobenzylamino)thieno[2,3-d]pyrimidine;
2-(pyrazol-1-yl)-5,6-dimethyl-4-(3-nitrobenzylamino) thieno[2,3-d]pyrimidine;
2-(pyrazol-1-yl)-6-trifluoromethyl-4-(3-nitrobenzylamino) thieno[2,3-d]pyrimidine;
2-(pyrazol-1-yl)-6-methyl-4-(3,4-methylenedioxyphenethylamino)thieno[2,3-d]pyrimidine;
2-(pyrazol-1-yl)-5-methyl-4-(3,4-methylenedioxyphenethylamino)thieno[2,3-d]pyrimidine;
2-(pyrazol-1-yl)-5,6,7,8-tetrahydro-4-(3,4-methylenedioxyphenethylamino)[1]benzothieno[2,3-d]pyrimidine;
2-(pyrazol-1-yl)-5,6-cyclopenteno-4-(3,4-methylenedioxyphenethylamino)thieno[2,3-d]pyrimidine;
2-(pyrazol-1-yl)-5,6-cyclohepteno-4-(3,4-methylenedioxyphenethylamino)thieno[2,3-d]pyrimidine;
2-(pyrazol-1-yl)-6-ethyl-4-(3,4-methylenedioxyphenethylamino)thieno[2,3-d]pyrimidine;
2-(pyrazol-1-yl)-6-chloro-4-(3,4-methylenedioxyphenethylamino)thieno[2,3-d]pyrimidine;
2-(pyrazol-1-yl)-5-chloro-6-methyl-4-(3,4-methylenedioxyphenethylamino)thieno[2,3-d]pyrimidine;
2-(pyrazol-1-yl)-6-nitro-4-(3,4-methylenedioxyphenethylamino)thieno[2,3-d]pyrimidine;
2-(pyrazol-1-yl)-5,6-dimethyl-4-(3,4-methylenedioxyphenethylamino)thieno[2,3-d]pyrimidine;
2-(pyrazol-1-yl)-6-trifluoromethyl-4-(3,4-methylenedioxyphenethylamino)thieno[2,3-d]pyrimidine;
2-(pyrazol-1-yl)-6-methyl-4-(3,4-ethylenedioxyphenethylamino)thieno[2,3-d]pyrimidine;
2-(pyrazol-1-yl)-5-methyl-4-(3,4-ethylenedioxybenzylamino)thieno[2,3-d]pyrimidine;
2-(pyrazol-1-yl)-5,6,7,8-tetrahydro-4-(3,4-ethylenedioxybenzylamino)[1]benzothieno[2,3-d]pyrimidine;
2-(pyrazol-1-yl)-5,6-cyclopenteno-4-(3,4-ethylenedioxybenzylamino)thieno[2,3-d]pyrimidine;
2-(pyrazol-1-yl)-5,6-cyclohepteno-4-(3,4-ethylenedioxybenzylamino)thieno[2,3-d]pyrimidine;
2-(pyrazol-1-yl)-6-ethyl-4-(3,4-ethylenedioxybenzylamino) thieno[2,3-d]pyrimidine;
2-(pyrazol-1-yl)-6-chloro-4-(3,4-ethylenedioxybenzylamino)thieno[2,3-d]pyrimidine;
2-(pyrazol-1-yl)-5-chloro-6-methyl-4-(3,4-ethylenedioxybenzylamino)thieno[2,3-d]pyrimidine;
2-(pyrazol-1-yl)-6-nitro-4-(3,4-ethylenedioxybenzylamino) thieno[2,3-d]pyrimidine;
2-(pyrazol-1-yl)-5,6-dimethyl-4-(3,4-ethylenedioxybenzylamino)thieno[2,3-d]pyrimidine;
2-(pyrazol-1-yl)-6-trifluoromethyl-4-(3,4-ethylenedioxybenzylamino)thieno[2,3-d]pyrimidine.

The following compounds are obtained analogously by reacting 1,2,4-triazole with the 2-chlorothieno[2,3-d] pyrimidine derivatives obtained in Example 1, which are arylalkylamino-substituted in the 4-position:

2-(1,2,4-triazol-1-yl)-5-methyl-4-(3,4-methylenedioxybenzylamino)thieno[2,3-d]pyrimidine;
2-(1,2,4-triazol-1-yl)-5,6,7,8-tetrahydro-4-(3,4-methylenedioxybenzylamino)[1]benzothieno[2,3-d]pyrimidine;
2-(1,2,4-triazol-1-yl)-5,6-cyclopenteno-4-(3,4-methylenedioxybenzylamino)thieno[2,3-d]pyr-imidine;
2-(1,2,4-triazol-1-yl)-5,6-cyclohepteno-4-(3,4-methylenedioxybenzylamino)thieno[2,3-d]pyr-imidine;
2-(1,2,4-triazol-1-yl)-6-ethyl-4-(3,4-methylenedioxybenzylamino)thieno[2,3-d]pyrimidine;
2-(1,2,4-triazol-1-yl)-6-chloro-4-(3,4-methylenedioxybenzylamino)thieno[2,3-d]pyrimidine;
2-(1,2,4-triazol-1-yl)-5-chloro-6-methyl-4-(3,4-methylenedioxybenzylamino)thieno[2,3-d]pyrimidine;
2-(1,2,4-triazol-1-yl)-6-nitro-4-(3,4-methylenedioxybenzylamino)thieno[2,3-d]pyrimidine;
2-(1,2,4-triazol-1-yl)-5,6-dimethyl-4-(3,4-methylenedioxybenzylamino)thieno[2,3-d]pyrimidine;
2-(1,2,4-triazol-1-yl)-6-trifluoromethyl-4-(3,4-methylenedioxybenzylamino)thieno[2,3-d]pyrimidine;
2-(1,2,4-triazol-1-yl)-6-methyl-4-(3-chloro-4-methoxybenzylamino)thieno[2,3-d]pyrimidine;
2-(1,2,4-triazol-1-yl)-5-methyl-4-(3-chloro-4-methoxybenzylamino)thieno[2,3-d]pyrimidine;
2-(1,2,4-triazol-1-yl)-5,6,7,8-tetrahydro-4-(3-chloro-4-methoxybenzylamino)[1]benzothieno[2,3-d]pyrimidine;

2-(1,2,4-triazol-1-yl)-5,6-cyclopenteno-4-(3-chloro-4-methoxybenzylamino)thieno[2,3-d]pyrimidine;
2-(1,2,4-triazol-1-yl)-5,6-cyclohepteno-4-(3-chloro-4-methoxybenzylamino)thieno[2,3-d]pyrimidine;
2-(1,2,4-triazol-1-yl)-6-ethyl-4-(3-chloro-4-methoxybenzylamino)thieno[2,3-d]pyrimidine;
2-(1,2,4-triazol-1-yl)-6-chloro-4-(3-chloro-4-methoxybenzylamino)thieno[2,3-d]pyrimidine;
2-(1,2,4-triazol-1-yl)-5-chloro-6-methyl-4-(3-chloro-4-methoxybenzylamino)thieno[2,3-d]pyrimidine;
2-(1,2,4-triazol-1-yl)-6-nitro-4-(3-chloro-4-methoxybenzylamino)thieno[2,3-d]pyrimidine;
2-(1,2,4-triazol-1-yl)-5,6-dimethyl-4-(3-chloro-4-methoxybenzylamino)thieno[2,3-d]pyrimidine;
2-(1,2,4-triazol-1-yl)-6-trifluoromethyl-4-(3-chloro-4-methoxybenzylamino)thieno[2,3-d]pyrimidine;
2-(1,2,4-triazol-1-yl)-6-methyl-4-(3,4-dimethoxybenzylamino)thieno[2,3-d]pyrimidine;
2-(1,2,4-triazol-1-yl)-5-methyl-4-(3,4-dimethoxybenzylamino)thieno[2,3-d]pyrimidine;
2-(1,2,4-triazol-1-yl)-5,6,7,8-tetrahydro-4-(3,4-dimethoxybenzylamino)[1]benzothieno[2,3-d]pyrimidine;
2-(1,2,4-triazol-1-yl)-5,6-cyclopenteno-4-(3,4-dimethoxybenzylamino)thieno[2,3-d]pyrimidine;
2-(1,2,4-triazol-1-yl)-5,6-cyclohepteno-4-(3,4-dimethoxybenzylamino)thieno[2,3-d]pyrimidine;
2-(1,2,4-triazol-1-yl)-6-ethyl-4-(3,4-dimethoxybenzylamino)thieno[2,3-d]pyrimidine;
2-(1,2,4-triazol-1-yl)-6-chloro-4-(3,4-dimethoxybenzylamino)thieno[2,3-d]pyrimidine;
2-(1,2,4-triazol-1-yl)-5-chloro-6-methyl-4-(3,4-dimethoxybenzylamino)thieno[2,3-d]pyrimidine;
2-(1,2,4-triazol-1-yl)-6-nitro-4-(3,4-dimethoxybenzylamino)thieno[2,3-d]pyrimidine;
2-(1,2,4-triazol-1-yl)-5,6-dimethyl-4-(3,4-dimethoxybenzylamino)thieno[2,3-d]pyrimidine;
2-(1,2,4-triazol-1-yl)-6-trifluoromethyl-4-(3,4-dimethoxybenzylamino)thieno[2,3-d]pyrimidine;
2-(1,2,4-triazol-1-yl)-6-methyl-4-(3,4-dimethoxybenzylamino)thieno[2,3-d]pyrimidine;
2-(1,2,4-triazol-1-yl)-5-methyl-4-benzylaminothieno[2,3-d]pyrimidine;
2-(1,2,4-triazol-1-yl)-5,6,7,8-tetrahydro-4-benzylamino[1]benzothieno[2,3-d]pyrimidine;
2-(1,2,4-triazol-1-yl)-5,6-cyclopenteno-4-benzylaminothieno[2,3-d]pyrimidine;
2-(1,2,4-triazol-1-yl)-5,6-cyclohepteno-4-benzylaminothieno[2,3-d]pyrimidine;
2-(1,2,4-triazol-1-yl)-6-ethyl-4-benzylaminothieno[2,3-d]pyrimidine;
2-(1,2,4-triazol-1-yl)-6-chloro-4-benzylaminothieno[2,3-d]pyrimidine;
2-(1,2,4-triazol-1-yl)-5-chloro-6-methyl-4-benzylaminothieno[2,3-d]pyrimidine;
2-(1,2,4-triazol-1-yl)-6-nitro-4-benzylaminothieno[2,3-d]pyrimidine;
2-(1,2,4-triazol-1-yl)-5,6-dimethyl-4-benzylaminothieno[2,3-d]pyrimidine;
2-(1,2,4-triazol-1-yl)-6-trifluoromethyl-4-benzylaminothieno[2,3-d]pyrimidine;
2-(1,2,4-triazol-1-yl)-6-methyl-4-(4-fluorobenzylamino)thieno[2,3-d]pyrimidine;
2-(1,2,4-triazol-1-yl)-5-methyl-4-(4-fluorobenzylamino)thieno[2,3-d]pyrimidine;
2-(1,2,4-triazol-1-yl)-5,6,7,8-tetrahydro-4-(4-fluorobenzylamino)[1]benzothieno[2,3-d]pyrimidine.
2-(1,2,4-triazol-1-yl)-5,6-cyclopenteno-4-(4-fluorobenzylamino)thieno[2,3-d]pyrimidine;
2-(1,2,4-triazol-1-yl)-5,6-cyclohepteno-4-(4-fluorobenzylamino)thieno[2,3-d]pyrimidine;
2-(1,2,4-triazol-1-yl)-6-ethyl-4-(4-fluorobenzylamino)thieno[2,3-d]pyrimidine;
2-(1,2,4-triazol-1-yl)-6-chloro-4-(4-fluorobenzylamino)thieno[2,3-d]pyrimidine;
2-(1,2,4-triazol-1-yl)-5-chloro-6-methyl-4-(4-fluorobenzylamino)thieno[2,3-d]pyrimidine;
2-(1,2,4-triazol-1-yl)-6-nitro-4-(4-fluorobenzylamino)thieno[2,3-d]pyrimidine;
2-(1,2,4-triazol-1-yl)-5,6-dimethyl-4-(4-fluorobenzylamino)thieno[2,3-d]pyrimidine;
2-(1,2,4-triazol-1-yl)-6-trifluoromethyl-4-(4-fluorobenzylamino)thieno[2,3-d]pyrimidine;
2-(1,2,4-triazol-1-yl)-6-methyl-4-(3,4-dichlorobenzylamino)thieno[2,3-d]pyrimidine;
2-(1,2,4-triazol-1-yl)-5-methyl-4-(3,4-dichlorobenzylamino)thieno[2,3-d]pyrimidine;
2-(1,2,4-triazol-1-yl)-5,6,7,8-tetrahydro-4-(3,4-dichlorobenzylamino)[1]benzothieno[2,3-d]pyrimidine;
2-(1,2,4-triazol-1-yl)-5,6-cyclopenteno-4-(3,4-dichlorobenzylamino)thieno[2,3-d]pyrimidine;
2-(1,2,4-triazol-1-yl)-5,6-cyclohepteno-4-(3,4-dichlorobenzylamino)thieno[2,3-d]pyrimidine;
2-(1,2,4-triazol-1-yl)-6-ethyl-4-(3,4-dichlorobenzylamino)thieno[2,3-d]pyrimidine;
2-(1,2,4-triazol-1-yl)-6-chloro-4-(3,4-dichlorobenzylamino)thieno[2,3-d]pyrimidine;
2-(1,2,4-triazol-1-yl)-5-chloro-6-methyl-4-(3,4-dichlorobenzylamino)thieno[2,3-d]pyrimidine;
2-(1,2,4-triazol-1-yl)-6-nitro-4-(3,4-dichlorobenzylamino)thieno[2,3-d]pyrimidine;
2-(1,2,4-triazol-1-yl)-5,6-dimethyl-4-(3,4-dichlorobenzylamino)thieno[2,3-d]pyrimidine;
2-(1,2,4-triazol-1-yl)-6-trifluoromethyl-4-(3,4-dichlorobenzylamino)thieno[2,3-d]pyrimidine;
2-(1,2,4-triazol-1-yl)-6-methyl-4-(3-nitrobenzylamino)thieno[2,3-d]pyrimidine;
2-(1,2,4-triazol-1-yl)-5-methyl-4-(3-nitrobenzylamino)thieno[2,3-d]pyrimidine;
2-(1,2,4-triazol-1-yl)-5,6,7,8-tetrahydro-4-(3-nitrobenzylamino)[1]benzothieno[2,3-d]pyrimidine;
2-(1,2,4-triazol-1-yl)-5,6-cyclopenteno-4-(3-nitrobenzylamino)thieno[2,3-d]pyrimidine;
2-(1,2,4-triazol-1-yl)-5,6-cyclohepteno-4-(3-nitrobenzylamino)thieno[2,3-d]pyrimidine;
2-(1,2,4-triazol-1-yl)-6-ethyl-4-(3-nitrobenzylamino)thieno[2,3-d]pyrimidine;
2-(1,2,4-triazol-1-yl)-6-chloro-4-(3-nitrobenzylamino)thieno[2,3-d]pyrimidine;
2-(1,2,4-triazol-1-yl)-5-chloro-6-methyl-4-(3-nitrobenzylamino)thieno[2,3-d]pyrimidine;
2-(1,2,4-triazol-1-yl)-6-nitro-4-(3-nitrobenzylamino)thieno[2,3-d]pyrimidine;
2-(1,2,4-triazol-1-yl)-5,6-dimethyl-4-(3-nitrobenzylamino)thieno[2,3-d]pyrimidine;
2-(1,2,4-triazol-1-yl)-6-trifluoromethyl-4-(3-nitrobenzylamino)thieno[2,3-d]pyrimidine;
2-(1,2,4-triazol-1-yl)-6-methyl-4-(3,4-methylenedioxyphenethylamino)thieno[2,3-d]pyrimidine;
2-(1,2,4-triazol-1-yl)-5-methyl-4-(3,4-methylenedioxyphenethylamino)thieno[2,3-d]pyrimidine;
2-(1,2,4-triazol-1-yl)-5,6,7,8-tetrahydro-4-(3,4-methylenedioxyphenethylamino)[1]benzothieno[2,3-d]pyrimidine;

2-(1,2,4-triazol-1-yl)-5,6-cyclopenteno-4-(3,4-methylenedioxyphenethylamino)thieno[2,3-d]pyrimidine;
2-(1,2,4-triazol-1-yl)-5,6-cyclohepteno-4-(3,4-methylenedioxyphenethylamino)thieno[2,3-d]pyrimidine;
2-(1,2,4-triazol-1-yl)-6-ethyl-4-(3,4-methylenedioxyphenethylamino)thieno[2,3-d]pyrimidine;
2-(1,2,4-triazol-1-yl)-6-chloro-4-(3,4-methylenedioxyphenethylamino)thieno[2,3-d]pyrimidine;
2-(1,2,4-triazol-1-yl)-5-chloro-6-methyl-4-(3,4-methylenedioxyphenethylamino)thieno[2,3-d]pyrimidine;
2-(1,2,4-triazol-1-yl)-6-nitro-4-(3,4-methylenedioxyphenethylamino)thieno[2,3-d]pyrimidine;
2-(1,2,4-triazol-1-yl)-5,6-dimethyl-4-(3,4-methylenedioxyphenethylamino)thieno[2,3-d]pyrimidine;
2-(1,2,4-triazol-1-yl)-6-trifluoromethyl-4-(3,4-methylenedioxyphenethylamino)thieno[2,3-d]pyrimidine;
2-(1,2,4-triazol-1-yl)-6-methyl-4-(3,4-ethylenedioxybenzylamino)thieno[2,3-d]pyrimidine;
2-(1,2,4-triazol-1-yl)-5-methyl-4-(3,4-ethylenedioxybenzylamino)thieno[2,3-d]pyrimidine;
2-(1,2,4-triazol-1-yl)-5,6,7,8-tetrahydro-4-(3,4-ethylenedioxybenzylamino)[1]benzothieno[2,3-d]pyrimidine;
2-(1,2,4-triazol-1-yl)-5,6-cyclopenteno-4-(3,4-ethylenedioxybenzylamino)thieno[2,3-d]pyrimidine;
2-(1,2,4-triazol-1-yl)-5,6-cyclohepteno-4-(3,4-ethylenedioxybenzylamino)thieno[2,3-d]pyrimidine;
2-(1,2,4-triazol-1-yl)-6-ethyl-4-(3,4-ethylenedioxybenzylamino)thieno[2,3-d]pyrimidine;
2-(1,2,4-triazol-1-yl)-6-chloro-4-(3,4-ethylenedioxybenzylamino)thieno[2,3-d]pyrimidine;
2-(1,2,4-triazol-1-yl)-5-chloro-6-methyl-4-(3,4-ethylenedioxybenzylamino)thieno[2,3-d]pyrimidine;
2-(1,2,4-triazol-1-yl)-6-nitro-4-(3,4-ethylenedioxybenzylamino)thieno[2,3-d]pyrimidine;
2-(1,2,4-triazol-1-yl)-5,6-dimethyl-4-(3,4-ethylenedioxybenzylamino)thieno[2,3-d]pyrimidine;
2-(1,2,4-triazol-1-yl)-6-trifluoromethyl-4-(3,4-ethylenedioxybenzylamino)thieno[2,3-d]pyrimidine;

The following compounds are obtained analogously by reacting 2-methylimidazole with the 2-chlorothieno[2,3-d]pyrimidine derivatives obtained in Example 1, which are arylalkylamino-substituted in the 4-position:

2-(2-methylimidazol-1-yl)-5-methyl-4-(3,4-methylenedioxybenzylamino)thieno[2,3-d]pyrimidine;
2-(2-methylimidazol-1-yl)-5,6,7,8-tetrahydro-4-(3,4-methylenedioxybenzylamino)[1]benzothieno[2,3-d]pyrimidine, amorphous;
2-(2-methylimidazol-1-yl)-5,6-cyclopenteno-4-(3,4-methylenedioxybenzylamino)thieno[2,3-d]pyrim-idine;
2-(2-methylimidazol-1-yl)-5,6-cyclohepteno-4-(3,4-methylenedioxybenzylamino)thieno[2,3-d]pyrim-idine;
2-(2-methylimidazol-1-yl)-6-ethyl-4-(3,4-methylenedioxybenzylamino)thieno[2,3-d]pyrimidine;
2-(2-methylimidazol-1-yl)-6-chloro-4-(3,4-methylenedioxybenzylamino)thieno[2,3-d]pyrimidine;
2-(2-methylimidazol-1-yl)-5-chloro-6-methyl-4-(3,4-methylenedioxybenzylamino)thieno[2,3-d]pyrimidine;
2-(2-methylimidazol-1-yl)-6-nitro-4-(3,4-methylenedioxybenzylamino)thieno[2,3-d]pyrimidine;
2-(2-methylimidazol-1-yl)-5,6-dimethyl-4-(3,4-methylenedioxybenzylamino)thieno[2,3-d]pyrimidine;
2-(2-methylimidazol-1-yl)-6-trifluoromethyl-4-(3,4-methylenedioxybenzylamino)thieno[2,3-d]pyrimidine;
2-(2-methylimidazol-1-yl)-6-methyl-4-(3-chloro-4-methoxybenzylamino)thieno[2,3-d]pyrimidine;
2-(2-methylimidazol-1-yl)-5-methyl-4-(3-chloro-4-methoxybenzylamino)thieno[2,3-d]pyrimidine;
2-(2-methylimidazol-1-yl)-5,6,7,8-tetrahydro-4-(3-chloro-4-methoxybenzylamino)[1benzothieno(2,3-d]pyrimidine;
2-(2-methylimidazol-1-yl)-5,6-cyclopenteno-4-(3-chloro-4-methoxybenzylamino)thieno[2,3-d]pyrim-idine;
2-(2-methylimidazol-1-yl)-6-ethyl-4-(3-chloro-4-methoxybenzylamino)thieno[2,3-d]pyrimidine;
2-(2-methylimidazol-1-yl)-6-chloro-4-(3-chloro-4-methoxybenzylamino)thieno[2,3-d]pyrimidine;
2-(2-methylimidazol-1-yl)-5-chloro-6-methyl-4-(3-chloro-4-methoxybenzylamino)thieno[2,3-d]pyrimidine;
2-(2-methylimidazol-1-yl)-6-nitro-4-(3-chloro-4-methoxybenzylamino)thieno[2,3-d]pyrimidine;
2-(2-methylimidazol-1-yl)-5,6-dimethyl-4-(3-chloro-4-methoxybenzylamino)thieno[2,3-d]pyrimidine;
2-(2-methylimidazol-1-yl)-6-trifluoromethyl-4-(3-chloro-4-methoxybenzylamino)thieno[2,3-d]pyrimidine;
2-(2-methylimidazol-1-yl)-6-methyl-4-(3,4-dimethoxybenzylamino)thieno[2,3-d]pyrimidine;
2-(2-methylimidazol-1-yl)-5-methyl-4-(3,4-dimethoxybenzylamino)thieno[2,3-d]pyrimidine;
2-(2-methylimidazol-1-yl)-5,6,7,8-tetrahydro-4-(3,4-dimethoxybenzylamino)[1]benzothieno[2,3-d]pyrimidine;
2-(2-methylimidazol-1-yl)-5,6-cyclopenteno-4-dimethoxybenzylamino)thieno[2,3-d]pyrimidine;
2-(2-methylimidazol-1-yl)-5,6-cyclohepteno-4-dimethoxybenzylamino)thieno[2,3-d]pyrimidine;
2-(2-methylimidazol-1-yl)-6-ethyl-4-(3,4-dimethoxybenzylamino)thieno[2,3-d]pyrimidine;
2-(2-methylimidazol-1-yl)-6-chloro-4-(3,4-dimethoxybenzylamino)thieno[2,3-d]pyrimidine;
2-(2-methylimidazol-1-yl)-5-chloro-6-methyl-4-(3,4-dimethoxybenzylamino)thieno[2,3-d]pyrimidine;
2-(2-methylimidazol-1-yl)-6-nitro-4-(3,4-dimethoxybenzylamino)thieno[2,3-d]pyrimidine;
2-(2-methylimidazol-1-yl)-5,6-dimethyl-4-(3,4-dimethoxybenzylamino)thieno[2,3-d]pyrimidine;
2-(2-methylimidazol-1-yl)-6-trifluoromethyl-4-(3,4-dimethoxybenzylamino)thieno[2,3-d]pyrimidine;
2-(2-methylimidazol-1-yl)-6-methyl-4-(3,4-dimethoxybenzylamino)thieno[2,3-d]pyrimidine;
2-(2-methylimidazol-1-yl)-5-methyl-4-benzylaminothieno[2,3-d]pyrimidine;
2-(2-methylimidazol-1-yl)-5,6,7,8-tetrahydro-4-benzylamino[1]benzothieno[2,3-d]pyrimidine;
2-(2-methylimidazol-1-yl)-5,6-cyclopenteno-4-benzylaminothieno[2,3-d]pyrimidine;
2-(2-methylimidazol-1-yl)-5,6-cyclohepteno-4-benzylaminothieno[2,3-d]pyrimidine;
2-(2-methylimidazol-1-yl)-6-ethyl-4-benzylaminothieno[2,3-d]pyrimidine;
2-(2-methylimidazol-1-yl)-6-chloro-4-benzylaminothieno[2,3-d]pyrimidine;
2-(2-methylimidazol-1-yl)-5-chloro-6-methyl-4-benzylaminothieno[2,3-d]pyrimidine;
2-(2-methylimidazol-1-yl)-6-nitro-4-benzylaminothieno[2,3-d]pyrimidine;

2-(2-methylimidazol-1-yl)-5,6-dimethyl-4-benzylaminothieno[2,3-d]pyrimidine;
2-(2-methylimidazol-1-yl)-6-trifluoromethyl-4-benzylaminothieno[2,3-d]pyrimidine;
2-(2-methylimidazol-1-yl)-6-methyl-4-(4-fluorobenzylamino)thieno[2,3-d]pyrimidine;
2-(2-methylimidazol-1-yl)-5-methyl-4-(4-fluorobenzylamino)thieno[2,3-d]pyrimidine;
2-(2-methylimidazol-1-yl)-5,6,7,8-tetrahydro-4-(4-fluorobenzylamino)[1]benzothieno[2,3-d]pyrimidine;
2-(2-methylimidazol-1-yl)-5,6-cyclopenteno-4-(4-fluorobenzylamino)thieno[2,3-d]pyrimidine;
2-(2-methylimidazol-1-yl)-5,6-cyclohepteno-4-(4-fluorobenzylamino)thieno[2,3-d]pyrimidine;
2-(2-methylimidazol-1-yl)-6-ethyl-4-(4-fluorobenzylamino)thieno[2,3-d]pyrimidine;
2-(2-methylimidazol-1-yl)-6-chloro-4-(4-fluorobenzylamino)thieno[2,3-d]pyrimidine;
2-(2-methylimidazol-1-yl)-5-chloro-6-methyl-4-(4-fluorobenzylamino)thieno[2,3-d]pyrimidine;
2-(2-methylimidazol-1-yl)-6-nitro-4-(4-fluorobenzylaminothieno[2,3-d]pyrimidine;
2-(2-methylimidazol-1-yl)-5,6-dimethyl-4-(4-fluorobenzylamino)thieno[2,3-d]pyrimidine;
2-(2-methylimidazol-1-yl)-6-trifluoromethyl-4-(4-fluorobenzylamino)thieno[2,3-d]pyrimidine;
2-(2-methylimidazol-1-yl)-6-methyl-4-(3,4-dichlorobenzylamino)thieno[2,3-d]pyrimidine;
2-(2-methylimidazol-1-yl)-5-methyl-4-(3,4-dichlorobenzylamino)thieno[2,3-d]pyrimidine;
2-(2-methylimidazol-1-yl)-5,6,7,8-tetrahydro-4-(3,4-dichlorobenzylamino)[1]benzothieno[2,3-d]pyrimidine;
2-(2-methylimidazol-1-yl)-5,6-cyclopenteno-4-(3,4-dichlorobenzylamino)thieno[2,3-d]pyrimidine;
2-(2-methylimidazol-1-yl)-5,6-cyclohepteno-4-(3,4-dichlorobenzylamino)thieno[2,3-d]pyrimidine;
2-(2-methylimidazol-1-yl)-6-ethyl-4-(3,4-dichlorobenzylamino)thieno[2,3-d]pyrimidine
2-(2-methylimidazol-1-yl)-6-chloro-4-(3,4-dichlorobenzylamino)thieno[2,3-d]pyrimidine;
2-(2-methylimidazol-1-yl)-5-chloro-6-methyl-4-(3,4-dichlorobenzylamino)thieno[2,3-d]pyrimidine;
2-(2-methylimidazol-1-yl)-6-nitro-4-(3,4-dichlorobenzylamino)thieno[2,3-d]pyrimidine;
2-(2-methylimidazol-1-yl)-5,6-dimethyl-4-(3,4-dichlorobenzylamino)thieno[2,3-d]pyrimidine;
2-(2-methylimidazol-1-yl)-6-trifluoromethyl-4-(3,4-dichlorobenzylamino)thieno[2,3-d]pyrimidine;
2-(2-methylimidazol-1-yl)-6-methyl-4-(3-nitrobenzylamino)thieno[2,3-d]pyrimidine;
2-(2-methylimidazol-1-yl)-5-methyl-4-(3-nitrobenzylamino)thieno[2,3-d]pyrimidine;
2-(2-methylimidazol-1-yl)-5,6,7,8-tetrahydro-4-(3-nitrobenzylamino)[1]benzothieno[2,3-d]pyrimidine;
2-(2-methylimidazol-1-yl)-5,6-cyclopenteno-4-(3-nitrobenzylamino)thieno[2,3-d]pyrimidine;
2-(2-methylimidazol-1-yl)-5,6-cyclohepteno-4-(3-nitrobenzylamino)thieno[2,3-d]pyrimidine;
2-(2-methylimidazol-1-yl)-6-ethyl-4-(3-nitrobenzylamino)thieno[2,3-d]pyrimidine;
2-(2-methylimidazol-1-yl)-6-chloro-4-(3-nitrobenzylamino)thieno[2,3-d]pyrimidine;
2-(2-methylimidazol-1-yl)-5-chloro-6-methyl-4-(3-nitrobenzylamino)thieno[2,3-d]pyrimidine;
2-(2-methylimidazol-1-yl)-6-nitro-4-(3-nitrobenzylamino)thieno[2,3-d]pyrimidine;
2-(2-methylimidazol-1-yl)-5,6-dimethyl-4-(3-nitrobenzylamino)thieno[2,3-d]pyrimidine;
2-(2-methylimidazol-1-yl)-6-trifluoromethyl-4-(3-nitrobenzylamino)thieno[2,3-d]pyrimidine;
2-(2-methylimidazol-1-yl)-6-methyl-4-(3,4-methylenedioxyphenethylamino)thieno[2,3-d]pyrimidine
2-(2-methylimidazol-1-yl)-5-methyl-4-(3,4-methylenedioxyphenethylamino)thieno[2,3-d]pyrimidine;
2-(2-methylimidazol-1-yl)-5,6,7,8-tetrahydro-4-(3,4-methylenedioxyphenethylamino)[1]benzothieno[2,3-d]pyrimidine;
2-(2-methylimidazol-1-yl)-5,6-cyclopenteno-4-(3,4-methylenedioxyphenethylamino)thieno[2,3-d]pyrimidine;
2-(2-methylimidazol-1-yl)-5,6-cyclohepteno-4-(3,4-methylenedioxyphenethylamino)thieno[2,3-d]pyrimidine;
2-(2-methylimidazol-1-yl)-6-ethyl-4-(3,4-methylenedioxyphenethylamino)thieno[2,3-d]pyrimidine;
2-(2-methylimidazol-1-yl)-6-chloro-4-(3,4-methylenedioxyphenethylamino)thieno[2,3-d]pyrimidine;
2-(2-methylimidazol-1-yl)-5-chloro-6-methyl-4-(3,4-methylenedioxyphenethylamino)thieno[2,3-d]pyrimidine;
2-(2-methylimidazol-1-yl)-6-nitro-4-(3,4-methylenedioxyphenethylamino)thieno[2,3-d]pyrimidine;
2-(2-methylimidazol-1-yl)-5,6-dimethyl-4-(3,4-methylenedioxyphenethylamino)thieno[2,3-d]pyrimidine;
2-(2-methylimidazol-1-yl)-6-trifluoromethyl-4-(3,4-methylenedioxyphenethylamino)thieno[2,3-d]pyrimidine;
2-(2-methylimidazol-1-yl)-6-methyl-4-(3,4-ethylenedioxybenzylamino)thieno[2,3-d]pyrimidine;
2-(2-methylimidazol-1-yl)-5-methyl-4-(3,4-ethylenedioxybenzylamino)thieno[2,3-d]pyrimidine;
2-(2-methylimidazol-1-yl)-5,6,7,8-tetrahydro-4-(3,4-ethylenedioxybenzylamino)[1]benzothieno[2,3-d]pyrimidine;
2-(2-methylimidazol-1-yl)-5,6-cyclopenteno-4-(3,4-ethylenedioxybenzylamino)thieno[2,3-d]pyrimidine;
2-(2-methylimidazol-1-yl)-5,6-cyclohepteno-4-(3,4-ethylenedioxybenzylamino)thieno[2,3-d]pyrimidine;
2-(2-methylimidazol-1-yl)-6-ethyl-4-(3,4-ethylenedioxybenzylamino)thieno[2,3-d]pyrimidine;
2-(2-methylimidazol-1-yl)-6-chloro-4-(3,4-ethylenedioxybenzylamino)thieno[2,3-d]pyrimidine;
2-(2-methylimidazol-1-yl)-5-chloro-6-methyl-4-(3,4-ethylenedioxybenzylamino)thieno[2,3-d]pyrimidine;
2-(2-methylimidazol-1-yl)-6-nitro-4-(3,4-ethylenedioxybenzylamino)thieno[2,3-d]pyrimidine;
2-(2-methylimidazol-1-yl)-5,6-dimethyl-4-(3,4-ethylenedioxybenzylamino)thieno[2,3-d]pyrimidine;
2-(2-methylimidazol-1-yl)-6-trifluoromethyl-4-(3,4-ethylenedioxybenzylamino)thieno[2,3-d]pyrimidine.

EXAMPLE 3

5 g of 2-amino-5-methyl-3-ethoxycarbonylthiophene together with 2.7 g of 3-cyanopyridine are dissolved in 40 ml of dioxane. Then, gaseous HCl is passed through the solution for 5 hours. After customary workup, 6 g of 3,4-dihydro-4-oxo-2-(pyridin-3-yl)-6-methylthieno[2,3-d]pyrimidine are obtained.

The substitution of the keto group by Cl, with formation of the aromatic pyrmidine ring, takes place under standard conditions. A mixture of 18 ml of POCl₃ and 6 g of 3,4-dihydro-4-oxo-2-(pyridin-3-yl)-6-methylthieno[2,3-d]pyrimidine with addition of 1.8 ml of N,N-dimethylaniline is boiled for 4 hours. After customary work-up, 5 g of 4-chloro-2-(pyridin-3-yl)-6-methylthieno[2,3-d]pyrimidine are obtained.

The following are obtained analogously by reaction of 3-cyanopyridine and subsequent reaction with POCl₃:

from 2-amino-4-methyl-3-ethoxycarbonylthiophene, 4-chloro-2-(pyridin-3-yl)-5-methylthieno[2,3-d]pyrimidine;
from 2-amino-4,5,6,7-tetrahydro-3-ethoxycarbonylbenzothiophene, 4-chloro-2-(pyridin-3-yl)-5,6,7,8-tetrahydro[1]benzothieno[2,3-d]pyrimidine, m.p. 143°;
from 2-amino-4,5-cyclopenteno-3-ethoxycarbonylthiophene, 4-chloro-2-(pyridin-3-yl)-5,6-cyclopentenothieno[2,3-d]pyrimidine;
from 2-amino-4,5-cyclohepteno-3-ethoxycarbonylthiophene, 4-chloro-2-(pyridin-3-yl)-5,6-cycloheptenothieno[2,3-d]pyrimidine;
from 2-amino-5-ethyl-3-ethoxycarbonylthiophene, 4-chloro-2-(pyridin-3-yl)-6-ethylthieno[2,3-d]pyrimidine;
from 2-amino-5-chloro-3-ethoxycarbonylthiophene, 4-chloro-2-(pyridin-3-yl)-6-chlorothieno[2,3-d]pyrimidine;
from 2-amino-4-chloro-5-methyl-3-ethoxycarbonylthiophene, 4-chloro-2-(pyridin-3-yl)-5-chloro-6-methylthieno[2,3-d]pyrimidine;
from 2-amino-5-nitro-3-ethoxycarbonylthiophene, 4-chloro-2-(pyridin-3-yl)-6-nitrothieno[2,3-d]pyrimidine;
from 2-amino-4,5-dimethyl-3-ethoxycarbonylthiophene, 4-chloro-2-(pyridin-3-yl)-5,6-dimethylthieno[2,3-d]pyrimidine;
from 2-amino-5-trifluoromethyl-3-ethoxycarbonylthiophene, 4-chloro-2-(pyridin-3-yl)-6-trifluoromethylthieno[2,3-d]pyrimidine.

The following are obtained analogously by reaction of 5-cyanoisoxazole and subsequent reaction with POCl₃:

from 2-amino-5-methyl-3-ethoxycarbonylthiophene, 4-chloro-2-(isoxazol-5-yl)-6-methylthieno[2,3-d]pyrimidine;
from 2-amino-4-methyl-3-ethoxycarbonylthiophene, 4-chloro-2-(isoxazol-5-yl)-5-methylthieno[2,3-d]pyrimidine;
from 2-amino-4,5,6,7-tetrahydro-3-ethoxycarbonylbenzothiophene, 4-chloro-2-(isoxazol-5-yl)-5,6,7,8-tetrahydro[1]benzothieno[2,3-d]pyrimidine;
from 2-amino-4,5-cyclopenteno-3-ethoxycarbonylthiophene, 4-chloro-2-(isoxazol-5-yl)-5,6-cyclopentenothieno[2,3-d]pyrimidine;
from 2-amino-4,5-cyclohepteno-3-ethoxycarbonylthiophene, 4-chloro-2-(isoxazol-5-yl)-5,6-cycloheptenothieno[2,3-d]pyrimidine;
from 2-amino-5-ethyl-3-ethoxycarbonylthiophene, 4-chloro-2-(isoxazol-5-yl)-6-ethylthieno[2,3-d]pyrimidine;
from 2-amino-5-chloro-3-ethoxycarbonylthiophene, 4-chloro-2-(isoxazol-5-yl)-6-chlorothieno[2,3-d]pyrimidine;
from 2-amino-4-chloro-5-methyl-3-ethoxycarbonylthiophene, 4-chloro-2-(isoxazol-5-yl)-5-chloro-6-ethylthieno[2,3-d]pyrimidine;
from 2-amino-5-nitro-3-ethoxycarbonylthiophene, 4-chloro-2-(isoxazol-5-yl)-6-nitrothieno[2,3-d]pyrimidine;
from 2-amino-4,5-dimethyl-3-ethoxycarbonylthiophene, 4-chloro-2-(isoxazol-5-yl)-5,6-dimethylthieno[2,3-d]pyrimidine;
from 2-amino-5-trifluoromethyl-3-ethoxycarbonylthiophene, 4-chloro-2-(isoxazol-5-yl)-6-trifluoromethylthieno[2,3-d]pyrimidine;

The following are obtained analogously by reaction of 2-cyanopyrazine and subsequent reaction with POCl₃:

from 2-amino-5-methyl-3-ethoxycarbonylthiophene, 4-chloro-2-(pyrazin-2-yl)-6-methylthieno[2,3-d]pyrimidine;
from 2-amino-4-methyl-3-ethoxycarbonylthiophene, 4-chloro-2-(pyrazin-2-yl)-5-methylthieno[2,3-d]pyrimidine;
from 2-amino-4,5,6,7-tetrahydro-3-ethoxycarbonylbenzothiophene, 4-chloro-2-(pyrazin-2-yl)-5,6,7,8-tetrahydro[1]benzothieno[2,3-d]pyrimidine;
from 2-amino-4,5-cyclopenteno-3-ethoxycarbonylthiophene, 4-chloro-2-(pyrazin-2-yl)-5,6-cyclopentenothieno[2,3-d]pyrmidine;
from 2-amino-4,5-cyclohepteno-3-ethoxycarbonylthiophene, 4-chloro-2-(pyrazin-2-yl)-5,6-cycloheptenothieno[2,3-d]pyrimidine;
from 2-amino-5-ethyl-3-ethoxycarbonylthiophene, 4-chloro-2-(pyrazin-2-yl)-6-ethylthieno[2,3-d]pyrimidine;
from 2-amino-5-chloro-3-ethoxycarbonylthiophene, 4-chloro-2-(pyrazin-2-yl)-6-chlorothieno[2,3-d]pyrimidine;
from 2-amino-4-chloro-5-methyl-3-ethoxycarbonylthiophene, 4-chloro-2-(pyrazin-2-yl)-5-chloro-6-methylthieno[2,3-d]pyrimidine;
from 2-amino-5-nitro-3-ethoxycarbonylthiophene, 4-chloro-2-(pyrazin-2-yl)-6-nitrothieno[2,3-d]pyrimidine;
from 2-amino-4,5-dimethyl-3-ethoxycarbonylthiophene, 4-chloro-2-(pyrazin-2-yl)-5,6-dimethylthieno[2,3-d]pyrimidine;
from 2-amino-5-trifluoromethyl-3-ethoxycarbonylthiophene, 4-chloro-2-(pyrazin-2-yl)-6-trifluoromethylthieno[2,3-d]pyrimidine.

The following are obtained analogously by reaction of 2-cyanopyridine and subsequent reaction with POCl₃:

from 2-amino-5-methyl-3-ethoxycarbonylthiophene, 4-chloro-2-(pyridin-2-yl)-6-methylthieno[2,3-d]pyrimidine;
from 2-amino-4-methyl-3-ethoxycarbonylthiophene, 4-chloro-2-(pyridin-2-yl)-5-methylthieno[2,3-d]pyrimidine;
from 2-amino-4,5,6,7-tetrahydro-3-ethoxycarbonylbenzothiophene; 4-chloro-2-(pyridin-2-yl)-5,6,7,8-tetrahydro[1]benzothieno[2,3-d]pyrimidine;
from 2-amino-4,5-cyclopenteno-3-ethoxycarbonylthiophene, 4-chloro-2-(pyridin-2-yl)-5,6-cyclopentenothieno[2,3-d]pyrimidine;
from 2-amino-4,5-cyclohepteno-3-ethoxycarbonylthiophene, 4-chloro-2-(pyridin-2-yl)-5,6-cycloheptenothieno[2,3-d]pyrimidine;
from 2-amino-5-ethyl-3-ethoxycarbonylthiophene, 4-chloro-2-(pyridin-2-yl)-6-ethylthieno[2,3-d]pyrimidine;

from 2-amino-5-chloro-3-ethoxycarbonylthiophene, 4-chloro-2-(pyridin-2-yl)-6-chlorothieno[2,3-d]pyrimidine;

from 2-amino-4-chloro-5-methyl-3-ethoxycarbonylthiophene, 4-chloro-2-(pyridin-2-yl)-5-chloro-6-methylthieno[2,3-d]pyrimidine;

from 2-amino-5-nitro-3-ethoxycarbonylthiophene, 4-chloro-2-(pyridin-2-yl)-6-nitrothieno[2,3-d]pyrimidine;

from 2-amino-4,5-dimethyl-3-ethoxycarbonylthiophene, 4-chloro-2-(pyridin-2-yl)-5,6-dimethylthieno[2,3-d]pyrimidine;

from 2-amino-5-trifluoromethyl-3-ethoxycarbonylthiophene, 4-chloro-2-(pyridin-2-yl)-6-trifluoromethylthieno[2,3-d]pyrimidine.

The following are obtained analogously by reaction of 4-cyanopyridine and subsequent reaction with POCl$_3$:

from 2-amino-5-methyl-3-ethoxycarbonylthiophene, 4-chloro-2-(pyridin-4-yl)-6-methylthieno[2,3-d]pyrimidine;

from 2-amino-4-methyl-3-ethoxycarbonylthiophene, 4-chloro-2-(pyridin-4-yl)-5-methylthieno[2,3-d]pyrimidine;

from 2-amino-4,5,6,7-tetrahydro-3-ethoxycarbonylbenzothiophene; 4-chloro-2-(pyridin-4-yl)-5,6,7,8-tetrahydro[1]benzothieno[2,3-d]pyrimidine;

from 2-amino-4,5-cyclopenteno-3-ethoxycarbonylthiophene, 4-chloro-2-(pyridin-4-yl)-5,6-cyclopentenothieno[2,3-d]pyrimidine;

from 2-amino-4,5-cyclohepteno-3-ethoxycarbonylthiophene, 4-chloro-2-(pyridin-4-yl)-5,6-cycloheptenothieno[2,3-d]pyrimidine;

from 2-amino-5-ethyl-3-ethoxycarbonylthiophene, 4-chloro-2-(pyridin-4-yl)-6-ethylthieno[2,3-d]pyrimidine;

from 2-amino-5-chloro-3-ethoxycarbonylthiophene, 4-chloro-2-(pyridin-4-yl)-6-chlorothieno[2,3-d]pyrimidine;

from 2-amino-4-chloro-5-methyl-3-ethoxycarbonylthiophene, 4-chloro-2-(pyridin-4-yl)-5-chloro-6-methylthieno[2,3-d]pyrimidine;

from 2-amino-5-nitro-3-ethoxycarbonylthiophene, 4-chloro-2-(pyridin-4-yl)-6-nitrothieno[2,3-d]pyrimidine;

from 2-amino-4,5-dimethyl-3-ethoxycarbonylthiophene, 4-chloro-2-(pyridin-4-yl)-5,6-dimethylthieno[2,3-d]pyrimidine;

from 2-amino-5-trifluoromethyl-3-ethoxycarbonylthiophene, 4-chloro-2-(pyridin-4-yl)-6-trifluoromethylthieno[2,3-d]pyrimidine.

EXAMPLE 4

The following are obtained analogously to Example 1 by reaction of 3,4-methylenedioxybenzylamine:

with 4-chloro-2-(pyridin-3-yl)-6-methylthieno[2,3-d]pyrimidine, 2-(pyridin-3-yl)-4-(3,4-methylenedioxybenzylamino)-6-methylthieno[2,3-d]pyrimidine;

with 4-chloro-2-(pyridin-3-yl)-5-methylthieno[2,3-d]pyrimidine, 2-(pyridin-3-yl)-4-(3,4-methylenedioxybenzylamino)-5-methylthieno[2,3-d]pyrimidine;

with 4-chloro-2-(pyridin-3-yl)-5,6,7,8-tetrahydro[1]benzothieno[2,3-d]pyrimidine, 2-(pyridin-3-yl)-4-(3,4-methylenedioxybenzylamino)-5,6,7,8-tetrahydro[1]benzothieno[2,3-d]pyrimidine, m.p. 215°;

with 4-chloro-2-(pyridin-3-yl)-5,6-cyclopentenothieno[2,3-d]pyrimidine, 2-(pyridin-3-yl)-4-(3,4-methylenedioxybenzylamino)-5,6-cyclopentenothieno[2,3-d]pyrimidine, with 4-chloro-2-(pyridin-3-yl)-5,6-cycloheptenothieno[2,3-d]pyrimidine, 2-(pyridin-3-yl)-4-(3,4-methylenedioxybenzylamino)-5,6-cycloheptenothieno[2,3-d]pyrimidine;

with 4-chloro-2-(pyridin-3-yl)-6-ethylthieno[2,3-d]pyrimidine, 2-(pyridin-3-yl)-4-(3,4-methylenedioxybenzylamino)-6-ethylthieno[2,3-d]pyrimidine;

with 4-chloro-2-(pyridin-3-yl)-6-chlorothieno[2,3-d]pyrimidine, 2-(pyridin-3-yl)-4-(3,4-methylenedioxybenzylamino)-6-chlorothieno[2,3-d]pyrimidine;

with 4-chloro-2-(pyridin-3-yl)-5-chloro-6-methylthieno[2,3-d]pyrimidine, 2-(pyridin-3-yl)-4-(3,4-methylenedioxybenzylamino)-5-chloro-6-methylthieno[2,3-d]pyrimidine;

with 4-chloro-2-(pyridin-3-yl)-6-nitrothieno[2,3-d]pyrimidine, 2-(pyridin-3-yl)-4-(3,4-methylenedioxybenzylamino)-6-nitrothieno[2,3-d]pyrimidine;

with 4-chloro-2-(pyridin-3-yl)-5,6-dimethylthieno[2,3-d]pyrimidine, 2-(pyridin-3-yl)-4-(3,4-methylenedioxybenzylamino)-5,6-dimethylthieno[2,3-d]pyrimidine;

with 4-chloro-2-(pyridin-3-yl)-6-trifluoromethylthieno[2,3-d]pyrimidine, 2-(pyridin-3-yl)-4-(3,4-methylenedioxybenzylamino)-6-trifluoromethylthieno[2,3-d]pyrimidine, with 4-chloro-2-(isoxazol-5-yl)-6-methylthieno[2,3-d]pyrimidine, 2-(isoxazol-5-yl)-4-(3,4-methylenedioxybenzylamino)-6-methylthieno[2,3-d]pyrimidine;

with 4-chloro-2-(isoxazol-5-yl)-5-methylthieno-[2,3-d]pyrimidine, 2-(isoxazol-5-yl)-4-(3,4-methylenedioxybenzylamino)-5-methylthieno[2,3-d]pyrimidine;

with 4-chloro-2-(isoxazol-5-yl)-5,6,7,8-tetrahydro[1]benzothieno[2,3-d]pyrimidine, 2-(isoxazol-5-yl)-4-(3,4-methylenedioxybenzylamino)-5,6,7,8-tetrahydro[1]benzothieno[2,3-d]pyrimidine;

with 4-chloro-2-(isoxazol-5-yl)-5,6-cyclopentenothieno[2,3-d]pyrimidine, 2-(isoxazol-5-yl)-4-(3,4-methylenedioxybenzylamino)-5,6-cyclopentenothieno[2,3-d]pyrimidine;

with 4-chloro-2-(isoxazol-5-yl)-5,6-cycloheptenothieno[2,3-d]pyrimidine, 2-(isoxazol-5-yl)-4-(3,4-methylenedioxybenzylamino)-5,6-cycloheptenothieno[2,3-d]pyrimidine;

with 4-chloro-2-(isoxazol-5-yl)-6-ethylthieno[2,3-d]pyrimidine, 2-(isoxazol-5-yl)-4-(3,4-methylenedioxybenzylamino)-6-ethylthieno[2,3-d]pyrimidine;

with 4-chloro-2-(isoxazol-5-yl)-6-chlorothieno[2,3-d]pyrimidine, 2-(isoxazol-5-yl)-4-(3,4-methylenedioxybenzylamino)-6-chlorothieno[2,3-d]pyrimidine;

with 4-chloro-2-(isoxazol-5-yl)-5-chloro-6-methylthieno[2,3-d]pyrimidine, 2-(isoxazol-5-yl)-4-(3,4-methylenedioxybenzylamino)-5-chloro-6-methylthieno[2,3-d]pyrimidine;

with 4-chloro-2-(isoxazol-5-yl)-6-nitrothieno[2,3-d]pyrimidine, 2-(isoxazol-5-yl)-4-(3,4-methylenedioxybenzylamino)-6-nitrothieno[2,3-d]pyrimidine;

with 4-chloro-2-(isoxazol-5-yl)-5,6-dimethylthieno[2,3-d]pyrimidine, 2-(isoxazol-5-yl)-4-(3,4-methylenedioxybenzylamino)-5,6-dimethylthieno[2,3-d]pyrimidine;

with 4-chloro-2-(isoxazol-5-yl)-6-trifluoromethylthieno[2,3-d]pyrimidine, 2-(isoxazol-5-yl)-4-(3,4-methylenedioxybenzylamino)-6-trifluoromethylthieno[2,3-d]pyrimidine;

with 4-chloro-2-(pyrazin-2-yl)-6-methylthieno[2,3-d]pyrimidine, 2-(pyrazin-2-yl)-4-(3,4-methylenedioxybenzylamino)-6-methylthieno[2,3-d]pyrimidine;

with 4-chloro-2-(pyrazin-2-yl)-5-methylthieno-[2,3-d]pyrimidine, 2-(pyrazin-2-yl)-4-(3,4-methylenedioxybenzylamino)-5-methylthieno[2,3-d]pyrimidine;

with 4-chloro-2-(pyrazin-2-yl)-5,6,7,8-tetrahydro[1]benzothieno[2,3-d]pyrimidine, 2-(pyrazin-2-yl)-4-(3,4-methylenedioxybenzylamino)-5,6,7,8-tetrahydro[1]benzothieno[2,3-d]pyrimidine;

with 4-chloro-2-(pyrazin-2-yl)-5,6-cyclopentenothieno[2,3-d]pyrimidine, 2-(pyrazin-2-yl)-4-(3,4-methylenedioxybenzylamino)-5,6-cyclopentenothieno[2,3-d]pyrimidine with 4-chloro-2-(pyrazin-2-yl)-5,6-cycloheptenothieno[2,3-d]pyrimidine, 2-(pyrazin-2-yl)-4-(3,4-methylenedioxybenzylamino)-5,6-cycloheptenothieno[2,3-d]pyrimidine with 4-chloro-2-(pyrazin-2-yl)-6-ethylthieno[2,3-d]pyrimidine, 2-(pyrazin-2-yl)-4-(3,4-methylenedioxybenzylamino)-6-ethylthieno[2,3-d]pyrimidine with 4-chloro-2-(pyrazin-2-yl)-6-chlorothieno[2,3-d]pyrimidine, 2-(pyrazin-2-yl)-4-(3,4-methylenedioxybenzylamino)-6-chlorothieno[2,3-d]pyrimidine with 4-chloro-2-(pyrazin-2-yl)-5-chloro-6-methylthieno[2,3-d]pyrimidine, 2-(pyrazin-2-yl)-4-(3,4-methylenedioxybenzylamino)-5-chloro-6-methylthieno[2,3-d]pyrimidine with 4-chloro-2-(pyrazin-2-yl)-6-nitrothieno[2,3-d]pyrimidine, 2-(pyrazin-2-yl)-4-(3,4-methylenedioxybenzylamino)-6-nitrothieno[2,3-d]pyrimidine with 4-chloro-2-(pyrazin-2-yl)-5,6-dimethylthieno[2,3-d]pyrimidine, 2-(pyrazin-2-yl)-4-(3,4-methylenedioxybenzylamino)-5,6-dimethylthieno[2,3-d]pyrimidine with 4-chloro-2-(pyrazin-2-yl)-6-trifluoromethylthieno[2,3-d]pyrimidine, 2-(pyrazin-2-yl)-4-(3,4-methylenedioxybenzylamino)-6-trifluoromethylthieno[2,3-d]pyrimidine with 4-chloro-2-(pyridin-2-yl)-6-methylthieno[2,3-d]pyrimidine, 2-(pyridin-2-yl)-4-(3,4-methylenedioxybenzylamino)-6-methylthieno[2,3-d]pyrimidine with 4-chloro-2-(pyridin-2-yl)-5-methylthieno[2,3-d]pyrimidine, 2-(pyridin-2-yl)-4-(3,4-methylenedioxybenzylamino)-5-methylthieno[2,3-d]pyrimidine;

with 4-chloro-2-(pyridin-2-yl)-5,6,7,8-tetrahydro[1]benzothieno[2,3-d]pyrimidine, 2-(pyridin-2-yl)-4-(3,4-methylenedioxybenzylamino)-5,6,7,8-tetrahydro[1]benzothieno[2,3-d]pyrimidine;

with 4-chloro-2-(pyridin-2-yl)-5,6-cyclopentenothieno[2,3-d]pyrimidine, 2-(pyridin-2-yl)-4-(3,4-methylenedioxybenzylamino)-5,6-cyclopentenothieno[2,3-d]pyrimidine with 4-chloro-2-(pyridin-2-yl)-5,6-cycloheptenothieno[2,3-d]pyrimidine, 2-(pyridin-2-yl)-4-(3,4-methylenedioxybenzylamino)-5,6-cycloheptenothieno[2,3-d]pyrimidine with 4-chloro-2-(pyridin-2-yl)-6-ethylthieno[2,3-d]pyrimidine, 2-(pyridin-2-yl)-4-(3,4-methylenedioxybenzylamino)-6-ethylthieno[2,3-d]pyrimidine with 4-chloro-2-(pyridin-2-yl)-6-chlorothieno[2,3-d]pyrimidine, 2-(pyridin-2-yl)-4-(3,4-methylenedioxybenzylamino)-6-chlorothieno[2,3-d]pyrimidine with 4-chloro-2-(pyridin-2-yl)-5-chloro-6-methylthieno[2,3-d]pyrimidine, 2-(pyridin-2-yl)-4-(3,4-methylenedioxybenzylamino)-5-chloro-6-methylthieno[2,3-d]pyrimidine with 4-chloro-2-(pyridin-2-yl)-6-nitrothieno[2,3-d]pyrimidine, 2-(pyridin-2-yl)-4-(3,4-methylenedioxybenzylamino)-6-nitrothieno[2,3-d]pyrimidine with 4-chloro-2-(pyridin-2-yl)-5,6-dimethylthieno[2,3-d]pyrimidine, 2-(pyridin-2-yl)-4-(3,4-methylenedioxybenzylamino)-5,6-dimethylthieno[2,3-d]pyrimidine with 4-chloro-2-(pyridin-2-yl)-6-trifluoromethylthieno[2,3-d]pyrimidine, 2-(pyridin-2-yl)-4-(3,4-methylenedioxybenzylamino)-6-trifluoromethylthieno[2,3-d]pyrimidine with 4-chloro-2-(pyridin-4-yl)-6-methylthieno[2,3-d]pyrimidine, 2-(pyridin-4-yl)-4-(3,4-methylenedioxybenzylamino)-6-methylthieno[2,3-d]pyrimidine with 4-chloro-2-(pyridin-4-yl)-5-methylthieno-[2,3-d]pyrimidine, 2-(pyridin-4-yl)-4-(3,4-methylenedioxybenzylamino)-5-methylthieno[2,3-d]pyrimidine;

with 4-chloro-2-(pyridin-4-yl)-5,6,7,8-tetrahydro[1]benzothieno[2,3-d]pyrimidine, 2-(pyridin-4-yl)-4-(3,4-methylenedioxybenzylamino)-5,6,7,8-tetrahydro[1]benzothieno[2,3-d]pyrimidine, m.p. 185°;

with 4-chloro-2-(pyridin-4-yl)-5,6-cyclopentenothieno[2,3-d]pyrimidine, 2-(pyridin-4-yl)-4-(3,4-methylenedioxybenzylamino)-5,6-cyclopentenothieno[2,3-d]pyrimidine;

with 4-chloro-2-(pyridin-4-yl)-5,6-cycloheptenothieno[2,3-d]pyrimidine, 2-(pyridin-4-yl)-4-(3,4-methylenedioxybenzylamino)-5,6-cycloheptenothieno[2,3-d]pyrimidine;

with 4-chloro-2-(pyridin-4-yl)-6-ethylthieno[2,3-d]pyrimidine, 2-(pyridin-4-yl)-4-(3,4-methylenedioxybenzylamino)-6-ethylthieno[2,3-d]pyrimidine;

with 4-chloro-2-(pyridin-4-yl)-6-chlorothieno[2,3-d]pyrimidine, 2-(pyridin-4-yl)-4-(3,4-methylenedioxybenzylamino)-6-chlorothieno[2,3-d]pyrimidine;

with 4-chloro-2-(pyridin-4-yl)-5-chloro-6-methylthieno[2,3-d]pyrimidine, 2-(pyridin-4-yl)-4-(3,4-methylenedioxybenzylamino)-5-chloro-6-methylthieno[2,3-d]pyrimidine;

with 4-chloro-2-(pyridin-4-yl)-6-nitrothieno[2,3-d]pyrimidine, 2-(pyridin-4-yl)-4-(3,4-methylenedioxybenzylamino)-6-nitrothieno[2,3-d]pyrimidine;

with 4-chloro-2-(pyridin-4-yl)-5,6-dimethylthieno[2,3-d]pyrimidine, 2-(pyridin-4-yl)-4-(3,4-methylenedioxybenzylamino)-5,6-dimethylthieno[2,3-d]pyrimidine;

with 4-chloro-2-(pyridin-4-yl)-6-trifluoromethylthieno[2,3-d]pyrimidine, 2-(pyridin-4-yl)-4-(3,4-methylenedioxybenzylamino)-6-trifluoromethylthieno[2,3-d]pyrimidine;

The following are obtained analogously by reaction of 3-chloro-4-methoxybenzylamine:

with 4-chloro-2-(pyridin-3-yl)-6-methylthieno[2,3-d]pyrimidine, 2-(pyridin-3-yl)-4-(3-chloro-4-methoxybenzylamino)-6-methylthieno[2,3-d]pyrimidine;

with 4-chloro-2-(pyridin-3-yl)-5-methylthieno[2,3-d]pyrimidine, 2-(pyridin-3-yl)-4-(3-chloro-4-methoxybenzylamino)-5-methylthieno[2,3-d]pyrimidine;

with 4-chloro-2-(pyridin-3-yl)-5,6,7,8-tetrahydro[1]benzothieno[2,3-d]pyrimidine, 2-(pyridin-3-yl)-4-(3-chloro-4-methoxybenzylamino)-5,6,7,8-tetrahydro[1]benzothieno[2,3-d]pyrimidine;

with 4-chloro-2-(pyridin-3-yl)-5,6-cyclopentenothieno[2,3-d]pyrimidine, 2-(pyridin-3-yl)-4-(3-chloro-4-methoxybenzylamino)-5,6-cyclopentenothieno[2,3-d]pyrimidine;

with 4-chloro-2-(pyridin-3-yl)-5,6-cycloheptenothieno[2,3-d]pyrimidine, 2-(pyridin-3-yl)-4-(3-chloro-4-methoxybenzylamino)-5,6-cycloheptenothieno[2,3-d]pyrimidine;

with 4-chloro-2-(pyridin-3-yl)-6-ethylthieno[2,3-d]pyrimidine, 2-(pyridin-3-yl)-4-(3-chloro-4-methoxybenzylamino)-6-ethylthieno[2,3-d]pyrimidine;

with 4-chloro-2-(pyridin-3-yl)-6-chlorothieno[2,3-d]pyrimidine, 2-(pyridin-3-yl)-4-(3-chloro-4-methoxybenzylamino)-6-chlorothieno[2,3-d]pyrimidine;

with 4-chloro-2-(pyridin-3-yl)-5-chloro-6-methylthieno[2,3-d]pyrimidine, 2-(pyridin-3-yl)-4-(3-chloro-4-methoxybenzylamino)-5-chloro-6-methylthieno[2,3-d]pyrimidine with 4-chloro-2-(pyridin-3-yl)-6-nitrothieno[2,3-d]pyrimidine, 2-(pyridin-3-yl)-4-(3-chloro-4-methoxybenzylamino)-6-nitrothieno[2,3-d]pyrimidine;

with 4-chloro-2-(pyridin-3-yl)-5,6-dimethylthieno[2,3-d]pyrimidine, 2-(pyridin-3-yl)-4-(3-chloro-4-methoxybenzylamino)-5,6-dimethylthieno[2,3-d]pyrimidine;

with 4-chloro-2-(pyridin-3-yl)-6-trifluoromethylthieno[2,3-d]pyrimidine, 2-(pyridin-3-yl)-4-(3-chloro-4-methoxybenzylamino)-6-trifluoromethylthieno[2,3-d]pyrimidine;

with 4-chloro-2-(isoxazol-5-yl)-6-methylthieno[2,3-d]pyrimidine, 2-(isoxazol-5-yl)-4-(3-chloro-4-methoxybenzylamino)-6-methylthieno[2,3-d]pyrimidine;

with 4-chloro-2-(isoxazol-5-yl)-5-methylthieno[2,3-d]pyrimidine, 2-(isoxazol-5-yl)-4-(3-chloro-4-methoxybenzylamino)-5-methylthieno[2,3-d]pyrimidine;

with 4-chloro-2-(isoxazol-5-yl)-5,6,7,8-tetrahydro[1]benzothieno[2,3-d]-pyrimidine, 2-(isoxazol-5-yl)-4-(3-chloro-4-methoxybenzylamino)-5,6,7,8-tetrahydro[1]benzothieno[2,3-d]pyrimidine;

with 4-chloro-2-(isoxazol-5-yl)-5,6-cyclopentenothieno[2,3-d]pyrimidine, 2-(isoxazol-5-yl)-4-(3-chloro-4-methoxybenzylamino)-5,6-cyclopentenothieno[2,3-d]pyrimidine;

with 4-chloro-2-(isoxazol-5-yl)-5,6-cycloheptenothieno[2,3-d]pyrimidine, 2-(isoxazol-5-yl)-4-(3-chloro-4-methoxybenzylamino)-5,6-cycloheptenothieno[2,3-d]pyrimidine;

with 4-chloro-2-(isoxazol-5-yl)-6-ethylthieno[2,3-d]pyrimidine, 2-(isoxazol-5-yl)-4-(3-chloro-4-methoxybenzylamino)-6-ethylthieno[2,3-d]pyrimidine;

with 4-chloro-2-(isoxazol-5-yl)-6-chlorothieno[2,3-d]pyrimidine, 2-(isoxazol-5-yl)-4-(3-chloro-4-methoxybenzylamino)-6-chlorothieno[2,3-d]pyrimidine;

with 4-chloro-2-(isoxazol-5-yl)-5-chloro-6-methylthieno[2,3-d]pyrimidine, 2-(isoxazol-5-yl)-4-(3-chloro-4-methoxybenzylamino)-5-chloro-6-methylthieno[2,3-d]pyrimidine;

with 4-chloro-2-(isoxazol-5-yl)-6-nitrothieno[2,3-d]pyrimidine, 2-(isoxazol-5-yl)-4-(3-chloro-4-methoxybenzylamino)-6-nitrothieno[2,3-d]pyrimidine;

with 4-chloro-2-(isoxazol-5-yl)-5,6-dimethylthieno[2,3-d]pyrimidine, 2-(isoxazol-5-yl)-4-(3-chloro-4-methoxybenzylamino)-5,6-dimethylthieno[2,3-d]pyrimidine;

with 4-chloro-2-(isoxazol-5-yl)-6-trifluoromethylthieno[2,3-d]pyrimidine, 2-(isoxazol-5-yl)-4-(3-chloro-4-methoxybenzylamino)-6-trifluoromethylthieno[2,3-d]pyrimidine;

with 4-chloro-2-(pyrazin-2-yl)-6-methylthieno[2,3-d]pyrimidine, 2-(pyrazin-2-yl)-4-(3-chloro-4-methoxybenzylamino)-6-methylthieno[2,3-d]pyrimidine;

with 4-chloro-2-(pyrazin-2-yl)-5-methylthieno[2,3-d]pyrimidine, 2-(pyrazin-2-yl)-4-(3-chloro-4-methoxybenzylamino)-5-methylthieno[2,3-d]pyrimidine;

with 4-chloro-2-(pyrazin-2-yl)-5,6,7,8-tetrahydro[1]benzothieno[2,3-d]-pyrimidine, 2-(pyrazin-2-yl)-4-(3-chloro-4-methoxybenzylamino)-5,6,7,8-tetrahydro[1]benzothieno[2,3-d]pyrimidine;

with 4-chloro-2-(pyrazin-2-yl)-5,6-cyclopentenothieno[2,3-d]pyrimidine, 2-(pyrazin-2-yl)-4-(3-chloro-4-methoxybenzylamino)-5,6-cyclopentenothieno[2,3-d]pyrimidine;

with 4-chloro-2-(pyrazin-2-yl)-5,6-cycloheptenothieno[2,3-d]pyrimidine, 2-(pyrazin-2-yl)-4-(3-chloro-4-methoxybenzylamino)-5,6-cycloheptenothieno[2,3-d]pyrim-idine;

with 4-chloro-2-(pyrazin-2-yl)-6-ethylthieno[2,3-d]pyrimidine, 2-(pyrazin-2-yl)-4-(3-chloro-4-methoxybenzylamino)-6-ethylthieno[2,3-d]pyrimidine;

with 4-chloro-2-(pyrazin-2-yl)-6-chlorothieno[2,3-d]pyrimidine, 2-(pyrazin-2-yl)-4-(3-chloro-4-methoxybenzylamino)-6-chlorothieno[2,3-d]pyrimidine;

with 4-chloro-2-(pyrazin-2-yl)-5-chloro-6-methylthieno[2,3-d]pyrimidine, 2-(pyrazin-2-yl)-4-(3-chloro-4-methoxybenzylamino)-5-chloro-6-methylthieno[2,3-d]pyrimidine;

with 4-chloro-2-(pyrazin-2-yl)-6-nitrothieno[2,3-d]pyrimidine, 2-(pyrazin-2-yl)-4-(3-chloro-4-methoxybenzylamino)-6-nitrothieno[2,3-d]pyrimidine;

with 4-chloro-2-(pyrazin-2-yl)-5,6-dimethylthieno[2,3-d]pyrimidine, 2-(pyrazin-2-yl)-4-(3-chloro-4-methoxybenzylamino)-5,6-dimethylthieno[2,3-d]pyrimidine;

with 4-chloro-2-(pyrazin-2-yl)-6-trifluoromethylthieno[2,3-d]pyrimidine, 2-(pyrazin-2-yl)-4-(3-chloro-4-methoxybenzylamino)-6-trifluoromethylthieno[2,3-d]pyrimidine;

with 4-chloro-2-(pyridin-2-yl)-6-methylthieno[2,3-d]pyrimidine, 2-(pyridin-2-yl)-4-(3-chloro-4-methoxybenzylamino)-6-methylthieno[2,3-d]pyrimidine;

with 4-chloro-2-(pyridin-2-yl)-5-methylthieno[2,3-d]pyrimidine, 2-(pyridin-2-yl)-4-(3-chloro-4-methoxybenzylamino)-5-methylthieno[2,3-d]pyrimidine;

with 4-chloro-2-(pyridin-2-yl)-5,6,7,8-tetrahydro[1]benzothieno[2,3-d]pyrimidine, 2-(pyridin-2-yl)-4-(3-chloro-4-methoxybenzylamino)-5,6,7,8-tetrahydro[1]benzothieno[2,3-d]pyrimidine;

with 4-chloro-2-(pyridin-2-yl)-5,6-cyclopentenothieno[2,3-d]pyrimidine, 2-(pyridin-2-yl)-4-(3-chloro-4-methoxybenzylamino)-5,6-cyclopentenothieno[2,3-d]pyrimidine;

with 4-chloro-2-(pyridin-2-yl)-5,6-cycloheptenothieno[2,3-d]-pyrimidine, 2-(pyridin-2-yl)-4-(3-chloro-4-methoxybenzylamino)-5,6-cycloheptenothieno[2,3-d]pyrimidine;

with 4-chloro-2-(pyridin-2-yl)-6-ethylthieno[2,3-d]pyrimidine, 2-(pyridin-2-yl)-4-(3-chloro-4-methoxybenzylamino)-6-ethylthieno[2,3-d]pyrimidine;

with 4-chloro-2-(pyridin-2-yl)-6-chlorothieno[2,3-d]pyrimidine, 2-(pyridin-2-yl)-4-(3-chloro-4-methoxybenzylamino)-6-chlorothieno[2,3-d]pyrimidine;

with 4-chloro-2-(pyridin-2-yl)-5-chloro-6-methylthieno[2,3-d]pyrimidine, 2-(pyridin-2-yl)-4-(3-chloro-4-methoxybenzylamino)-5-chloro-6-methylthieno[2,3-d]pyrimidine;

with 4-chloro-2-(pyridin-2-yl)-6-nitrothieno[2,3-d]pyrimidine, 2-(pyridin-2-yl)-4-(3-chloro-4-methoxybenzylamino)-6-nitrothieno[2,3-d]pyrimidine;

with 4-chloro-2-(pyridin-2-yl)-5,6-dimethylthieno[2,3-d]pyrimidine, 2-(pyridin-2-yl)-4-(3-chloro-4-methoxybenzylamino)-5,6-dimethylthieno[2,3-d]pyrimidine;

with 4-chloro-2-(pyridin-2-yl)-6-trifluoromethylthieno[2,3-d]pyrimidine, 2-(pyridin-2-yl)-4-(3-chloro-4-methoxybenzylamino)-6-trifluoromethylthieno[2,3-d]pyrimidine;

with 4-chloro-2-(pyridin-4-yl)-6-methylthieno[2,3-d]pyrimidine, 2-(pyridin-4-yl)-4-(3-chloro-4-methoxybenzylamino)-6-methylthieno[2,3-d]pyrimidine;

with 4-chloro-2-(pyridin-4-yl)-5-methylthieno[2,3-d]pyrimidine, 2-(pyridin-4-yl)-4-(3-chloro-4-methoxybenzylamino)-5-methylthieno[2,3-d]pyrimidine;

with 4-chloro-2-(pyridin-4-yl)-5,6,7,8-tetrahydro[1]benzothieno[2,3-d]-pyrimidine, 2-(pyridin-4-yl)-4-(3-chloro-4-methoxybenzylamino)-5,6,7,8-tetrahydro[1]benzothieno[2,3-d]pyrimidine;

with 4-chloro-2-(pyridin-4-yl)-5,6-cyclopentenothieno[2,3-d]-pyrimidine, 2-(pyridin-4-yl)-4-(3-chloro-4-methoxybenzylamino)-5,6-cyclopentenothieno[2,3-d]pyrimidine;

with 4-chloro-2-(pyridin-4-yl)-5,6-cycloheptenothieno[2,3-d]pyrimidine, 2-(pyridin-4-yl)-4-(3-chloro-4-methoxybenzylamino)-5,6-cycloheptenothieno[2,3-d]pyrimidine;

with 4-chloro-2-(pyridin-4-yl)-6-ethylthieno[2,3-d]pyrimidine, 2-(pyridin-4-yl)-4-(3-chloro-4-methoxybenzylamino)-6-ethylthieno[2,3-d]pyrimidine;

with 4-chloro-2-(pyridin-4-yl)-6-chlorothieno[2,3-d]pyrimidine, 2-(pyridin-4-yl)-4-(3-chloro-4-methoxybenzylamino)-6-chlorothieno[2,3-d]pyrimidine;

with 4-chloro-2-(pyridin-4-yl)-5-chloro-6-methylthieno[2,3-d]pyrimidine, 2-(pyridin-4-yl)-4-(3-chloro-4-methoxybenzylamino)-5-chloro-6-methylthieno[2,3-d]pyrimidine;

with 4-chloro-2-(pyridin-4-yl)-6-nitrothieno[2,3-d]pyrimidine, 2-(pyridin-4-yl)-4-(3-chloro-4-methoxybenzylamino)-6-nitrothieno[2,3-d]pyrimidine;

with 4-chloro-2-(pyridin-4-yl)-5,6-dimethylthieno[2,3-d]pyrimidine, 2-(pyridin-4-yl)-4-(3-chloro-4-methoxybenzylamino)-5,6-dimethylthieno[2,3-d]pyrimidine;

with 4-chloro-2-(pyridin-4-yl)-6-trifluoromethylthieno[2,3-d]pyrimidine, 2-(pyridin-4-yl)-4-(3-chloro-4-methoxybenzylamino)-6-trifluoromethylthieno[2,3-d]pyrimidine.

The following are obtained analogously by reaction of 3,4-dimethoxybenzylamine:

with 4-chloro-2-(pyridin-3-yl)-6-methylthieno[2,3-d]pyrimidine, 2-(pyridin-3-yl)-4-(3,4-dimethoxybenzylamino)-6-methylthieno[2,3-d]pyrimidine;

with 4-chloro-2-(pyridin-3-yl)-5-methylthieno[2,3-d]pyrimidine, 2-(pyridin-3-yl)-4-(3,4-dimethoxybenzylamino)-5-methylthieno[2,3-d]pyrimidine;

with 4-chloro-2-(pyridin-3-yl)-5,6,7,8-tetrahydro[1]benzothieno[2,3-d]pyrimidine, 2-(pyridin-3-yl)-4-(3,4-dimethoxybenzylamino)-5,6,7,8-tetrahydro[1]benzothieno[2,3-d]pyrimidine;

with 4-chloro-2-(pyridin-3-yl)-5,6-cyclopentenothieno[2,3-d]pyrimidine, 2-(pyridin-3-yl)-4-(3,4-dimethoxybenzylamino)-5,6-cyclopentenothieno[2,3-d]pyrimidine;

with 4-chloro-2-(pyridin-3-yl)-5,6-cycloheptenothieno[2,3-d]pyrimidine, 2-(pyridin-3-yl)-4-(3,4-dimethoxybenzylamino)-5,6-cycloheptenothieno[2,3-d]pyrimidine;

with 4-chloro-2-(pyridin-3-yl)-6-ethylthieno[2,3-d]pyrimidine, 2-(pyridin-3-yl)-4-(3,4-dimethoxybenzylamino)-6-ethylthieno[2,3-d]pyrimidine;

with 4-chloro-2-(pyridin-3-yl)-6-chlorothieno[2,3-d]pyrimidine, 2-(pyridin-3-yl)-4-(3,4-dimethoxybenzylamino)-6-chlorothieno[2,3-d]pyrimidine;

with 4-chloro-2-(pyridin-3-yl)-5-chloro-6-methylthieno[2,3-d]pyrimidine, 2-(pyridin-3-yl)-4-(3,4-dimethoxybenzylamino)-5-chloro-6-methylthieno[2,3-d]pyrimidine;

with 4-chloro-2-(pyridin-3-yl)-6-nitrothieno[2,3-d]pyrimidine, 2-(pyridin-3-yl)-4-(3,4-dimethoxybenzylamino)-6-nitrothieno[2,3-d]pyrimidine;

with 4-chloro-2-(pyridin-3-yl)-5,6-dimethylthieno[2,3-d]pyrimidine, 2-(pyridin-3-yl)-4-(3,4-dimethoxybenzylamino)-5,6-dimethylthieno[2,3-d]pyrimidine;

with 4-chloro-2-(pyridin-3-yl)-6-trifluoromethylthieno[2,3-d]pyrimidine, 2-(pyridin-3-yl)-4-(3,4-dimethoxybenzylamino)-6-trifluoromethylthieno[2,3-d]pyrimidine;

with 4-chloro-2-(isoxazol-5-yl)-6-methylthieno[2,3-d]pyrimidine, 2-(isoxazol-5-yl)-4-(3,4-dimethoxybenzylamino)-6-methylthieno[2,3-d]pyrimidine;

with 4-chloro-2-(isoxazol-5-yl)-5-methylthieno[2,3-d]pyrimidine, 2-(isoxazol-5-yl)-4-(3,4-dimethoxybenzylamino)-5-methylthieno[2,3-d]pyrimidine;

with 4-chloro-2-(isoxazol-5-yl)-5,6,7,8-tetrahydro[1]benzothieno[2,3-d]-pyrimidine, 2-(isoxazol-5-yl)-4-(3,4-dimethoxybenzylamino)-5,6,7,8-tetrahydro[1]benzothieno[2,3-d]pyrimidine;

with 4-chloro-2-(isoxazol-5-yl)-5,6-cyclopentenothieno[2,3-d]-pyrimidine, 2-(isoxazol-5-yl)-4-(3,4-dimethoxybenzylamino)-5,6-cyclopentenothieno[2,3-d]pyrimidine;

with 4-chloro-2-(isoxazol-5-yl)-5,6-cycloheptenothieno[2,3-d]-pyrimidine, 2-(isoxazol-5-yl)-4-(3,4-dimethoxybenzylamino)-5,6-cycloheptenothieno[2,3-d]pyrimidine;

with 4-chloro-2-(isoxazol-5-yl)-6-ethylthieno[2,3-d]pyrimidine, 2-(isoxazol-5-yl)-4-(3,4-dimethoxybenzylamino)-6-ethylthieno[2,3-d]pyrimidine;

with 4-chloro-2-(isoxazol-5-yl)-6-chlorothieno[2,3-d]
pyrimidine, 2-(isoxazol-5-yl)-4-(3,4-
dimethoxybenzylamino)-6-chlorothieno[2,3-d]
pyrimidine;

with 4-chloro-2-(isoxazol-5-yl)-5-chloro-6-methylthieno[2,
3-d]pyrimidine, 2-(isoxazol-5-yl)-4-(3,4-
dimethoxybenzylamino)-5-chloro-6-methylthieno[2,3-d]
pyrimidine;

with 4-chloro-2-(isoxazol-5-yl)-6-nitrothieno[2,3-d]
pyrimidine, 2-(isoxazol-5-yl)-4-(3,4-
dimethoxybenzylamino)-6-nitrothieno[2,3-d]pyrimidine;

with 4-chloro-2-(isoxazol-5-yl)-5,6-dimethylthieno[2,3-d]
pyrimidine, 2-(isoxazol-5-yl)-4-(3,4-
dimethoxybenzylamino)-5,6-dimethylthieno[2,3-d]
pyrimidine;

with 4-chloro-2-(isoxazol-5-yl)-6-trifluoromethylthieno[2,
3-d]pyrimidine, 2-(isoxazol-5-yl)-4-(3,4-
dimethoxybenzylamino)-6-trifluoromethylthieno[2,3-d]
pyrimidine;

with 4-chloro-2-(pyrazin-2-yl)-6-methylthieno[2,3-d]
pyrimidine, 2-(pyrazin-2-yl)-4-(3,4-
dimethoxybenzylamino)-6-methylthieno[2,3-d]
pyrimidine;

with 4-chloro-2-(pyrazin-2-yl)-5-methylthieno[2,3-d]
pyrimidine, 2-(pyrazin-2-yl)-4-(3,4-
dimethoxybenzylamino)-5-methylthieno[2,3-d]
pyrimidine;

with 4-chloro-2-(pyrazin-2-yl)-5,6,7,8-tetrahydro[1]
benzothieno[2,3-d]pyrimidine, 2-(pyrazin-2-yl)-4-(3,4-
dimethoxybenzylamino)-5,6,7,8-tetrahydro[1]
benzothieno[2,3-d]pyrimidine;

with 4-chloro-2-(pyrazin-2-yl)-5,6-cyclopentenothieno[2,3-
d]pyrimidine, 2-(pyrazin-2-yl)-4-(3,4-
dimethoxybenzylamino)-5,6-cyclopentenothieno[2,3-d]
pyrimidine;

with 4-chloro-2-(pyrazin-2-yl)-5,6-cycloheptenothieno[2,3-
d]pyrimidine, 2-(pyrazin-2-yl)-4-(3,4-
dimethoxybenzylamino)-5,6-cycloheptenothieno[2,3-d]
pyrimidine;

with 4-chloro-2-(pyrazin-2-yl)-6-ethylthieno[2,3-d]
pyrimidine, 2-(pyrazin-2-yl)-4-(3,4-
dimethoxybenzylamino)-6-ethylthieno[2,3-d]pyrimidine;

with 4-chloro-2-(pyrazin-2-yl)-6-chlorothieno-[2,3-d]
pyrimidine, 2-(pyrazin-2-yl)-4-(3,4-
dimethoxybenzylamino)-6-chlorothieno[2,3-d]
pyrimidine;

with 4-chloro-2-(pyrazin-2-yl)-5-chloro-6-methylthieno[2,
3-d]pyrimidine, 2-(pyrazin-2-yl)-4-(3,4-
dimethoxybenzylamino)-5-chloro-6-methylthieno[2,3-d]
pyrimidine;

with 4-chloro-2-(pyrazin-2-yl)-6-nitrothieno[2,3-d]
pyrimidine, 2-(pyrazin-2-yl)-4-(3,4-
dimethoxybenzylamino)-6-nitrothieno[2,3-d]pyrimidine;

with 4-chloro-2-(pyrazin-2-yl)-5,6-dimethylthieno[2,3-d]
pyrimidine, 2-(pyrazin-2-yl)-4-(3,4-
dimethoxybenzylamino)-5,6-dimethylthieno[2,3-d]
pyrimidine;

with 4-chloro-2-(pyrazin-2-yl)-6-trifluoromethylthieno[2,3-
d]pyrimidine, 2-(pyrazin-2-yl)-4-(3,4-
dimethoxybenzylamino)-6-trifluoromethylthieno[2,3-d]
pyrimidine;

with 4-chloro-2-(pyridin-2-yl)-6-methylthieno[2,3-d]
pyrimidine, 2-(pyridin-2-yl)-4-(3,4-
dimethoxybenzylamino)-6-methylthieno[2,3-d]
pyrimidine;

with 4-chloro-2-(pyridin-2-yl)-5-methylthieno[2,3-d]
pyrimidine, 2-(pyridin-2-yl)-4-(3,4-
dimethoxybenzylamino)-5-methylthieno[2,3-d]
pyrimidine with 4-chloro-2-(pyridin-2-yl)-5,6,7,8-tetrahydro[1]
benzothieno[2,3-d]pyrimidine, 2-(pyridin-2-yl)-4-(3,4-
dimethoxybenzylamino)-5,6,7,8-tetrahydro[1]
benzothieno[2,3-d]pyrimidine;

with 4-chloro-2-(pyridin-2-yl)-5,6-cyclopentenothieno[2,3-
d]pyrimidine, 2-(pyridin-2-yl)-4-(3,4-
dimethoxybenzylamino)-5,6-cyclopentenothieno[2,3-d]
pyrimidine;

with 4-chloro-2-(pyridin-2-yl)-5,6-cycloheptenothieno[2,3-
d]pyrimidine, 2-(pyridin-2-yl)-4-(3,4-
dimethoxybenzylamino)-5,6-cycloheptenothieno[2,3-d]
pyrimidine;

with 4-chloro-2-(pyridin-2-yl)-6-ethylthieno[2,3-d]
pyrimidine, 2-(pyridin-2-yl)-4-(3,4-
dimethoxybenzylamino)-6-ethylthieno[2,3-d]pyrimidine;

with 4-chloro-2-(pyridin-2-yl)-6-chlorothieno-[2,3-d]
pyrimidine, 2-(pyridin-2-yl)-4-(3,4-
dimethoxybenzylamino)-6-chlorothieno[2,3-d]
pyrimidine;

with 4-chloro-2-(pyridin-2-yl)-5-chloro-6-methylthieno[2,
3-d]pyrimidine, 2-(pyridin-2-yl)-4-(3,4-
dimethoxybenzylamino)-5-chloro-6-methylthieno[2,3-d]
pyrimidine;

with 4-chloro-2-(pyridin-2-yl)-6-nitrothieno-[2,3-d]
pyrimidine, 2-(pyridin-2-yl)-4-(3,4-
dimethoxybenzylamino)-6-nitrothieno[2,3-d]pyrimidine;

with 4-chloro-2-(pyridin-2-yl)-5,6-dimethylthieno[2,3-d]
pyrimidine, 2-(pyridin-2-yl)-4-(3,4-
dimethoxybenzylamino)-5,6-dimethylthieno[2,3-d]
pyrimidine;

with 4-chloro-2-(pyridin-2-yl)-6-trifluoromethylthieno[2,3-
d]pyrimidine, 2-(pyridin-2-yl)-4-(3,4-
dimethoxybenzylamino)-6-trifluoromethylthieno[2,3-d]
pyrimidine;

with 4-chloro-2-(pyridin-4-yl)-6-methylthieno[2,3-d]
pyrimidine, 2-(pyridin-4-yl)-4-(3,4-
dimethoxybenzylamino)-6-methylthieno[2,3-d]
pyrimidine;

with 4-chloro-2-(pyridin-4-yl)-5-methylthieno[2,3-d]
pyrimidine, 2-(pyridin-4-yl)-4-(3,4-
dimethoxybenzylamino)-5-methylthieno[2,3-d]
pyrimidine;

with 4-chloro-2-(pyridin-4-yl)-5,6,7,8-tetrahydro[1]
benzothieno[2,3-d]-pyrimidine, 2-(pyridin-4-yl)-4-(3,4-
dimethoxybenzylamino)-5,6,7,8-tetrahydro[1]
benzothieno[2,3-d]pyrimidine;

with 4-chloro-2-(pyridin-4-yl)-5,6-cyclopentenothieno[2,3-
d]pyrimidine, 2-(pyridin-4-yl)-4-(3,4-
dimethoxybenzylamino)-5,6-cyclopentenothieno[2,3-d]
pyrimidine;

with 4-chloro-2-(pyridin-4-yl)-5,6-cycloheptenothieno[2,3-
d]pyrimidine, 2-(pyridin-4-yl)-4-(3,4-
dimethoxybenzylamino)-5,6-cycloheptenothieno[2,3-d]
pyrimidine;

with 4-chloro-2-(pyridin-4-yl)-6-ethylthieno[2,3-d]
pyrimidine, 2-(pyridin-4-yl)-4-(3,4-
dimethoxybenzylamino)-6-ethylthieno[2,3-d]pyrimidine;

with 4-chloro-2-(pyridin-4-yl)-6-chlorothieno[2,3-d]
pyrimidine, 2-(pyridin-4-yl)-4-(3,4-
dimethoxybenzylamino)-6-chlorothieno[2,3-d]
pyrimidine;

with 4-chloro-2-(pyridin-4-yl)-5-chloro-6-methylthieno[2,
3-d]pyrimidine, 2-(pyridin-4-yl)-4-(3,4-
dimethoxybenzylamino)-5-chloro-6-methylthieno[2,3-d]
pyrimidine;

with 4-chloro-2-(pyridin-4-yl)-6-nitrothieno[2,3-d]
pyrimidine, 2-(pyridin-4-yl)-4-(3,4-
dimethoxybenzylamino)-6-nitrothieno[2,3-d]pyrimidine;

with 4-chloro-2-(pyridin-4-yl)-5,6-dimethylthieno[2,3-d]pyrimidine, 2-(pyridin-4-yl)-4-(3,4-dimethoxybenzylamino)-5,6-dimethylthieno[2,3-d]pyrimidine;

with 4-chloro-2-(pyridin-4-yl)-6-trifluoromethylthieno[2,3-d]pyrimidine, 2-(pyridin-4-yl)-4-(3,4-dimethoxybenzylamino)-6-trifluoromethylthieno[2,3-d]pyrimidine;

The following are obtained analogously by reaction of benzylamine:

with 4-chloro-2-(pyridin-3-yl)-6-methylthieno[2,3-d]pyrimidine, 2-(pyridin-3-yl)-4-benzylamino-6-methylthieno[2,3-d]pyrimidine;

with 4-chloro-2-(pyridin-3-yl)-5-methylthieno[2,3-d]pyrimidine, 2-(pyridin-3-yl)-4-benzylamino-5-methylthieno[2,3-d]pyrimidine;

with 4-chloro-2-(pyridin-3-yl)-5,6,7,8-tetrahydro[1]benzothieno[2,3-d]pyrimidine, 2-(pyridin-3-yl)-4-benzylamino-5,6,7,8-tetrahydro[1]benzothieno[2,3-d]pyrimidine, m.p. 189°;

with 4-chloro-2-(pyridin-3-yl)-5,6-cyclopentenothieno[2,3-d]pyrimidine, 2-(pyridin-3-yl)-4-benzylamino-5,6-cyclopentenothieno[2,3-d]pyrimidine;

with 4-chloro-2-(pyridin-3-yl)-5,6-cycloheptenothieno[2,3-d]pyrimidine, 2-(pyridin-3-yl)-4-benzylamino-5,6-cycloheptenothieno[2,3-d]pyrimidine;

with 4-chloro-2-(pyridin-3-yl)-6-ethylthieno[2,3-d]pyrimidine, 2-(pyridin-3-yl)-4-benzylamino-6-ethylthieno[2,3-d]pyrimidine;

with 4-chloro-2-(pyridin-3-yl)-6-chlorothieno[2,3-d]pyrimidine, 2-(pyridin-3-yl)-4-benzylamino-6-chlorothieno[2,3-d]pyrimidine;

with 4-chloro-2-(pyridin-3-yl)-5-chloro-6-methylthieno[2,3-d]pyrimidine, 2-(pyridin-3-yl)-4-benzylamino-5-chloro-6-methylthieno[2,3-d]pyrimidine;

with 4-chloro-2-(pyridin-3-yl)-6-nitrothieno[2,3-d]pyrimidine, 2-(pyridin-3-yl)-4-benzylamino-6-nitrothieno[2,3-d]pyrimidine;

with 4-chloro-2-(pyridin-3-yl)-5,6-dimethylthieno[2,3-d]pyrimidine, 2-(pyridin-3-yl)-4-benzylamino-5,6-dimethylthieno[2,3-d]pyrimidine;

with 4-chloro-2-(pyridin-3-yl)-6-trifluoromethylthieno[2,3-d]pyrimidine, 2-(pyridin-3-yl)-4-benzylamino-6-trifluoromethylthieno[2,3-d]pyrimidine;

with 4-chloro-2-(isoxazol-5-yl)-6-methylthieno[2,3-d]pyrimidine, 2-(isoxazol-5-yl)-4-benzylamino-6-methylthieno[2,3-d]pyrimidine;

with 4-chloro-2-(isoxazol-5-yl)-5-methylthieno[2,3-d]pyrimidine, 2-(isoxazol-5-yl)-4-benzylamino-5-methylthieno[2,3-d]pyrimidine;

with 4-chloro-2-(isoxazol-5-yl)-5,6,7,8-tetrahydro[1]benzothieno[2,3-d]pyrimidine, 2-(isoxazol-5-yl)-4-benzylamino-5,6,7,8-tetrahydro[1]benzothieno[2,3-d]pyrimidine;

with 4-chloro-2-(isoxazol-5-yl)-5,6-cyclopentenothieno[2,3-d]pyrimidine, 2-(isoxazol-5-yl)-4-benzylamino-5,6-cyclopentenothieno[2,3-d]pyrimidine;

with 4-chloro-2-(isoxazol-5-yl)-5,6-cycloheptenothieno[2,3-d]pyrimidine, 2-(isoxazol-5-yl)-4-benzylamino-5,6-cycloheptenothieno[2,3-d]pyrimidine;

with 4-chloro-2-(isoxazol-5-yl)-6-ethylthieno[2,3-d]pyrimidine, 2-(isoxazol-5-yl)-4-benzylamino-6-ethylthieno[2,3-d]pyrimidine;

with 4-chloro-2-(isoxazol-5-yl)-6-chlorothieno[2,3-d]pyrimidine, 2-(isoxazol-5-yl)-4-benzylamino-6-chlorothieno[2,3-d]pyrimidine;

with 4-chloro-2-(isoxazol-5-yl)-5-chloro-6-methylthieno[2,3-d]pyrimidine, 2-(isoxazol-5-yl)-4-benzylamino-5-chloro-6-methylthieno[2,3-d]pyrimidine;

with 4-chloro-2-(isoxazol-5-yl)-6-nitrothieno[2,3-d]pyrimidine, 2-(isoxazol-5-yl)-4-benzylamino-6-nitrothieno[2,3-d]pyrimidine;

with 4-chloro-2-(isoxazol-5-yl)-5,6-dimethylthieno[2,3-d]pyrimidine, 2-(isoxazol-5-yl)-4-benzylamino-5,6-dimethylthieno[2,3-d]pyrimidine;

with 4-chloro-2-(isoxazol-5-yl)-6-trifluoromethylthieno[2,3-d]pyrimidine, 2-(isoxazol-5-yl)-4-benzylamino-6-trifluoromethylthieno[2,3-d]pyrimidine;

with 4-chloro-2-(pyrazin-2-yl)-6-methylthieno[2,3-d]pyrimidine, 2-(pyrazin-2-yl)-4-benzylamino-6-methylthieno[2,3-d]pyrimidine;

with 4-chloro-2-(pyrazin-2-yl)-5-methylthieno[2,3-d]pyrimidine, 2-(pyrazin-2-yl)-4-benzylamino-5-methylthieno[2,3-d]pyrimidine;

with 4-chloro-2-(pyrazin-2-yl)-5,6,7,8-tetrahydro[1]benzothieno[2,3-d]pyrimidine, 2-(pyrazin-2-yl)-4-benzylamino-5,6,7,8-tetrahydro[1]benzothieno[2,3-d]pyrimidine;

with 4-chloro-2-(pyrazin-2-yl)-5,6-cyclopentenothieno[2,3-d]pyrimidine, 2-(pyrazin-2-yl)-4-benzylamino-5,6-cyclopentenothieno[2,3-d]pyrimidine;

with 4-chloro-2-(pyrazin-2-yl)-5,6-cycloheptenothieno[2,3-d]pyrimidine, 2-(pyrazin-2-yl)-4-benzylamino-5,6-cycloheptenothieno[2,3-d]pyrimidine;

with 4-chloro-2-(pyrazin-2-yl)-6-ethylthieno[2,3-d]pyrimidine, 2-(pyrazin-2-yl)-4-benzylamino-6-ethylthieno[2,3-d]pyrimidine;

with 4-chloro-2-(pyrazin-2-yl)-6-chlorothieno[2,3-d]pyrimidine, 2-(pyrazin-2-yl)-4-benzylamino-6-chlorothieno[2,3-d]pyrimidine;

with 4-chloro-2-(pyrazin-2-yl)-5-chloro-6-methylthieno[2,3-d]pyrimidine, 2-(pyrazin-2-yl)-4-benzylamino-5-chloro-6-methylthieno[2,3-d]pyrimidine;

with 4-chloro-2-(pyrazin-2-yl)-6-nitrothieno[2,3-d]pyrimidine, 2-(pyrazin-2-yl)-4-benzylamino-6-nitrothieno[2,3-d]pyrimidine;

with 4-chloro-2-(pyrazin-2-yl)-5,6-dimethylthieno[2,3-d]pyrimidine, 2-(pyrazin-2-yl)-4-benzylamino-5,6-dimethylthieno[2,3-d]pyrimidine;

with 4-chloro-2-(pyrazin-2-yl)-6-trifluoromethylthieno[2,3-d]pyrimidine, 2-(pyrazin-2-yl)-4-benzylamino-6-trifluoromethylthieno[2,3-d]pyrimidine;

with 4-chloro-2-(pyridin-2-yl)-6-methylthieno[2,3-d]pyrimidine, 2-(pyridin-2-yl)-4-benzylamino-6-methylthieno[2,3-d]pyrimidine;

with 4-chloro-2-(pyridin-2-yl)-5-methylthieno[2,3-d]pyrimidine, 2-(pyridin-2-yl)-4-benzylamino-5-methylthieno[2,3-d]pyrimidine;

with 4-chloro-2-(pyridin-2-yl)-5,6,7,8-tetrahydro[1]benzothieno[2,3-d]pyrimidine, 2-(pyridin-2-yl)-4-benzylamino-5,6,7,8-tetrahydro[1]benzothieno[2,3-d]pyrimidine;

with 4-chloro-2-(pyridin-2-yl)-5,6-cyclopentenothieno[2,3-d]pyrimidine, 2-(pyridin-2-yl)-4-benzylamino-5,6-cyclopentenothieno[2,3-d]pyrimidine;

with 4-chloro-2-(pyridin-2-yl)-5,6-cycloheptenothieno[2,3-d]pyrimidine, 2-(pyridin-2-yl)-4-benzylamino-5,6-cycloheptenothieno[2,3-d]pyrimidine;

with 4-chloro-2-(pyridin-2-yl)-6-ethylthieno[2,3-d]pyrimidine, 2-(pyridin-2-yl)-4-benzylamino-6-ethylthieno[2,3-d]pyrimidine;

with 4-chloro-2-(pyridin-2-yl)-6-chlorothieno[2,3-d]pyrimidine, 2-(pyridin-2-yl)-4-benzylamino-6-chlorothieno[2,3-d]pyrimidine;

with 4-chloro-2-(pyridin-2-yl)-5-chloro-6-methylthieno[2,3-d]pyrimidine, 2-(pyridin-2-yl)-4-benzylamino-5-chloro-6-methylthieno[2,3-d]pyrimidine;

with 4-chloro-2-(pyridin-2-yl)-6-nitrothieno[2,3-d]pyrimidine, 2-(pyridin-2-yl)-4-benzylamino-6-nitrothieno[2,3-d]pyrimidine;

with 4-chloro-2-(pyridin-2-yl)-5,6-dimethylthieno[2,3-d]pyrimidine, 2-(pyridin-2-yl)-4-benzylamino-5,6-dimethylthieno[2,3-d]pyrimidine;

with 4-chloro-2-(pyridin-2-yl)-6-trifluoromethylthieno[2,3-d]pyrimidine, 2-(pyridin-2-yl)-4-benzylamino-6-trifluoromethylthieno[2,3-d]pyrimidine;

with 4-chloro-2-(pyridin-4-yl)-6-methylthieno[2,3-d]pyrimidine, 2-(pyridin-4-yl)-4-benzylamino-6-methylthieno[2,3-d]pyrimidine;

with 4-chloro-2-(pyridin-4-yl)-5-methylthieno[2,3-d]pyrimidine, 2-(pyridin-4-yl)-4-benzylamino-5-methylthieno[2,3-d]pyrimidine;

with 4-chloro-2-(pyridin-4-yl)-5,6,7,8-tetrahydro[1]benzothieno[2,3-d]pyrimidine, 2-(pyridin-4-yl)-4-benzylamino-5,6,7,8-tetrahydro[1]benzothieno[2,3-d]pyrimidine;

with 4-chloro-2-(pyridin-4-yl)-5,6-cyclopentenothieno[2,3-d]pyrimidine, 2-(pyridin-4-yl)-4-benzylamino-5,6-cyclopentenothieno[2,3-d]pyrimidine;

with 4-chloro-2-(pyridin-4-yl)-5,6-cycloheptenothieno[2,3-d]pyrimidine, 2-(pyridin-4-yl)-4-benzylamino-5,6-cycloheptenothieno[2,3-d]pyrimidine;

with 4-chloro-2-(pyridin-4-yl)-6-ethylthieno[2,3-d]pyrimidine, 2-(pyridin-4-yl)-4-benzylamino-6-ethylthieno[2,3-d]pyrimidine;

with 4-chloro-2-(pyridin-4-yl)-6-chlorothieno[2,3-d]pyrimidine, 2-(pyridin-4-yl)-4-benzylamino-6-chlorothieno[2,3-d]pyrimidine;

with 4-chloro-2-(pyridin-4-yl)-5-chloro-6-methylthieno[2,3-d]pyrimidine, 2-(pyridin-4-yl)-4-benzylamino-5-chloro-6-methylthieno[2,3-d]pyrimidine;

with 4-chloro-2-(pyridin-4-yl)-6-nitrothieno[2,3-d]pyrimidine, 2-(pyridin-4-yl)-4-benzylamino-6-nitrothieno[2,3-d]pyrimidine;

with 4-chloro-2-(pyridin-4-yl)-5,6-dimethylthieno[2,3-d]pyrimidine, 2-(pyridin-4-yl)-4-benzylamino-5,6-dimethylthieno[2,3-d]pyrimidine;

with 4-chloro-2-(pyridin-4-yl)-6-trifluoromethylthieno[2,3-d]pyrimidine, 2-(pyridin-4-yl)-4-benzylamino-6-trifluoromethylthieno[2,3-d]pyrimidine.

The following are obtained analogously by reaction of 4-fluorobenzylamine:

with 4-chloro-2-(pyridin-3-yl)-6-methylthieno[2,3-d]pyrimidine, 2-(pyridin-3-yl)-4-(4-fluorobenzylamino)-6-methylthieno[2,3-d]pyrimidine;

with 4-chloro-2-(pyridin-3-yl)-5-methylthieno[2,3-d]pyrimidine, 2-(pyridin-3-yl)-4-(4-fluorobenzylamino)-5-methylthieno[2,3-d]pyrimidine;

with 4-chloro-2-(pyridin-3-yl)-5,6,7,8-tetrahydro[1]benzothieno[2,3-d]pyrimidine, 2-(pyridin-3-yl)-4-(4-fluorobenzylamino)-5,6,7,8-tetrahydro[1]benzothieno[2,3-d]pyrimidine;

with 4-chloro-2-(pyridin-3-yl)-5,6-cyclopentenothieno[2,3-d]pyrimidine, 2-(pyridin-3-yl)-4-(4-fluorobenzylamino)-5,6-cyclopentenothieno[2,3-d]pyrimidine;

with 4-chloro-2-(pyridin-3-yl)-5,6-cycloheptenothieno[2,3-d]pyrimidine, 2-(pyridin-3-yl)-4-(4-fluorobenzylamino)-5,6-cycloheptenothieno[2,3-d]pyrimidine;

with 4-chloro-2-(pyridin-3-yl)-6-ethylthieno[2,3-d]pyrimidine, 2-(pyridin-3-yl)-4-(4-fluorobenzylamino)-6-ethylthieno[2,3-d]pyrimidine;

with 4-chloro-2-(pyridin-3-yl)-6-chlorothieno[2,3-d]pyrimidine, 2-(pyridin-3-yl)-4-(4-fluorobenzylamino)-6-chlorothieno[2,3-d]pyrimidine;

with 4-chloro-2-(pyridin-3-yl)-5-chloro-6-methylthieno[2,3-d]pyrimidine, 2-(pyridin-3-yl)-4-(4-fluorobenzylamino)-5-chloro-6-methylthieno[2,3-d]pyrimidine;

with 4-chloro-2-(pyridin-3-yl)-6-nitrothieno[2,3-d]pyrimidine, 2-(pyridin-3-yl)-4-(4-fluorobenzylamino)-6-nitrothieno[2,3-d]pyrimidine;

with 4-chloro-2-(pyridin-3-yl)-5,6-dimethylthieno[2,3-d]pyrimidine, 2-(pyridin-3-yl)-4-(4-fluorobenzylamino)-5,6-dimethylthieno[2,3-d]pyrimidine;

with 4-chloro-2-(pyridin-3-yl)-6-trifluoromethylthieno[2,3-d]pyrimidine, 2-(pyridin-3-yl)-4-(4-fluorobenzylamino)-6-trifluoromethylthieno[2,3-d]pyrimidine;

with 4-chloro-2-(isoxazol-5-yl)-6-methylthieno[2,3-d]pyrimidine, 2-(isoxazol-5-yl)-4-(4-fluorobenzylamino)-6-methylthieno[2,3-d]pyrimidine;

with 4-chloro-2-(isoxazol-5-yl)-5-methylthieno[2,3-d]pyrimidine, 2-(isoxazol-5-yl)-4-(4-fluorobenzylamino)-5-methylthieno[2,3-d]pyrimidine;

with 4-chloro-2-(isoxazol-5-yl)-5,6,7,8-tetrahydro[1]benzothieno[2,3-d]pyrimidine, 2-(isoxazol-5-yl)-4-(4-fluorobenzylamino)-5,6,7,8-tetrahydro[1]benzothieno[2,3-d]pyrimidine;

with 4-chloro-2-(isoxazol-5-yl)-5,6-cyclopentenothieno[2,3-d]pyrimidine, 2-(isoxazol-5-yl)-4-(4-fluorobenzylamino)-5,6-cyclopentenothieno[2,3-d]pyrimidine;

with 4-chloro-2-(isoxazol-5-yl)-5,6-cycloheptenothieno[2,3-d]pyrimidine, 2-(isoxazol-5-yl)-4-(4-fluorobenzylamino)-5,6-cycloheptenothieno[2,3-d]pyrimidine;

with 4-chloro-2-(isoxazol-5-yl)-6-ethylthieno[2,3-d]pyrimidine, 2-(isoxazol-5-yl)-4-(4-fluorobenzylamino)-6-ethylthieno[2,3-d]pyrimidine;

with 4-chloro-2-(isoxazol-5-yl)-6-chlorothieno[2,3-d]pyrimidine, 2-(isoxazol-5-yl)-4-(4-fluorobenzylamino)-6-chlorothieno[2,3-d]pyrimidine;

with 4-chloro-2-(isoxazol-5-yl)-5-chloro-6-methylthieno[2,3-d]pyrimidine, 2-(isoxazol-5-yl)-4-(4-fluorobenzylamino)-5-chloro-6-methylthieno[2,3-d]pyrimidine;

with 4-chloro-2-(isoxazol-5-yl)-6-nitrothieno[2,3-d]pyrimidine, 2-(isoxazol-5-yl)-4-(4-fluorobenzylamino)-6-nitrothieno[2,3-d]pyrimidine;

with 4-chloro-2-(isoxazol-5-yl)-5,6-dimethylthieno[2,3-d]pyrimidine, 2-(isoxazol-5-yl)-4-(4-fluorobenzylamino)-5,6-dimethylthieno[2,3-d]pyrimidine;

with 4-chloro-2-(isoxazol-5-yl)-6-trifluoromethylthieno[2,3-d]pyrimidine, 2-(isoxazol-5-yl)-4-(4-fluorobenzylamino)-6-trifluoromethylthieno[2,3-d]pyrimidine;

with 4-chloro-2-(pyrazin-2-yl)-6-methylthieno[2,3-d]pyrimidine, 2-(pyrazin-2-yl)-4-(4-fluorobenzylamino)-6-methylthieno[2,3-d]pyrimidine;

with 4-chloro-2-(pyrazin-2-yl)-5-methylthieno[2,3-d]pyrimidine, 2-(pyrazin-2-yl)-4-(4-fluorobenzylamino)-5-methylthieno[2,3-d]pyrimidine;

with 4-chloro-2-(pyrazin-2-yl)-5,6,7,8-tetrahydro[1]benzothieno[2,3-d]pyrimidine, 2-(pyrazin-2-yl)-4-(4-fluorobenzylamino)-5,6,7,8-tetrahydro[1]benzothieno[2,3-d]pyrimidine;

with 4-chloro-2-(pyrazin-2-yl)-5,6-cyclopentenothieno[2,3-d]pyrimidine, 2-(pyrazin-2-yl)-4-(4-fluorobenzylamino)-5,6-cyclopentenothieno[2,3-d]pyrimidine;

with 4-chloro-2-(pyrazin-2-yl)-5,6-cycloheptenothieno[2,3-d]pyrimidine, 2-(pyrazin-2-yl)-4-(4-fluorobenzylamino)-5,6-cycloheptenothieno[2,3-d]pyrimidine;

with 4-chloro-2-(pyrazin-2-yl)-6-ethylthieno[2,3-d]pyrimidine, 2-(pyrazin-2-yl)-4-(4-fluorobenzylamino)-6-ethylthieno[2,3-d]pyrimidine;

with 4-chloro-2-(pyrazin-2-yl)-6-chlorothieno[2,3-d]pyrimidine, 2-(pyrazin-2-yl)-4-(4-fluorobenzylamino)-6-chlorothieno[2,3-d]pyrimidine;

with 4-chloro-2-(pyrazin-2-yl)-5-chloro-6-methylthieno[2,3-d]pyrimidine, 2-(pyrazin-2-yl)-4-(4-fluorobenzylamino)-5-chloro-6-methylthieno[2,3-d]pyrimidine;

with 4-chloro-2-(pyrazin-2-yl)-6-nitrothieno[2,3-d]pyrimidine, 2-(pyrazin-2-yl)-4-(4-fluorobenzylamino)-6-nitrothieno[2,3-d]pyrimidine;

with 4-chloro-2-(pyrazin-2-yl)-5,6-dimethylthieno[2,3-d]pyrimidine, 2-(pyrazin-2-yl)-4-(4-fluorobenzylamino)-5,6-dimethylthieno[2,3-d]pyrimidine;

with 4-chloro-2-(pyrazin-2-yl)-6-trifluoromethylthieno[2,3-d]pyrimidine, 2-(pyrazin-2-yl)-4-(4-fluorobenzylamino)-6-trifluoromethylthieno[2,3-d]pyrimidine;

with 4-chloro-2-(pyridin-2-yl)-6-methylthieno[2,3-d]pyrimidine, 2-(pyridin-2-yl)-4-(4-fluorobenzylamino)-6-methylthieno[2,3-d]pyrimidine;

with 4-chloro-2-(pyridin-2-yl)-5-methylthieno[2,3-d]pyrimidine, 2-(pyridin-2-yl)-4-(4-fluorobenzylamino)-5-methylthieno[2,3-d]pyrimidine;

with 4-chloro-2-(pyridin-2-yl)-5,6,7,8-tetrahydro[1]benzothieno[2,3-d]pyrimidine, 2-(pyridin-2-yl)-4-(4-fluorobenzylamino)-5,6,7,8-tetrahydro[1]benzothieno[2,3-d]pyrimidine;

with 4-chloro-2-(pyridin-2-yl)-5,6-cyclopentenothieno[2,3-d]pyrimidine, 2-(pyridin-2-yl)-4-(4-fluorobenzylamino)-5,6-cyclopentenothieno[2,3-d]pyrimidine;

with 4-chloro-2-(pyridin-2-yl)-5,6-cycloheptenothieno[2,3-d]pyrimidine, 2-(pyridin-2-yl)-4-(4-fluorobenzylamino)-5,6-cycloheptenothieno[2,3-d]pyrimidine;

with 4-chloro-2-(pyridin-2-yl)-6-ethylthieno[2,3-d]pyrimidine, 2-(pyridin-2-yl)-4-(4-fluorobenzylamino)-6-ethylthieno[2,3-d]pyrimidine;

with 4-chloro-2-(pyridin-2-yl)-6-chlorothieno[2,3-d]pyrimidine, 2-(pyridin-2-yl)-4-(4-fluorobenzylamino)-6-chlorothieno[2,3-d]pyrimidine;

with 4-chloro-2-(pyridin-2-yl)-5-chloro-6-methylthieno[2,3-d]pyrimidine, 2-(pyridin-2-yl)-4-(4-fluorobenzylamino)-5-chloro-6-methylthieno[2,3-d]pyrimidine;

with 4-chloro-2-(pyridin-2-yl)-6-nitrothieno[2,3-d]pyrimidine, 2-(pyridin-2-yl)-4-(4-fluorobenzylamino)-6-nitrothieno[2,3-d]pyrimidine;

with 4-chloro-2-(pyridin-2-yl)-5,6-dimethylthieno[2,3-d]pyrimidine, 2-(pyridin-2-yl)-4-(4-fluorobenzylamino)-5,6-dimethylthieno[2,3-d]pyrimidine;

with 4-chloro-2-(pyridin-2-yl)-6-trifluromethylthieno[2,3-d]pyrimidine, 2-(pyridin-2-yl)-4-(4-fluorobenzylamino)-6-trifluoromethylthieno[2,3-d]pyrimidine;

with 4-chloro-2-(pyridin-4-yl)-6-methylthieno[2,3-d]pyrimidine, 2-(pyridin-4-yl)-4-(4-fluorobenzylamino)-6-methylthieno[2,3-d]pyrimidine;

with 4-chloro-2-(pyridin-4-yl)-5-methylthieno[2,3-d]pyrimidine, 2-(pyridin-4-yl)-4-(4-fluorobenzylamino)-5-methylthieno[2,3-d]pyrimidine;

with 4-chloro-2-(pyridin-4-yl)-5,6,7,8-tetrahydro[1]benzothieno[2,3-d]pyrimidine, 2-(pyridin-4-yl)-4-(4-fluorobenzylamino)-5,6,7,8-tetrahydro[1]benzothieno[2,3-d]pyrimidine;

with 4-chloro-2-(pyridin-4-yl)-5,6-cyclopentenothieno[2,3-d]pyrimidine, 2-(pyridin-4-yl)-4-(4-fluorobenzylamino)-5,6-cyclopentenothieno[2,3-d]pyrimidine;

with 4-chloro-2-(pyridin-4-yl)-5,6-cycloheptenothieno[2,3-d]pyrimidine, 2-(pyridin-4-yl)-4-(4-fluorobenzylamino)-5,6-cycloheptenothieno[2,3-d]pyrimidine;

with 4-chloro-2-(pyridin-4-yl)-6-ethylthieno[2,3-d]pyrimidine, 2-(pyridin-4-yl)-4-(4-fluorobenzylamino)-6-ethylthieno[2,3-d]pyrimidine;

with 4-chloro-2-(pyridin-4-yl)-6-chlorothieno[2,3-d]pyrimidine, 2-(pyridin-4-yl)-4-(4-fluorobenzylamino)-6-chlorothieno[2,3-d]pyrimidine;

with 4-chloro-2-(pyridin-4-yl)-5-chloro-6-methylthieno[2,3-d]pyrimidine, 2-(pyridin-4-yl)-4-(4-fluorobenzylamino)-5-chloro-6-methylthieno[2,3-d]pyrimidine;

with 4-chloro-2-(pyridin-4-yl)-6-nitrothieno[2,3-d]pyrimidine, 2-(pyridin-4-yl)-4-(4-fluorobenzylamino)-6-nitrothieno[2,3-d]pyrimidine;

with 4-chloro-2-(pyridin-4-yl)-5,6-dimethylthieno[[2,3-d]pyrimidine, 2-(pyridin-4-yl)-4-(4-fluorobenzylamino)-5,6-dimethylthieno[2,3-d]pyrimidine;

with 4-chloro-2-(pyridin-4-yl)-6-trifluoromethylthieno[2,3-d]pyrimidine, 2-(pyridin-4-yl)-4-(4-fluorobenzylamino)-6-trifluoromethylthieno[2,3-d]pyrimidine.

The following are obtained analogously by reaction of 3,4-dichlorobenzylamine:

with 4-chloro-2-(pyridin-3-yl)-6-methylthieno[2,3-d]pyrimidine, 2-(pyridin-3-yl)-4-(3,4-dichlorobenzylamino)-6-methylthieno[2,3-d]pyrimidine;

with 4-chloro-2-(pyridin-3-yl)-5-methylthieno[2,3-d]pyrimidine, 2-(pyridin-3-yl)-4-(3,4-dichlorobenzylamino)-5-methylthieno[2,3-d]pyrimidine;

with 4-chloro-2-(pyridin-3-yl)-5,6,7,8-tetrahydro[1]benzothieno[2,3-d]pyrimidine, 2-(pyridin-3-yl)-4-(3,4-dichlorobenzylamino)-5,6,7,8-tetrahydro[1]benzothieno[2,3-d]pyrimidine;

with 4-chloro-2-(pyridin-3-yl)-5,6-cyclopentenothieno[2,3-d]pyrimidine, 2-(pyridin-3-yl)-4-(3,4-dichlorobenzylamino)-5,6-cyclopentenothieno[2,3-d]pyrimidine;

with 4-chloro-2-(pyridin-3-yl)-5,6-cycloheptenothieno[2,3-d]pyrimidine, 2-(pyridin-3-yl)-4-(3,4-dichlorobenzylamino)-5,6-cycloheptenothieno[2,3-d]pyrimidine;

with 4-chloro-2-(pyridin-3-yl)-6-ethylthieno[2,3-d]pyrimidine, 2-(pyridin-3-yl)-4-(3,4-dichlorobenzylamino)-6-ethylthieno[2,3-d]pyrimidine;

with 4-chloro-2-(pyridin-3-yl)-6-chlorothieno[2,3-d]pyrimidine, 2-(pyridin-3-yl)-4-(3,4-dichlorobenzylamino)-6-chlorothieno[2,3-d]pyrimidine;

with 4-chloro-2-(pyridin-3-yl)-5-chloro-6-methylthieno[2,3-d]pyrimidine, 2-(pyridin-3-yl)-4-(3,4-dichlorobenzylamino)-5-chloro-6-methylthieno[2,3-d]pyrimidine;

with 4-chloro-2-(pyridin-3-yl)-6-nitrothieno(2,3-d]pyrimidine, 2-(pyridin-3-yl)-4-(3,4-dichlorobenzylamino)-6-nitrothieno[2,3-d]pyrimidine;

with 4-chloro-2-(pyridin-3-yl)-5,6-dimethylthieno[2,3-d]pyrimidine, 2-(pyridin-3-yl)-4-(3,4-dichlorobenzylamino)-5,6-dimethylthieno[2,3-d]pyrimidine;

with 4-chloro-2-(pyridin-3-yl)-6-trifluoromethylthieno[2,3-d]pyrimidine, 2-(pyridin-3-yl)-4-(3,4-dichlorobenzylamino)-6-trifluoromethylthieno[2,3-d]pyrimidine;

with 4-chloro-2-(isoxazol-5-yl)-6-methylthieno[2,3-d]
pyrimidine, 2-(isoxazol-5-yl)-4-(3,4-dichlorobenzylamino)-6-methylthieno[2,3-d]pyrimidine;

with 4-chloro-2-(isoxazol-5-yl)-5-methylthieno[2,3-d]
pyrimidine, 2-(isoxazol-5-yl)-4-(3,4-dichlorobenzylamino)-5-methylthieno[2,3-d]pyrimidine;

with 4-chloro-2-(isoxazol-5-yl)-5,6,7,8-tetrahydro[1]
benzothieno[2,3-d]pyrimidine, 2-(isoxazol-5-yl)-4-(3,4-dichlorobenzylamino)-5,6,7,8-tetrahydro[1]benzothieno[2,3-d]pyrimidine;

with 4-chloro-2-(isoxazol-5-yl)-5,6-cyclopentenothieno[2,3-d]pyrimidine, 2-(isoxazol-5-yl)-4-(3,4-dichlorobenzylamino)-5,6-cyclopentenothieno[2,3-d]pyrimidine;

with 4-chloro-2-(isoxazol-5-yl)-5,6-cycloheptenothieno[2,3-d]pyrimidine, 2-(isoxazol-5-yl)-4-(3,4-dichlorobenzylamino)-5,6-cycloheptenothieno[2,3-d]pyrimidine;

with 4-chloro-2-(isoxazol-5-yl)-6-ethylthieno[2,3-d]
pyrimidine, 2-(isoxazol-5-yl)-4-(3,4-dichlorobenzylamino)-6-ethylthieno[2,3-d]pyrimidine;

with 4-chloro-2-(isoxazol-5-yl)-6-chlorothieno[2,3-d]
pyrimidine, 2-(isoxazol-5-yl)-4-(3,4-dichlorobenzylamino)-6-chlorothieno[2,3-d]pyrimidine;

with 4-chloro-2-(isoxazol-5-yl)-5-chloro-6-methylthieno[2,3-d]pyrimidine, 2-(isoxazol-5-yl)-4-(3,4-dichlorobenzylamino)-5-chloro-6-methylthieno[2,3-d]pyrimidine;

with 4-chloro-2-(isoxazol-5-yl)-6-nitrothieno[2,3-d]
pyrimidine, 2-(isoxazol-5-yl)-4-(3,4-dichlorobenzylamino)-6-nitrothieno[2,3-d]pyrimidine;

with 4-chloro-2-(isoxazol-5-yl)-5,6-dimethylthieno[2,3-d]
pyrimidine, 2-(isoxazol-5-yl)-4-(3,4-dichlorobenzylamino)-5,6-dimethylthieno[2,3-d]pyrimidine;

with 4-chloro-2-(isoxazol-5-yl)-6-trifluoromethylthieno[2,3-d]pyrimidine, 2-(isoxazol-5-yl)-4-(3,4-dichlorobenzylamino)-6-trifluoromethylthieno[2,3-d]pyrimidine;

with 4-chloro-2-(pyrazin-2-yl)-6-methylthieno[2,3-d]
pyrimidine, 2-(pyrazin-2-yl)-4-(3,4-dichlorobenzylamino)-6-methylthieno[2,3-d]pyrimidine;

with 4-chloro-2-(pyrazin-2-yl)-5-methylthieno[2,3-d]
pyrimidine, 2-(pyrazin-2-yl)-4-(3,4-dichlorobenzylamino)-5-methylthieno[2,3-d]pyrimidine;

with 4-chloro-2-(pyrazin-2-yl)-5,6,7,8-tetrahydro[1]
benzothieno[2,3-d]pyrimidine, 2-(pyrazin-2-yl)-4-(3,4-dichlorobenzylamino)-5,6,7,8-tetrahydro[1]benzothieno[2,3-d]pyrimidine;

with 4-chloro-2-(pyrazin-2-yl)-5,6-cyclopentenothieno[2,3-d]pyrimidine, 2-(pyrazin-2-yl)-4-(3,4-dichlorobenzylamino)-5,6-cyclopentenothieno[2,3-d]pyrimidine;

with 4-chloro-2-(pyrazin-2-yl)-5,6-cycloheptenothieno[2,3-d]pyrimidine, 2-(pyrazin-2-yl)-4-(3,4-dichlorobenzylamino)-5,6-cycloheptenothieno[2,3-d]pyrimidine;

with 4-chloro-2-(pyrazin-2-yl)-6-ethylthieno[2,3-d]
pyrimidine, 2-(pyrazin-2-yl)-4-(3,4-dichlorobenzylamino)-6-ethylthieno[2,3-d]pyrimidine;

with 4-chloro-2-(pyrazin-2-yl)-6-chlorothieno[2,3-d]
pyrimidine, 2-(pyrazin-2-yl)-4-(3,4-dichlorobenzylamino)-6-chlorothieno[2,3-d]pyrimidine;

with 4-chloro-2-(pyrazin-2-yl)-5-chloro-6-methylthieno[2,3-d]pyrimidine, 2-(pyrazin-2-yl)-4-(3,4-dichlorobenzylamino)-5-chloro-6-methylthieno[2,3-d]pyrimidine;

with 4-chloro-2-(pyrazin-2-yl)-6-nitrothieno[2,3-d]
pyrimidine, 2-(pyrazin-2-yl)-4-(3,4-dichlorobenzylamino)-6-nitrothieno[2,3-d]pyrimidine;

with 4-chloro-2-(pyrazin-2-yl)-5,6-dimethylthieno[2,3-d]
pyrimidine, 2-(pyrazin-2-yl)-4-(3,4-dichlorobenzylamino)-5,6-dimethylthieno[2,3-d]pyrimidine;

with 4-chloro-2-(pyrazin-2-yl)-6-trifluoromethylthieno[2,3-d]pyrimidine, 2-(pyrazin-2-yl)-4-(3,4-dichlorobenzylamino)-6-trifluoromethylthieno[2,3-d]pyrimidine;

with 4-chloro-2-(pyridin-2-yl)-6-methylthieno[2,3-d]
pyrimidine, 2-(pyridin-2-yl)-4-(3,4-dichlorobenzylamino)-6-methylthieno[2,3-d]pyrimidine;

with 4-chloro-2-(pyridin-2-yl)-5-methylthieno[2,3-d]
pyrimidine, 2-(pyridin-2-yl)-4-(3,4-dichlorobenzylamino)-5-methylthieno[2,3-d]pyrimidine;

with 4-chloro-2-(pyridin-2-yl)-5,6,7,8-tetrahydro[1]
benzothieno[2,3-d]pyrimidine, 2-(pyridin-2-yl)-4-(3,4-dichlorobenzylamino)-5,6,7,8-tetrahydro[1]benzothieno[2,3-d]pyrimidine;

with 4-chloro-2-(pyridin-2-yl)-5,6-cyclopentenothieno[2,3-d]pyrimidine, 2-(pyridin-2-yl)-4-(3,4-dichlorobenzylamino)-5,6-cyclopentenothieno[2,3-d]pyrimidine;

with 4-chloro-2-(pyridin-2-yl)-5,6-cycloheptenothieno[2,3-d]pyrimidine, 2-(pyridin-2-yl)-4-(3,4-dichlorobenzylamino)-5,6-cycloheptenothieno[2,3-d]pyrimidine;

with 4-chloro-2-(pyridin-2-yl)-6-ethylthieno[2,3-d]
pyrimidine, 2-(pyridin-2-yl)-4-(3,4-dichlorobenzylamino)-6-ethylthieno[2,3-d]pyrimidine;

with 4-chloro-2-(pyridin-2-yl)-6-chlorothieno[2,3-d]
pyrimidine, 2-(pyridin-2-yl)-4-(3,4-dichlorobenzylamino)-6-chlorothieno[2,3-d]pyrimidine;

with 4-chloro-2-(pyridin-2-yl)-5-chloro-6-methylthieno[2,3-d]pyrimidine, 2-(pyridin-2-yl)-4-(3,4-dichlorobenzylamino)-5-chloro-6-methylthieno[2,3-d]pyrimidine;

with 4-chloro-2-(pyridin-2-yl)-6-nitrothieno[2,3-d]
pyrimidine, 2-(pyridin-2-yl)-4-(3,4-dichlorobenzylamino)-6-nitrothieno[2,3-d]pyrimidine;

with 4-chloro-2-(pyridin-2-yl)-5,6-dimethylthieno[2,3-d]
pyrimidine, 2-(pyridin-2-yl)-4-(3,4-dichlorobenzylamino)-5,6-dimethylthieno[2,3-d]pyrimidine;

with 4-chloro-2-(pyridin-2-yl)-6-trifluoromethylthieno[2,3-d]pyrimidine, 2-(pyridin-2-yl)-4-(3,4-dichlorobenzylamino)-6-trifluoromethylthieno[2,3-d]pyrimidine;

with 4-chloro-2-(pyridin-4-yl)-6-methylthieno[2,3-d]
pyrimidine, 2-(pyridin-4-yl)-4-(3,4-dichlorobenzylamino)-6-methylthieno[2,3-d]pyrimidine;

with 4-chloro-2-(pyridin-4-yl)-5-methylthieno[2,3-d]
pyrimidine, 2-(pyridin-4-yl)-4-(3,4-dichlorobenzylamino)-5-methylthieno[2,3-d]pyrimidine;

with 4-chloro-2-(pyridin-4-yl)-5,6,7,8-tetrahydro[1]
benzothieno[2,3-d]pyrimidine, 2-(pyridin-4-yl)-4-(3,4-dichlorobenzylamino)-5,6,7,8-tetrahydro[1]benzothieno[2,3-d]pyrimidine;

with 4-chloro-2-(pyridin-4-yl)-5,6-cyclopentenothieno[2,3-d]pyrimidine, 2-(pyridin-4-yl)-4-(3,4-dichlorobenzylamino)-5,6-cyclopentenothieno[2,3-d]pyrimidine;

with 4-chloro-2-(pyridin-4-yl)-5,6-cycloheptenothieno[2,3-d]pyrimidine, 2-(pyridin-4-yl)-4-(3,4-dichlorobenzylamino)-5,6-cycloheptenothieno[2,3-d]pyrimidine;

with 4-chloro-2-(pyridin-4-yl)-6-ethylthieno[2,3-d]pyrimidine, 2-(pyridin-4-yl)-4-(3,4-dichlorobenzylamino)-6-ethylthieno[2,3-d]pyrimidine;

with 4-chloro-2-(pyridin-4-yl)-6-chlorothieno[2,3-d]pyrimidine, 2-(pyridin-4-yl)-4-(3,4-dichlorobenzylamino)-6-chlorothieno[2,3-d]pyrimidine;

with 4-chloro-2-(pyridin-4-yl)-5-chloro-6-methylthieno[2,3-d]pyrimidine, 2-(pyridin-4-yl)-4-(3,4-dichlorobenzylamino)-5-chloro-6-methylthieno[2,3-d]pyrimidine;

with 4-chloro-2-(pyridin-4-yl)-6-nitrothieno[2,3-d]pyrimidine, 2-(pyridin-4-yl)-4-(3,4-dichlorobenzylamino)-6-nitrothieno[2,3-d]pyrimidine;

with 4-chloro-2-(pyridin-4-yl)-5,6-dimethylthieno[2,3-d]pyrimidine, 2-(pyridin-4-yl)-4-(3,4-dichlorobenzylamino)-5,6-dimethylthieno[2,3-d]pyrimidine;

with 4-chloro-2-(pyridin-4-yl)-6-trifluoromethylthieno[2,3-d]pyrimidine, 2-(pyridin-4-yl)-4-(3,4-dichlorobenzylamino)-6-trifluoromethylthieno[2,3-d]pyrimidine;

The following are obtained analogously by reaction of 3-nitrobenzylamine:

with 4-chloro-2-(pyridin-3-yl)-6-methylthieno[2,3-d]pyrimidine, 2-(pyridin-3-yl)-4-(3-nitrobenzylamino)-6-methylthieno[2,3-d]pyrimidine;

with 4-chloro-2-(pyridin-3-yl)-5-methylthieno[2,3-d]pyrimidine, 2-(pyridin-3-yl)-4-(3-nitrobenzylamino)-5-methylthieno[2,3-d]pyrimidine;

with 4-chloro-2-(pyridin-3-yl)-5,6,7,8-tetrahydro[1]benzothieno[2,3-d]pyrimidine, 2-(pyridin-3-yl)-4-(3-nitrobenzylamino)-5,6,7,8-tetrahydro[1]benzothieno[2,3-d]pyrimidine;

with 4-chloro-2-(pyridin-3-yl)-5,6-cyclopentenothieno[2,3-d]pyrimidine, 2-(pyridin-3-yl)-4-(3-nitrobenzylamino)-5,6-cyclopentenothieno[2,3-d]pyrimidine;

with 4-chloro-2-(pyridin-3-yl)-5,6-cycloheptenothieno[2,3-d]pyrimidine, 2-(pyridin-3-yl)-4-(3-nitrobenzylamino)-5,6-cycloheptenothieno[2,3-d]pyrimidine;

with 4-chloro-2-(pyridin-3-yl)-6-ethylthieno[2,3-d]pyrimidine, 2-(pyridin-3-yl)-4-(3-nitrobenzylamino)-6-ethylthieno[2,3-d]pyrimidine;

with 4-chloro-2-(pyridin-3-yl)-6-chlorothieno[2,3-d]pyrimidine, 2-(pyridin-3-yl)-4-(3-nitrobenzylamino)-6-chlorothieno[2,3-d]pyrimidine;

with 4-chloro-2-(pyridin-3-yl)-5-chloro-6-methylthieno[2,3-d]pyrimidine, 2-(pyridin-3-yl)-4-(3-nitrobenzylamino)-5-chloro-6-methylthieno[2,3-d]pyrimidine;

with 4-chloro-2-(pyridin-3-yl)-6-nitrothieno[2,3-d]pyrimidine, 2-(pyridin-3-yl)-4-(3-nitrobenzylamino)-6-nitrothieno[2,3-d]pyrimidine;

with 4-chloro-2-(pyridin-3-yl)-5,6-dimethylthieno[2,3-d]pyrimidine, 2-(pyridin-3-yl)-4-(3-nitrobenzylamino)-5,6-dimethylthieno[2,3-d]pyrimidine;

with 4-chloro-2-(pyridin-3-yl)-6-trifluoromethylthieno[2,3-d]pyrimidine, 2-(pyridin-3-yl)-4-(3-nitrobenzylamino)-6-trifluoromethylthieno[2,3-d]pyrimidine;

with 4-chloro-2-(isoxazol-5-yl)-6-methylthieno[2,3-d]pyrimidine, 2-(isoxazol-5-yl)-4-(3-nitrobenzylamino)-6-methylthieno[2,3-d]pyrimidine;

with 4-chloro-2-(isoxazol-5-yl)-5-methylthieno[2,3-d]pyrimidine, 2-(isoxazol-5-yl)-4-(3-nitrobenzylamino)-5-methylthieno[2,3-d]pyrimidine;

with 4-chloro-2-(isoxazol-5-yl)-5,6,7,8-tetrahydro[1]benzothieno[2,3-d]pyrimidine, 2-(isoxazol-5-yl)-4-(3-nitrobenzylamino)-5,6,7,8-tetrahydro[1]benzothieno[2,3-d]pyrimidine;

with 4-chloro-2-(isoxazol-5-yl)-5,6-cyclopentenothieno[2,3-d]pyrimidine, 2-(isoxazol-5-yl)-4-(3-nitrobenzylamino)-5,6-cyclopentenothieno[2,3-d]pyrimidine;

with 4-chloro-2-(isoxazol-5-yl)-5,6-cycloheptenothieno[2,3-d]pyrimidine, 2-(isoxazol-5-yl)-4-(3-nitrobenzylamino)-5,6-cycloheptenothieno[2,3-d]pyrimidine;

with 4-chloro-2-(isoxazol-5-yl)-6-ethylthieno[2,3-d]pyrimidine, 2-(isoxazol-5-yl)-4-(3-nitrobenzylamino)-6-ethylthieno[2,3-d]pyrimidine;

with 4-chloro-2-(isoxazol-5-yl)-6-chlorothieno[2,3-d]pyrimidine, 2-(isoxazol-5-yl)-4-(3-nitrobenzylamino)-6-chlorothieno[2,3-d]pyrimidine;

with 4-chloro-2-(isoxazol-5-yl)-5-chloro-6-methylthieno[2,3-d]pyrimidine, 2-(isoxazol-5-yl)-4-(3-nitrobenzylamino)-5-chloro-6-methylthieno[2,3-d]pyrimidine;

with 4-chloro-2-(isoxazol-5-yl)-6-nitrothieno[2,3-d]pyrimidine, 2-(isoxazol-5-yl)-4-(3-nitrobenzylamino)-6-nitrothieno[2,3-d]pyrimidine;

with 4-chloro-2-(isoxazol-5-yl)-5,6-dimethylthieno[2,3-d]pyrimidine, 2-(isoxazol-5-yl)-4-(3-nitrobenzylamino)-5,6-dimethylthieno[2,3-d]pyrimidine;

with 4-chloro-2-(isoxazol-5-yl)-6-trifluoromethylthieno[2,3-d]pyrimidine, 2-(isoxazol-5-yl)-4-(3-nitrobenzylamino)-6-trifluoromethylthieno[2,3-d]pyrimidine;

with 4-chloro-2-(pyrazin-2-yl)-6-methylthieno[2,3-d]pyrimidine, 2-(pyrazin-2-yl)-4-(3-nitrobenzylamino)-6-methylthieno[2,3-d]pyrimidine;

with 4-chloro-2-(pyrazin-2-yl)-5-methylthieno[2,3-d]pyrimidine, 2-(pyrazin-2-yl)-4-(3-nitrobenzylamino)-5-methylthieno[2,3-d]pyrimidine;

with 4-chloro-2-(pyrazin-2-yl)-5,6,7,8-tetrahydro[1]benzothieno[2,3-d]pyrimidine, 2-(pyrazin-2-yl)-4-(3-nitrobenzylamino)-5,6,7,8-tetrahydro[1]benzothieno[2,3-d]pyrimidine;

with 4-chloro-2-(pyrazin-2-yl)-5,6-cyclopentenothieno[2,3-d]pyrimidine, 2-(pyrazin-2-yl)-4-(3-nitrobenzylamino)-5,6-cyclopentenothieno[2,3-d]pyrimidine;

with 4-chloro-2-(pyrazin-2-yl)-5,6-cycloheptenothieno[2,3-d]pyrimidine, 2-(pyrazin-2-yl)-4-(3-nitrobenzylamino)-5,6-cycloheptenothieno[2,3-d]pyrimidine;

with 4-chloro-2-(pyrazin-2-yl)-6-ethylthieno[2,3-d]pyrimidine, 2-(pyrazin-2-yl)-4-(3-nitrobenzylamino)-6-ethylthieno[2,3-d]pyrimidine;

with 4-chloro-2-(pyrazin-2-yl)-6-chlorothieno[2,3-d]pyrimidine, 2-(pyrazin-2-yl)-4-(3-nitrobenzylamino)-6-chlorothieno[2,3-d]pyrimidine;

with 4-chloro-2-(pyrazin-2-yl)-5-chloro-6-methylthieno[2,3-d]pyrimidine, 2-(pyrazin-2-yl)-4-(3-nitrobenzylamino)-5-chloro-6-methylthieno[2,3-d]pyrimidine;

with 4-chloro-2-(pyrazin-2-yl)-6-nitrothieno[2,3-d]pyrimidine, 2-(pyrazin-2-yl)-4-(3-nitrobenzylamino)-6-nitrothieno[2,3-d]pyrimidine;

with 4-chloro-2-(pyrazin-2-yl)-5,6-dimethylthieno[2,3-d]pyrimidine, 2-(pyrazin-2-yl)-4-(3-nitrobenzylamino)-5,6-dimethylthieno[2,3-d]pyrimidine;

with 4-chloro-2-(pyrazin-2-yl)-6-trifluoromethylthieno[2,3-d]pyrimidine, 2-(pyrazin-2-yl)-4-(3-nitrobenzylamino)-6-trifluoromethylthieno[2,3-d]pyrimidine;

with 4-chloro-2-(pyridin-2-yl)-6-methylthieno[2,3-d]pyrimidine, 2-(pyridin-2-yl)-4-(3-nitrobenzylamino)-6-methylthieno[2,3-d]pyrimidine;

with 4-chloro-2-(pyridin-2-yl)-5-methylthieno[2,3-d]pyrimidine, 2-(pyridin-2-yl)-4-(3-nitrobenzylamino)-5-methylthieno[2,3-d]pyrimidine;

with 4-chloro-2-(pyridin-2-yl)-5,6,7,8-tetrahydro[1]benzothieno[2,3-d]pyrimidine, 2-(pyridin-2-yl)-4-(3-nitrobenzylamino)-5,6,7,8-tetrahydro[1]benzothieno[2,3-d]pyrimidine;

with 4-chloro-2-(pyridin-2-yl)-5,6-cyclopentenothieno[2,3-d]pyrimidine, 2-(pyridin-2-yl)-4-(3-nitrobenzylamino)-5,6-cyclopentenothieno[2,3-d]pyrimidine;

with 4-chloro-2-(pyridin-2-yl)-5,6-cycloheptenothieno[2,3-d]pyrimidine, 2-(pyridin-2-yl)-4-(3-nitrobenzylamino)-5,6-cycloheptenothieno[2,3-d]pyrimidine;

with 4-chloro-2-(pyridin-2-yl)-6-ethylthieno[2,3-d]pyrimidine, 2-(pyridin-2-yl)-4-(3-nitrobenzylamino)-6-ethylthieno[2,3-d]pyrimidine;

with 4-chloro-2-(pyridin-2-yl)-6-chlorothieno[2,3-d]pyrimidine, 2-(pyridin-2-yl)-4-(3-nitrobenzylamino)-6-chlorothieno[2,3-d]pyrimidine;

with 4-chloro-2-(pyridin-2-yl)-5-chloro-6-methylthieno[2,3-d]pyrimidine, 2-(pyridin-2-yl)-4-(3-nitrobenzylamino)-5-chloro-6-methylthieno[2,3-d]pyrimidine;

with 4-chloro-2-(pyridin-2-yl)-6-nitrothieno[2,3-d]pyrimidine, 2-(pyridin-2-yl)-4-(3-nitrobenzylamino)-6-nitrothieno[2,3-d]pyrimidine;

with 4-chloro-2-(pyridin-2-yl)-5,6-dimethylthieno[2,3-d]pyrimidine, 2-(pyridin-2-yl)-4-(3-nitrobenzylamino)-5,6-dimethylthieno[2,3-d]pyrimidine;

with 4-chloro-2-(pyridin-2-yl)-6-trifluoromethylthieno[2,3-d]pyrimidine, 2-(pyridin-2-yl)-4-(3-nitrobenzylamino)-6-trifluoromethylthieno[2,3-d]pyrimidine;

with 4-chloro-2-(pyridin-4-yl)-6-methylthieno[2,3-d]pyrimidine, 2-(pyridin-4-yl)-4-(3-nitrobenzylamino)-6-methylthieno[2,3-d]pyrimidine;

with 4-chloro-2-(pyridin-4-yl)-5-methylthieno[2,3-d]pyrimidine, 2-(pyridin-4-yl)-4-(3-nitrobenzylamino)-5-methylthieno[2,3-d]pyrimidine;

with 4-chloro-2-(pyridin-4-yl)-5,6,7,8-tetrahydro[1]benzothieno[2,3-d]pyrimidine, 2-(pyridin-4-yl)-4-(3-nitrobenzylamino)-5,6,7,8-tetrahydro[1]benzothieno[2,3-d]pyrimidine;

with 4-chloro-2-(pyridin-4-yl)-5,6-cyclopentenothieno[2,3-d]pyrimidine, 2-(pyridin-4-yl)-4-(3-nitrobenzylamino)-5,6-cyclopentenothieno[2,3-d]pyrimidine;

with 4-chloro-2-(pyridin-4-yl)-5,6-cycloheptenothieno[2,3-d]pyrimidine, 2-(pyridin-4-yl)-4-(3-nitrobenzylamino)-5,6-cycloheptenothieno[2,3-d]pyrimidine;

with 4-chloro-2-(pyridin-4-yl)-6-ethylthieno[2,3-d]pyrimidine, 2-(pyridin-4-yl)-4-(3-nitrobenzylamino)-6-ethylthieno[2,3-d]pyrimidine;

with 4-chloro-2-(pyridin-4-yl)-6-chlorothieno[2,3-d]pyrimidine, 2-(pyridin-4-yl)-4-(3-nitrobenzylamino)-6-chlorothieno[2,3-d]pyrimidine;

with 4-chloro-2-(pyridin-4-yl)-5-chloro-6-methylthieno[2,3-d]pyrimidine, 2-(pyridin-4-yl)-4-(3-nitrobenzylamino)-5-chloro-6-methylthieno[2,3-d]pyrimidine;

with 4-chloro-2-(pyridin-4-yl)-6-nitrothieno[2,3-d]pyrimidine, 2-(pyridin-4-yl)-4-(3-nitrobenzylamino)-6-nitrothieno[2,3-d]pyrimidine;

with 4-chloro-2-(pyridin-4-yl)-5,6-dimethylthieno[2,3-d]pyrimidine, 2-(pyridin-4-yl)-4-(3-nitrobenzylamino)-5,6-dimethylthieno[2,3-d]pyrimidine;

with 4-chloro-2-(pyridin-4-yl)-6-trifluoromethylthieno[2,3-d]pyrimidine, 2-(pyridin-4-yl)-4-(3-nitrobenzylamino)-6-trifluoromethylthieno[2,3-d]pyrimidine;

The following are obtained analogously by reaction of 3,4-methylenedioxyphenethylamine:

with 4-chloro-2-(pyridin-3-yl)-6-methylthieno[2,3-d]pyrimidine, 2-(pyridin-3-yl)-4-(3,4-methylenedioxyphenethylamino)-6-methylthieno[2,3-d]pyrimidine;

with 4-chloro-2-(pyridin-3-yl)-5-methylthieno[2,3-d]pyrimidine, 2-(pyridin-3-yl)-4-(3,4-methylenedioxyphenethylamino)-5-methylthieno[2,3-d]pyrimidine;

with 4-chloro-2-(pyridin-3-yl)-5,6,7,8-tetrahydro[1]benzothieno[2,3-d]pyrimidine, 2-(pyridin-3-yl)-4-(3,4-methylenedioxyphenethylamino)-5,6,7,8-tetrahydro[1]benzothieno[2,3-d]pyrimidine;

with 4-chloro-2-(pyridin-3-yl)-5,6-cyclopentenothieno[2,3-d]pyrimidine, 2-(pyridin-3-yl)-4-(3,4-methylenedioxyphenethylamino)-5,6-cyclopentenothieno[2,3-d]pyrimidine;

with 4-chloro-2-(pyridin-3-yl)-5,6-cycloheptenothieno[2,3-d]pyrimidine, 2-(pyridin-3-yl)-4-(3,4-methylenedioxyphenethylamino)-6-ethylthieno[2,3-d]pyrimidine;

with 4-chloro-2-(pyridin-3-yl)-6-chlorothieno[2,3-d]pyrimidine, 2-(pyridin-3-yl)-4-(3,4-methylenedioxyphenethylamino)-6-chlorothieno[2,3-d]pyrimidine;

with 4-chloro-2-(pyridin-3-yl)-5-chloro-6-methylthieno[2,3-d]pyrimidine, 2-(pyridin-3-yl)-4-(3,4-methylenedioxyphenethylamino)-5-chloro-6-methylthieno[2,3-d]pyrimidine;

with 4-chloro-2-(pyridin-3-yl)-6-nitrothieno[2,3-d]pyrimidine, 2-(pyridin-3-yl)-4-(3,4-methylenedioxyphenethylamino)-6-nitrothieno[2,3-d]pyrimidine;

with 4-chloro-2-(pyridin-3-yl)-5,6-dimethylthieno[2,3-d]pyrimidine, 2-(pyridin-3-yl)-4-(3,4-methylenedioxyphenethylamino)-5,6-dimethylthieno[2,3-d]pyrimidine;

with 4-chloro-2-(pyridin-3-yl)-6-trifluoromethylthieno[2,3-d]pyrimidine, 2-(pyridin-3-yl)-4-(3,4-methylenedioxyphenethylamino)-6-trifluoromethylthieno[2,3-d]pyrimidine;

with 4-chloro-2-(isoxazol-5-yl)-6-methylthieno[2,3-d]pyrimidine, 2-(isoxazol-5-yl)-4-(3,4-methylenedioxyphenethylamino)-6-methylthieno[2,3-d]pyrimidine;

with 4-chloro-2-(isoxazol-5-yl)-5-methylthieno[2,3-d]pyrimidine, 2-(isoxazol-5-yl)-4-(3,4-methylenedioxyphenethylamino)-5-methylthieno[2,3-d]pyrimidine;

with 4-chloro-2-(isoxazol-5-yl)-5,6,7,8-tetrahydro[1]benzothieno[2,3-d]-pyrimidine, 2-(isoxazol-5-yl)-4-(3,4-methylenedioxyphenethylamino)-5,6,7,8-tetrahydro[1]benzothieno[2,3-d]pyrimidine;

with 4-chloro-2-(isoxazol-5-yl)-5,6-cyclopentenothieno[2,3-d]pyrimidine, 2-(isoxazol-5-yl)-4-(3,4-methylenedioxyphenethylamino)-5,6-cyclopentenothieno[2,3-d]pyrimidine;

with 4-chloro-2-(isoxazol-5-yl)-5,6-cycloheptenothieno[2,3-d]pyrimidine, 2-(isoxazol-5-yl)-4-(3,4-methylenedioxyphenethylamino)-5,6-cycloheptenothieno[2,3-d]pyrimidine;

with 4-chloro-2-(isoxazol-5-yl)-6-ethylthieno[2,3-d]pyrimidine, 2-(isoxazol-5-yl)-4-(3,4-methylenedioxyphenethylamino)-6-ethylthieno[2,3-d]pyrimidine;

with 4-chloro-2-(isoxazol-5-yl)-6-chlorothieno[2,3-d]pyrimidine, 2-(isoxazol-5-yl)-4-(3,4-methylenedioxyphenethylamino)-6-chlorothieno[2,3-d]pyrimidine;

with 4-chloro-2-(isoxazol-5-yl)-5-chloro-6-methylthieno[2,3-d]pyrimidine, 2-(isoxazol-5-yl)-4-(3,4-methylenedioxyphenethylamino)-5-chloro-6-methylthieno[2,3-d]pyrimidine;

with 4-chloro-2-(isoxazol-5-yl)-6-nitrothieno[2,3-d] pyrimidine, 2-(isoxazol-5-yl)-4-(3,4-methylenedioxyphenethylamino)-6-nitrothieno[2,3-d]pyrimidine;

with 4-chloro-2-(isoxazol-5-yl)-5,6-dimethylthieno[2,3-d] pyrimidine, 2-(isoxazol-5-yl)-4-(3,4-methylenedioxyphenethylamino)-5,6-dimethylthieno[2,3-d]pyrimidine;

with 4-chloro-2-(isoxazol-5-yl)-6-trifluoromethylthieno[2,3-d]pyrimidine, 2-(isoxazol-5-yl)-4-(3,4-methylenedioxyphenethylamino)-6-trifluoromethylthieno[2,3-d]pyrimidine;

with 4-chloro-2-(pyrazin-2-yl)-6-methylthieno[2,3-d] pyrimidine, 2-(pyrazin-2-yl)-4-(3,4-methylenedioxyphenethylamino)-6-methylthieno[2,3-d] pyrimidine;

with 4-chloro-2-(pyrazin-2-yl)-5-methylthieno[2,3-d] pyrimidine, 2-(pyrazin-2-yl)-4-(3,4-methylenedioxyphenethylamino)-5-methylthieno[2,3-d] pyrimidine;

with 4-chloro-2-(pyrazin-2-yl)-5,6,7,8-tetrahydro[1] benzothieno[2,3-d]pyrimidine, 2-(pyrazin-2-yl)-4-(3,4-methylenedioxyphenethylamino)-5,6,7,8-tetrahydro[1] benzothieno[2,3-d]pyrimidine;

with 4-chloro-2-(pyrazin-2-yl)-5,6-cyclopentenothieno[2,3-d]pyrimidine, 2-(pyrazin-2-yl)-4-(3,4-methylenedioxyphenethylamino)-5,6-cyclopentenothieno [2,3-d]pyrimidine;

with 4-chloro-2-(pyrazin-2-yl)-5,6-cycloheptenothieno[2,3-d]pyrimidine, 2-(pyrazin-2-yl)-4-(3,4-methylenedioxyphenethylamino)-5,6-cycloheptenothieno [2,3-d]pyrimidine;

with 4-chloro-2-(pyrazin-2-yl)-6-ethylthieno[2,3-d] pyrimidine, 2-(pyrazin-2-yl)-4-(3,4-methylenedioxyphenethylamino)-6-ethylthieno[2,3-d] pyrimidine;

with 4-chloro-2-(pyrazin-2-yl)-6-chlorothieno[2,3-d] pyrimidine, 2-(pyrazin-2-yl)-4-(3,4-methylenedioxyphenethylamino)-6-chlorothieno[2,3-d] pyrimidine;

with 4-chloro-2-(pyrazin-2-yl)-5-chloro-6-methylthieno[2,3-d]pyrimidine, 2-(pyrazin-2-yl)-4-(3,4-methylenedioxyphenethylamino)-5-chloro-6-methylthieno[2,3-d]pyrimidine;

with 4-chloro-2-(pyrazin-2-yl)-6-nitrothieno[2,3-d] pyrimidine, 2-(pyrazin-2-yl)-4-(3,4-methylenedioxyphenethylamino)-6-nitrothieno[2,3-d] pyrimidine;

with 4-chloro-2-(pyrazin-2-yl)-5,6-dimethylthieno[2,3-d] pyrimidine, 2-(pyrazin-2-yl)-4-(3,4-methylenedioxyphenethylamino)-5,6-dimethylthieno[2,3-d]pyrimidine;

with 4-chloro-2-(pyrazin-2-yl)-6-trifluoromethylthieno[2,3-d]pyrimidine, 2-(pyrazin-2-yl)-4-(3,4-methylenedioxyphenethylamino)-6-trifluoromethylthieno [2,3-d]pyrimidine;

with 4-chloro-2-(pyridin-2-yl)-6-methylthieno[2,3-d] pyrimidine, 2-(pyridin-2-yl)-4-(3,4-methylenedioxyphenethylamino)-6-methylthieno[2,3-d] pyrimidine;

with 4-chloro-2-(pyridin-2-yl)-5-methylthieno[2,3-d] pyrimidine, 2-(pyridin-2-yl)-4-(3,4-methylenedioxyphenethylamino)-5-methylthieno[2,3-d] pyrimidine;

with 4-chloro-2-(pyridin-2-yl)-5,6,7,8-tetrahydro[1] benzothieno[2,3-d]-pyrimidine, 2-(pyridin-2-yl)-4-(3,4-methylenedioxyphenethylamino)-5,6,7,8-tetrahydro[1] benzothieno[2,3-d]pyrimidine;

with 4-chloro-2-(pyridin-2-yl)-5,6-cyclopentenothieno[2,3-d]pyrimidine, 2-(pyridin-2-yl)-4-(3,4-methylenedioxyphenethylamino)-5,6-cyclopentenothieno [2,3-d]pyrimidine;

with 4-chloro-2-(pyridin-2-yl)-5,6-cycloheptenothieno[2,3-d]pyrimidine, 2-(pyridin-2-yl)-4-(3,4-methylenedioxyphenethylamino)-5,6-cycloheptenothieno [2,3-d]pyrimidine;

with 4-chloro-2-(pyridin-2-yl)-6-ethylthieno[2,3-d] pyrimidine, 2-(pyridin-2-yl)-4-(3,4-methylenedioxyphenethylamino)-6-ethylthieno[2,3-d] pyrimidine;

with 4-chloro-2-(pyridin-2-yl)-6-chlorothieno[2,3-d] pyrimidine, 2-(pyridin-2-yl)-4-(3,4-methylenedioxyphenethylamino)-6-chlorothieno[2,3-d] pyrimidine;

with 4-chloro-2-(pyridin-2-yl)-5-chloro-6-methylthieno[2,3-d]pyrimidine, 2-(pyridin-2-yl)-4-(3,4-methylenedioxyphenethylamino)-5-chloro-6-methylthieno[2,3-d]pyrimidine;

with 4-chloro-2-(pyridin-2-yl)-6-nitrothieno[2,3-d] pyrimidine, 2-(pyridin-2-yl)-4-(3,4-methylenedioxyphenethylamino)-6-nitrothieno[2,3-d] pyrimidine;

with 4-chloro-2-(pyridin-2-yl)-5,6-dimethylthieno[2,3-d] pyrimidine, 2-(pyridin-2-yl)-4-(3,4-methylenedioxyphenethylamino)-5,6-dimethylthieno[2,3-d]pyrimidine;

with 4-chloro-2-(pyridin-2-yl)-6-trifluoromethylthieno[2,3-d]pyrimidine, 2-(pyridin-2-yl)-4-(3,4-methylenedioxyphenethylamino)-6-trifluoromethylthieno [2,3-d]pyrimidine;

with 4-chloro-2-(pyridin-4-yl)-6-methylthieno[2,3-d] pyrimidine, 2-(pyridin-4-yl)-4-(3,4-methylenedioxyphenethylamino)-6-methylthieno[2,3-d] pyrimidine;

with 4-chloro-2-(pyridin-4-yl)-5-methylthieno[2,3-d] pyrimidine, 2-(pyridin-4-yl)-4-(3,4-methylenedioxyphenethylamino)-5-methylthieno[2,3-d] pyrimidine;

with 4-chloro-2-(pyridin-4-yl)-5,6,7,8-tetrahydro[1] benzothieno[2,3-d]-pyrimidine, 2-(pyridin-4-yl)-4-(3,4-methylenedioxyphenethylamino)-5,6,7,8-tetrahydro[1] benzothieno[2,3-d]pyrimidine;

with 4-chloro-2-(pyridin-4-yl)-5,6-cyclopentenothieno[2,3-d]pyrimidine, 2-(pyridin-4-yl)-4-(3,4-methylenedioxyphenethylamino)-5,6-cyclopentenothieno [2,3-d]pyrimidine;

with 4-chloro-2-(pyridin-4-yl)-5,6-cycloheptenothieno[2,3-d]pyrimidine, 2-(pyridin-4-yl)-4-(3,4-methylenedioxyphenethylamino)-5,6-cycloheptenothieno [2,3-d]pyrimidine;

with 4-chloro-2-(pyridin-4-yl)-6-ethylthieno[2,3-d] pyrimidine, 2-(pyridin-4-yl)-4-(3,4-methylenedioxyphenethylamino)-6-ethylthieno[2,3-d] pyrimidine;

with 4-chloro-2-(pyridin-4-yl)-6-chlorothieno[2,3-d] pyrimidine, 2-(pyridin-4-yl)-4-(3,4-methylenedioxyphenethylamino)-6-chlorothieno[2,3-d] pyrimidine;

with 4-chloro-2-(pyridin-4-yl)-5-chloro-6-methylthieno[2,3-d]pyrimidine, 2-(pyridin-4-yl)-4-(3,4-methylenedioxyphenethylamino)-5-chloro-6-methylthieno[2,3-d]pyrimidine;

with 4-chloro-2-(pyridin-4-yl)-6-nitrothieno[2,3-d] pyrimidine, 2-(pyridin-4-yl)-4-(3,4-methylenedioxyphenethylamino)-6-nitrothieno[2,3-d] pyrimidine;

with 4-chloro-2-(pyridin-4-yl)-5,6-dimethylthieno[2,3-d]pyrimidine, 2-(pyridin-4-yl)-4-(3,4-methylenedioxyphenethylamino)-5,6-dimethylthieno[2,3-d]pyrimidine;
with 4-chloro-2-(pyridin-4-yl)-6-trifluoromethylthieno[2,3-d]pyrimidine, 2-(pyridin-4-yl)-4-(3,4-methylenedioxyphenethylamino)-6-trifluoromethylthieno[2,3-d]pyrimidine;

The following are obtained analogously by reaction of 3,4-ethylenedioxybenzylamine:

with 4-chloro-2-(pyridin-3-yl)-6-methylthieno[2,3-d]pyrimidine, 2-(pyridin-3-yl)-4-(3,4-ethylenedioxybenzylamino)-6-methylthieno[2,3-d]pyrimidine;
with 4-chloro-2-(pyridin-3-yl)-5-methylthieno[2,3-d]pyrimidine, 2-(pyridin-3-yl)-4-(3,4-ethylenedioxybenzylamino)-5-methylthieno[2,3-d]pyrimidine;
with 4-chloro-2-(pyridin-3-yl)-5,6,7,8-tetrahydro[1]benzothieno[2,3-d]pyrimidine, 2-(pyridin-3-yl)-4-(3,4-ethylenedioxybenzylamino)-5,6,7,8-tetrahydro[1]benzothieno[2,3-d]pyrimidine;
with 4-chloro-2-(pyridin-3-yl)-5,6-cyclopentenothieno[2,3-d]pyrimidine, 2-(pyridin-3-yl)-4-(3,4-ethylenedioxybenzylamino)-5,6-cyclopentenothieno[2,3-d]pyrimidine;
with 4-chloro-2-(pyridin-3-yl)-5,6-cycloheptenothieno[2,3-d]pyrimidine, 2-(pyridin-3-yl)-4-(3,4-ethylenedioxybenzylamino)-5,6-cycloheptenothieno[2,3-d]pyrimidine;
with 4-chloro-2-(pyridin-3-yl)-6-ethylthieno[2,3-d]pyrimidine, 2-(pyridin-3-yl)-4-(3,4-ethylenedioxybenzylamino)-6-ethylthieno[2,3-d]pyrimidine;
with 4-chloro-2-(pyridin-3-yl)-6-chlorothieno[2,3-d]pyrimidine, 2-(pyridin-3-yl)-4-(3,4-ethylenedioxybenzylamino)-6-chlorothieno[2,3-d]pyrimidine;
with 4-chloro-2-(pyridin-3-yl)-5-chloro-6-methylthieno[2,3-d]pyrimidine, 2-(pyridin-3-yl)-4-(3,4-ethylenedioxybenzylamino)-5-chloro-6-methylthieno[2,3-d]pyrimidine;
with 4-chloro-2-(pyridin-3-yl)-6-nitrothieno[2,3-d]pyrimidine, 2-(pyridin-3-yl)-4-(3,4-ethylenedioxybenzylamino)-6-nitrothieno[2,3-d]pyrimidine;
with 4-chloro-2-(pyridin-3-yl)-5,6-dimethylthieno[2,3-d]pyrimidine, 2-(pyridin-3-yl)-4-(3,4-ethylenedioxybenzylamino)-5,6-dimethylthieno[2,3-d]pyrimidine;
with 4-chloro-2-(pyridin-3-yl)-6-trifluoromethylthieno[2,3-d]pyrimidine, 2-(pyridin-3-yl)-4-(3,4-ethylenedioxybenzylamino)-6-trifluoromethylthieno[2,3-d]pyrimidine;
with 4-chloro-2-(isoxazol-5-yl)-6-methylthieno[2,3-d]pyrimidine, 2-(isoxazol-5-yl)-4-(3,4-ethylenedioxybenzylamino)-6-methylthieno[2,3-d]pyrimidine;
with 4-chloro-2-(isoxazol-5-yl)-5-methylthieno[2,3-d]pyrimidine, 2-(isoxazol-5-yl)-4-(3,4-ethylenedioxybenzylamino)-5-methylthieno[2,3-d]pyrimidine;
with 4-chloro-2-(isoxazol-5-yl)-5,6,7,8-tetrahydro[1]benzothieno[2,3-d]pyrimidine, 2-(isoxazol-5-yl)-4-(3,4-ethylenedioxybenzylamino)-5,6,7,8-tetrahydro[1]benzothieno[2,3-d]pyrimidine;
with 4-chloro-2-(isoxazol-5-yl)-5,6-cyclopentenothieno[2,3-d]pyrimidine, 2-(isoxazol-5-yl)-4-(3,4-ethylenedioxybenzylamino)-5,6-cyclopentenothieno[2,3-d]pyrimidine;
with 4-chloro-2-(isoxazol-5-yl)-5,6-cycloheptenothieno[2,3-d]pyrimidine, 2-(isoxazol-5-yl)-4-(3,4-ethylenedioxybenzylamino)-5,6-cycloheptenothieno[2,3-d]pyrimidine;
with 4-chloro-2-(isoxazol-5-yl)-6-ethylthieno[2,3-d]pyrimidine, 2-(isoxazol-5-yl)-4-(3,4-ethylenedioxybenzylamino)-6-ethylthieno[2,3-d]pyrimidine;
with 4-chloro-2-(isoxazol-5-yl)-6-chlorothieno[2,3-d]pyrimidine, 2-(isoxazol-5-yl)-4-(3,4-ethylenedioxybenzylamino)-6-chlorothieno[2,3-d]pyrimidine;
with 4-chloro-2-(isoxazol-5-yl)-5-chloro-6-methylthieno[2,3-d]pyrimidine, 2-(isoxazol-5-yl)-4-(3,4-ethylenedioxybenzylamino)-5-chloro-6-methylthieno[2,3-d]pyrimidine;
with 4-chloro-2-(isoxazol-5-yl)-6-nitrothieno[2,3-d]pyrimidine, 2-(isoxazol-5-yl)-4-(3,4-ethylenedioxybenzylamino)-6-nitrothieno[2,3-d]pyrimidine;
with 4-chloro-2-(isoxazol-5-yl)-5,6-dimethylthieno[2,3-d]pyrimidine, 2-(isoxazol-5-yl)-4-(3,4-ethylenedioxybenzylamino)-5,6-dimethylthieno[2,3-d]pyrimidine;
with 4-chloro-2-(isoxazol-5-yl)-6-trifluoromethylthieno[2,3-d]pyrimidine, 2-(isoxazol-5-yl)-4-(3,4-ethylenedioxybenzylamino)-6-trifluoromethylthieno[2,3-d]pyrimidine;
with 4-chloro-2-(pyrazin-2-yl)-6-methylthieno[2,3-d]pyrimidine, 2-(pyrazin-2-yl)-4-(3,4-ethylenedioxybenzylamino)-6-methylthieno[2,3-d]pyrimidine;
with 4-chloro-2-(pyrazin-2-yl)-5-methylthieno[2,3-d]pyrimidine, 2-(pyrazin-2-yl)-4-(3,4-ethylenedioxybenzylamino)-5-methylthieno[2,3-d]pyrimidine;
with 4-chloro-2-(pyrazin-2-yl)-5,6,7,8-tetrahydro[1]benzothieno[2,3-d]pyrimidine, 2-(pyrazin-2-yl)-4-(3,4-ethylenedioxybenzylamino)-5,6,7,8-tetrahydro[1]benzothieno[2,3-d]pyrimidine;
with 4-chloro-2-(pyrazin-2-yl)-5,6-cyclopentenothieno[2,3-d]pyrimidine, 2-(pyrazin-2-yl)-4-(3,4-ethylenedioxybenzylamino)-5,6-cyclopentenothieno[2,3-d]pyrimidine;
with 4-chloro-2-(pyrazin-2-yl)-5,6-cycloheptenothieno[2,3-d]pyrimidine, 2-(pyrazin-2-yl)-4-(3,4-ethylenedioxybenzylamino)-5,6-cycloheptenothieno[2,3-d]pyrimidine;
with 4-chloro-2-(pyrazin-2-yl)-6-ethylthieno[2,3-d]pyrimidine, 2-(pyrazin-2-yl)-4-(3,4-ethylenedioxybenzylamino)-6-ethylthieno[2,3-d]pyrimidine;
with 4-chloro-2-(pyrazin-2-yl)-6-chlorothieno[2,3-d]pyrimidine, 2-(pyrazin-2-yl)-4-(3,4-ethylenedioxybenzylamino)-6-chlorothieno[2,3-d]pyrimidine;
with 4-chloro-2-(pyrazin-2-yl)-5-chloro-6-methylthieno[2,3-d]pyrimidine, 2-(pyrazin-2-yl)-4-(3,4-ethylenedioxybenzylamino)-5-chloro-6-methylthieno[2,3-d]pyrimidine;
with 4-chloro-2-(pyrazin-2-yl)-6-nitrothieno[2,3-d]pyrimidine, 2-(pyrazin-2-yl)-4-(3,4-ethylenedioxybenzylamino)-6-nitrothieno[2,3-d]pyrimidine;

with 4-chloro-2-(pyrazin-2-yl)-5,6-dimethylthieno[2,3-d]pyrimidine, 2-(pyrazin-2-yl)-4-(3,4-ethylenedioxybenzylamino)-5,6-dimethylthieno[2,3-d]pyrimidine;

with 4-chloro-2-(pyrazin-2-yl)-6-trifluoromethylthieno[2,3-d]pyrimidine, 2-(pyrazin-2-yl)-4-(3,4-ethylenedioxybenzylamino)-6-trifluoromethylthieno[2,3-d]pyrimidine;

with 4-chloro-2-(pyridin-2-yl)-6-methylthieno[2,3-d]pyrimidine, 2-(pyridin-2-yl)-4-(3,4-ethylenedioxybenzylamino)-6-methylthieno[2,3-d]pyrimidine;

with 4-chloro-2-(pyridin-2-yl)-5-methylthieno[2,3-d]pyrimidine, 2-(pyridin-2-yl)-4-(3,4-ethylenedioxybenzylamino)-5-methylthieno[2,3-d]pyrimidine;

with 4-chloro-2-(pyridin-2-yl)-5,6,7,8-tetrahydro[1]benzothieno[2,3-d]pyrimidine, 2-(pyridin-2-yl)-4-(3,4-ethylenedioxybenzylamino)-5,6,7,8-tetrahydro[1]benzothieno[2,3-d]pyrimidine;

with 4-chloro-2-(pyridin-2-yl)-5,6-cyclopentenothieno[2,3-d]pyrimidine, 2-(pyridin-2-yl)-4-(3,4-ethylenedioxybenzylamino)-5,6-cyclopentenothieno[2,3-d]pyrimidine;

with 4-chloro-2-(pyridin-2-yl)-5,6-cycloheptenothieno[2,3-d]pyrimidine, 2-(pyridin-2-yl)-4-(3,4-ethylenedioxybenzylamino)-5,6-cycloheptenothieno[2,3-d]pyrimidine;

with 4-chloro-2-(pyridin-2-yl)-6-ethylthieno[2,3-d]pyrimidine, 2-(pyridin-2-yl)-4-(3,4-ethylenedioxybenzylamino)-6-ethylthieno[2,3-d]pyrimidine;

with 4-chloro-2-(pyridin-2-yl)-6-chlorothieno[2,3-d]pyrimidine, 2-(pyridin-2-yl)-4-(3,4-ethylenedioxybenzylamino)-6-chlorothieno[2,3-d]pyrimidine;

with 4-chloro-2-(pyridin-2-yl)-5-chloro-6-methylthieno[2,3-d]pyrimidine, 2-(pyridin-2-yl)-4-(3,4-ethylenedioxybenzylamino)-5-chloro-6-methylthieno[2,3-d]pyrimidine;

with 4-chloro-2-(pyridin-2-yl)-6-nitrothieno[2,3-d]pyrimidine, 2-(pyridin-2-yl)-4-(3,4-ethylenedioxybenzylamino)-6-nitrothieno[2,3-d]pyrimidine;

with 4-chloro-2-(pyridin-2-yl)-5,6-dimethylthieno[2,3-d]pyrimidine, 2-(pyridin-2-yl)-4-(3,4-ethylenedioxybenzylamino)-5,6-dimethylthieno[2,3-d]pyrimidine;

with 4-chloro-2-(pyridin-2-yl)-6-trifluoromethylthieno[2,3-d]pyrimidine, 2-(pyridin-2-yl)-4-(3,4-ethylenedioxybenzylamino)-6-trifluoromethylthieno[2,3-d]pyrimidine;

with 4-chloro-2-(pyridin-4-yl)-6-methylthieno[2,3-d]pyrimidine, 2-(pyridin-4-yl)-4-(3,4-ethylenedioxybenzylamino)-6-methylthieno[2,3-d]pyrimidine;

with 4-chloro-2-(pyridin-4-yl)-5-methylthieno[2,3-d]pyrimidine, 2-(pyridin-4-yl)-4-(3,4-ethylenedioxybenzylamino)-5-methylthieno[2,3-d]pyrimidine;

with 4-chloro-2-(pyridin-4-yl)-5,6,7,8-tetrahydro[1]benzothieno[2,3-d]pyrimidine, 2-(pyridin-4-yl)-4-(3,4-ethylenedioxybenzylamino)-5,6,7,8-tetrahydro[1]benzothieno[2,3-d]pyrimidine;

with 4-chloro-2-(pyridin-4-yl)-5,6-cyclopentenothieno[2,3-d]pyrimidine, 2-(pyridin-4-yl)-4-(3,4-ethylenedioxybenzylamino)-5,6-cyclopentenothieno[2,3-d]pyrimidine;

with 4-chloro-2-(pyridin-4-yl)-5,6-cycloheptenothieno[2,3-d]pyrimidine, 2-(pyridin-4-yl)-4-(3,4-ethylenedioxybenzylamino)-5,6-cycloheptenothieno[2,3-d]pyrimidine;

with 4-chloro-2-(pyridin-4-yl)-6-ethylthieno[2,3-d]pyrimidine, 2-(pyridin-4-yl)-4-(3,4-ethylenedioxybenzylamino)-6-ethylthieno[2,3-d]pyrimidine;

with 4-chloro-2-(pyridin-4-yl)-6-chlorothieno[2,3-d]pyrimidine, 2-(pyridin-4-yl)-4-(3,4-ethylenedioxybenzylamino)-6-chlorothieno[2,3-d]pyrimidine;

with 4-chloro-2-(pyridin-4-yl)-5-chloro-6-methylthieno[2,3-d]pyrimidine, 2-(pyridin-4-yl)-4-(3,4-ethylenedioxybenzylamino)-5-chloro-6-methylthieno[2,3-d]pyrimidine;

with 4-chloro-2-(pyridin-4-yl)-6-nitrothieno[2,3-d]pyrimidine, 2-(pyridin-4-yl)-4-(3,4-ethylenedioxybenzylamino)-6-nitrothieno[2,3-d]pyrimidine;

with 4-chloro-2-(pyridin-4-yl)-5,6-dimethylthieno[2,3-d]pyrimidine, 2-(pyridin-4-yl)-4-(3,4-ethylenedioxybenzylamino)-5,6-dimethylthieno[2,3-d]pyrimidine;

with 4-chloro-2-(pyridin-4-yl)-6-trifluoromethylthieno[2,3-d]pyrimidine, 2-(pyridin-4-yl)-4-(3,4-ethylenedioxybenzylamino)-6-trifluoromethylthieno[2,3-d]pyrimidine.

The following are obtained analogously by reaction of phenethylamine:

with 4-chloro-2-(pyridin-3-yl)-6-methylthieno[2,3-d]pyrimidine, 2-(pyridin-3-yl)-4-phenethylamino-6-methylthieno[2,3-d]pyrimidine;

with 4-chloro-2-(pyridin-3-yl)-5-methylthieno[2,3-d]pyrimidine, 2-(pyridin-3-yl)-4-phenethylamino-5-methylthieno[2,3-d]pyrimidine;

with 4-chloro-2-(pyridin-3-yl)-5,6,7,8-tetrahydro[1]benzothieno[2,3-d]pyrimidine, 2-(pyridin-3-yl)-4-phenethylamino-5,6,7,8-tetrahydro[1]benzothieno[2,3-d]pyrimidine;

with 4-chloro-2-(pyridin-3-yl)-5,6-cyclopentenothieno[2,3-d]pyrimidine, 2-(pyridin-3-yl)-4-phenethylamino-5,6-cyclopentenothieno[2,3-d]pyrimidine;

with 4-chloro-2-(pyridin-3-yl)-5,6-cycloheptenothieno[2,3-d]pyrimidine, 2-(pyridin-3-yl)-4-phenethylamino-5,6-cycloheptenothieno[2,3-d]pyrimidine;

with 4-chloro-2-(pyridin-3-yl)-6-ethylthieno[2,3-d]pyrimidine, 2-(pyridin-3-yl)-4-phenethylamino-6-ethylthieno[2,3-d]pyrimidine;

with 4-chloro-2-(pyridin-3-yl)-6-chlorothieno[2,3-d]pyrimidine, 2-(pyridin-3-yl)-4-phenethylamino-6-chlorothieno[2,3-d]pyrimidine;

with 4-chloro-2-(pyridin-3-yl)-5-chloro-6-methylthieno[2,3-d]pyrimidine, 2-(pyridin-3-yl)-4-phenethylamino-5-chloro-6-methylthieno[2,3-d]pyrimidine;

with 4-chloro-2-(pyridin-3-yl)-6-nitrothieno[2,3-d]pyrimidine, 2-(pyridin-3-yl)-4-phenethylamino-6-nitrothieno[2,3-d]pyrimidine;

with 4-chloro-2-(pyridin-3-yl)-5,6-dimethylthieno[2,3-d]pyrimidine, 2-(pyridin-3-yl)-4-phenethylamino-5,6-dimethylthieno[2,3-d]pyrimidine;

with 4-chloro-2-(pyridin-3-yl)-6-trifluoromethylthieno[2,3-d]pyrimidine, 2-(pyridin-3-yl)-4-phenethylamino-6-trifluoromethylthieno[2,3-d]pyrimidine;

with 4-chloro-2-(isoxazol-5-yl)-6-methylthieno[2,3-d]pyrimidine, 2-(isoxazol-5-yl)-4-phenethylamino-6-methylthieno[2,3-d]pyrimidine;

with 4-chloro-2-(isoxazol-5-yl)-5-methylthieno[2,3-d]pyrimidine, 2-(isoxazol-5-yl)-4-phenethylamino-5-methylthieno[2,3-d]pyrimidine;

with 4-chloro-2-(isoxazol-5-yl)-5,6,7,8-tetrahydro[1]benzothieno[2,3-d]pyrimidine, 2-(isoxazol-5-yl)-4-phenethylamino)-5,6,7,8-tetrahydro[1]benzothieno[2,3-d]pyrimidine;

with 4-chloro-2-(isoxazol-5-yl)-5,6-cyclopentenothieno[2,3-d]pyrimidine, 2-(isoxazol-5-yl)-4-phenethylamino-5,6-cyclopentenothieno[2,3-d]pyrimidine;

with 4-chloro-2-(isoxazol-5-yl)-5,6-cycloheptenothieno[2,3-d]pyrimidine, 2-(isoxazol-5-yl)-4-phenethylamino-5,6-cycloheptenothieno[2,3-d]pyrimidine;

with 4-chloro-2-(isoxazol-5-yl)-6-ethylthieno[2,3-d]pyrimidine, 2-(isoxazol-5-yl)-4-phenethylamino-6-ethylthieno[2,3-d]pyrimidine;

with 4-chloro-2-(isoxazol-5-yl)-6-chlorothieno[2,3-d]pyrimidine, 2-(isoxazol-5-yl)-4-phenethylamino-6-chlorothieno[2,3-d]pyrimidine;

with 4-chloro-2-(isoxazol-5-yl)-5-chloro-6-methylthieno[2,3-d]pyrimidine, 2-(isoxazol-5-yl)-4-phenethylamino-5-chloro-6-methylthieno[2,3-d]pyrimidine;

with 4-chloro-2-(isoxazol-5-yl)-6-nitrothieno[2,3-d]pyrimidine, 2-(isoxazol-5-yl)-4-phenethylamino-6-nitrothieno[2,3-d]pyrimidine;

with 4-chloro-2-(isoxazol-5-yl)-5,6-dimethylthieno[2,3-d]pyrimidine, 2-(isoxazol-5-yl)-4-phenethylamino-5,6-dimethylthieno[2,3-d]pyrimidine;

with 4-chloro-2-(isoxazol-5-yl)-6-trifluoromethylthieno[2,3-d]pyrimidine, 2-(isoxazol-5-yl)-4-phenethylamino-6-trifluoromethylthieno[2,3-d]pyrimidine;

with 4-chloro-2-(pyrazin-2-yl)-6-methylthieno[2,3-d]pyrimidine, 2-(pyrazin-2-yl)-4-phenethylamino-6-methylthieno[2,3-d]pyrimidine;

with 4-chloro-2-(pyrazin-2-yl)-5-methylthieno[2,3-d]pyrimidine, 2-(pyrazin-2-yl)-4-phenethylamino-5-methylthieno[2,3-d]pyrimidine;

with 4-chloro-2-(pyrazin-2-yl)-5,6,7,8-tetrahydro[1]benzothieno[2,3-d]pyrimidine, 2-(pyrazin-2-yl)-4-phenethylamino)-5,6,7,8-tetrahydro[1]benzothieno[2,3-d]pyrimidine;

with 4-chloro-2-(pyrazin-2-yl)-5,6-cyclopentenothieno[2,3-d]pyrimidine, 2-(pyrazin-2-yl)-4-phenethylamino-5,6-cyclopentenothieno[2,3-d]pyrimidine;

with 4-chloro-2-(pyrazin-2-yl)-5,6-cycloheptenothieno[2,3-d]pyrimidine, 2-(pyrazin-2-yl)-4-phenethylamino-5,6-cycloheptenothieno[2,3-d]pyrimidine;

with 4-chloro-2-(pyrazin-2-yl)-6-ethylthieno[2,3-d]pyrimidine, 2-(pyrazin-2-yl)-4-phenethylamino-6-ethylthieno[2,3-d]pyrimidine;

with 4-chloro-2-(pyrazin-2-yl)-6-chlorothieno[2,3-d]pyrimidine, 2-(pyrazin-2-yl)-4-phenethylamino-6-chlorothieno[2,3-d]pyrimidine;

with 4-chloro-2-(pyrazin-2-yl)-5-chloro-6-methylthieno[2,3-d]pyrimidine, 2-(pyrazin-2-yl)-4-phenethylamino-5-chloro-6-methylthieno[2,3-d]pyrimidine;

with 4-chloro-2-(pyrazin-2-yl)-6-nitrothieno[2,3-d]pyrimidine, 2-(pyrazin-2-yl)-4-phenethylamino-6-nitrothieno[2,3-d]pyrimidine;

with 4-chloro-2-(pyrazin-2-yl)-5,6-dimethylthieno[2,3-d]pyrimidine, 2-(pyrazin-2-yl)-4-phenethylamino-5,6-dimethylthieno[2,3-d]pyrimidine;

with 4-chloro-2-(pyrazin-2-yl)-6-trifluoromethylthieno[2,3-d]pyrimidine, 2-(pyrazin-2-yl)-4-phenethylamino-6-trifluoromethylthieno[2,3-d]pyrimidine;

with 4-chloro-2-(pyridin-2-yl)-6-methylthieno[2,3-d]pyrimidine, 2-(pyridin-2-yl)-4-phenethylamino-6-methylthieno[2,3-d]pyrimidine;

with 4-chloro-2-(pyridin-2-yl)-5-methylthieno[2,3-d]pyrimidine, 2-(pyridin-2-yl)-4-phenethylamino-5-methylthieno[2,3-d]pyrimidine;

with 4-chloro-2-(pyridin-2-yl)-5,6,7,8-tetrahydro[1]benzothieno[2,3-d]pyrimidine, 2-(pyridin-2-yl)-4-phenethylamino-5,6,7,8-tetrahydro[1]benzothieno[2,3-d]pyrimidine;

with 4-chloro-2-(pyridin-2-yl)-5,6-cyclopentenothieno[2,3-d]pyrimidine, 2-(pyridin-2-yl)-4-phenethylamino-5,6-cyclopentenothieno[2,3-d]pyrimidine;

with 4-chloro-2-(pyridin-2-yl)-5,6-cycloheptenothieno[2,3-d]pyrimidine, 2-(pyridin-2-yl)-4-phenethylamino-5,6-cycloheptenothieno[2,3-d]pyrimidine;

with 4-chloro-2-(pyridin-2-yl)-6-ethylthieno[2,3-d]pyrimidine, 2-(pyridin-2-yl)-4-phenethylamino)-6-ethylthieno[2,3-d]pyrimidine;

with 4-chloro-2-(pyridin-2-yl)-6-chlorothieno[2,3-d]pyrimidine, 2-(pyridin-2-yl)-4-phenethylamino-6-chlorothieno[2,3-d]pyrimidine;

with 4-chloro-2-(pyridin-2-yl)-5-chloro-6-methylthieno[2,3-d]pyrimidine, 2-(pyridin-2-yl)-4-phenethylamino-5-chloro-6-methylthieno[2,3-d]pyrimidine;

with 4-chloro-2-(pyridin-2-yl)-6-nitrothieno[2,3-d]pyrimidine, 2-(pyridin-2-yl)-4-phenethylamino-6-nitrothieno[2,3-d]pyrimidine;

with 4-chloro-2-(pyridin-2-yl)-5,6-dimethylthieno[2,3-d]pyrimidine, 2-(pyridin-2-yl)-4-phenethylamino-5,6-dimethylthieno[2,3-d]pyrimidine;

with 4-chloro-2-(pyridin-2-yl)-6-trifluoromethylthieno[2,3-d]pyrimidine, 2-(pyridin-2-yl)-4-phenethylamino-6-trifluoromethylthieno[2,3-d]pyrimidine;

with 4-chloro-2-(pyridin-4-yl)-6-methylthieno[2,3-d]pyrimidine, 2-(pyridin-4-yl)-4-phenethylamino-6-methylthieno[2,3-d]pyrimidine;

with 4-chloro-2-(pyridin-4-yl)-5-methylthieno[2,3-d]pyrimidine, 2-(pyridin-4-yl)-4-phenethylamino-5-methylthieno[2,3-d]pyrimidine;

with 4-chloro-2-(pyridin-4-yl)-5,6,7,8-tetrahydro[1]benzothieno[2,3-d]pyrimidine, 2-(pyridin-4-yl)-4-phenethylamino-5,6,7,8-tetrahydro[1]benzothieno[2,3-d]pyrimidine;

with 4-chloro-2-(pyridin-4-yl)-5,6-cyclopentenothieno[2,3-d]pyrimidine, 2-(pyridin-4-yl)-4-phenethylamino-5,6-cyclopentenothieno[2,3-d]pyrimidine;

with 4-chloro-2-(pyridin-4-yl)-5,6-cycloheptenothieno[2,3-d]pyrimidine, 2-(pyridin-4-yl)-4-phenethylamino-5,6-cycloheptenothieno[2,3-d]pyrimidine;

with 4-chloro-2-(pyridin-4-yl)-6-ethylthieno[2,3-d]pyrimidine, 2-(pyridin-4-yl)-4-phenethylamino-6-ethylthieno[2,3-d]pyrimidine;

with 4-chloro-2-(pyridin-4-yl)-6-chlorothieno[2,3-d]pyrimidine, 2-(pyridin-4-yl)-4-phenethylamino-6-chlorothieno[2,3-d]pyrimidine;

with 4-chloro-2-(pyridin-4-yl)-5-chloro-6-methylthieno[2,3-d]pyrimidine, 2-(pyridin-4-yl)-4-phenethylamino-5-chloro-6-methylthieno[2,3-d]pyrimidine;

with 4-chloro-2-(pyridin-4-yl)-6-nitrothieno[2,3-d]pyrimidine, 2-(pyridin-4-yl)-4-phenethylamino-6-nitrothieno[2,3-d]pyrimidine;

with 4-chloro-2-(pyridin-4-yl)-5,6-dimethylthieno[2,3-d]pyrimidine, 2-(pyridin-4-yl)-4-phenethylamino-5,6-dimethylthieno[2,3-d]pyrimidine;

with 4-chloro-2-(pyridin-4-yl)-6-trifluoromethylthieno[2,3-d]pyrimidine, 2-(pyridin-4-yl)-4-phenethylamino-6-trifluoromethylthieno[2,3-d]pyrimidine;

EXAMPLE 5

A solution of 2-(imidazol-1-yl)-6-methyl-4-(3-nitrobenzylamino)thieno[2,3-d]pyrimidine in methanol is hydrogenated in the presence of Raney nickel. The catalyst is filtered off and the solution is concentrated. After recrystallization, 2-(imidazol-1-yl)-6-methyl-4-(3-aminobenzylamino)thieno[2,3-d]pyrimidine is obtained.

EXAMPLE 6

A solution of 6 g of 2-(imidazol-1-yl)-6-methyl-4-(3-aminobenzylamino)thieno[2,3-d]pyrimidine and 0.5 g of titanium tetrachloride in 100 ml of methanol is treated with 1 ml of freshly distilled acetaldehyde. Then, 4 g of sodium cyanoborohydride are added, and the mixture is stirred for 30 hours. Half-concentrated hydrochloric acid is added, the mixture is worked up as customary, and 2-(imidazol-1-yl)-6-methyl-4-(3-N-ethylaminobenzylamino)thieno[2,3-d]pyrimidine is obtained.

EXAMPLE 7

The following are obtained analogously to Example 2

2-(imidazol-1-yl)-5,6,7,8-tetrahydro-4-(3,4-difluorbenzylamino)[1]benzothieno[2,3-d]pyrimidine, m.p. 212°;

2-(imidazol-1-yl)-5,6-cyclopenteno-4-benzylaminothieno[2,3-d]pyrimidine, m.p. 221°;

2-(imidazol-1-yl)-6-methyl-4-benzylaminothieno[2,3-d]pyrimidine, m.p. 241°;

2-(imidazol-1-yl)-6-methyl-4-(3,4-dimethoxybenzylamino)thieno[2,3-d]pyrimidine, m.p. 217°;

2-(imidazol-1-yl)-6-chloro-5-methyl-4-(3,4-methylenedioxybenzylamino)thieno[2,3-d]pyrimidine, m.p. 250°;

2-(imidazol-1-yl)-5,6,7,8-tetrahydro-4-benzylamino-[1]benzothieno[2,3-d]pyrimidine, m.p. 190°;

2-(1,2,4-triazole-1-yl)-6-methyl-4-(3,4-methylenedioxybenzylamino)thieno[2,3-d]pyrimidine, m.p. 231°;

2-(imidazol-1-yl)-6-isopropyl-4-(3,4-methylenedioxybenzylamino)thieno[2,3-d]pyrimidine, m.p. 192°;

2-(imidazol-1-yl)-6-propyl-4-(3,4-methylenedioxybenzylamino)thieno[2,3-d]pyrimidine, m.p. 183°.

The examples which follow relate to pharmaceutical products:

Example A

Vials 100 g of an active ingredient of the formula I and 5 g of disodium hydrogen phosphate in 3 l of twice-distilled water is brought to pH 6.5 with 2N hydrochloric acid, filter sterilized, filled into vials, lyophilized under sterile conditions and sealed in sterile form. Each vial comprises 5 mg of active ingredient.

Example B

Suppositories

A mixture of 20 g of an active ingredient of the formula I is melted with 100 g of soya lecithin and 1400 g of cocoa butter, and the mixture is poured into moulds and left to cool. Each suppository comprises 20 mg of active ingredient.

Example C

Solution

A solution is prepared from 1 g of an active ingredient of the formula I, 9.38 g of NaH$_2$PO$_4$.2H$_2$O, 28.48 g of Na$_2$HPO$_4$.12H$_2$O and 0.1 g of benzalkonium chloride in 940 ml of twice-distilled water. The solution is brought to pH 6.8, made up to 1 l and sterilized by irradiation. This solution can be used in the form of eye drops.

Example D

Ointment 500 mg of an active ingredient of the formula I are mixed with 99.5 g of petroleum jelly under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is tabletted in the customary manner in such a way that each tablet comprises 10 mg of active ingredient.

Example F

Sugar-coated Tablets

A mixture is tabletted analogously to Example E and the tablets are subsequently coated in the customary manner with a coating of sucrose, potato starch, talc, tragacanth and colouring.

Example G

Capsules 2 kg of active ingredient of the formula I are filled into hard-gelatin capsules in the customary manner so that each capsule comprises 20 mg of the active ingredient.

Example H

Ampoules

A solution of 1 kg of active ingredient of the formula I in 60 l of twice-distilled water is filter sterilized, filled into ampoules, lyophilized under sterile conditions and sealed in sterile form. Each ampoule comprises 10 mg of active ingredient.

Example I

Spray for Inhalation 14 g of active ingredient of the formula I are dissolved in 10 l of isotonic NaCl solution and the solution is filled into commercially available pump-operated spray containers. The solution can be sprayed into the mouth or nose. One actuation (approximately 0.1 ml) corresponds to a dose of approximately 0.14 mg.

What is claimed is:

1. Compounds of the formula I

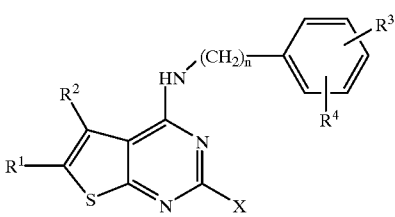

in which

R$^1$, R$^2$ in each case independently of one another are H, A, or Hal, where one of the radicals R$^1$ or R$^2$ is always ≠H;

R$^1$ and R$^2$ together are also alkylene having 3–5 C atoms;

R$^3$, R$^4$ in each case independently of one another are H, OA, or Hal;

R$^3$ and R$^4$ together are also —O—CH$_2$—O— or —O—CH$_2$—CH$_2$—O—;

A is an alkyl having 1 to 6 C atoms;

X is 1-imidazolyl, 2-methyl-imidazolyl, pyrazolyl, 1,2,4-triazolyl-1-yl or 3-pyridyl;

Hal is F, Cl, Br, or I and n is 1;

and the physiologically acceptable salts thereof.

2. Compounds of the formula I according to claim 1 wherein compounds of the formula I are:

(a) 2-(1-imidazolyl)-6-methyl-4-(3,4-methylenedioxy-benzylamino)thieno[2,3-d]pyrimidine;

(b) 2-(1-imidazolyl)-5,6-dimethyl-4-(3,4-methylene-dioxybenzylamino)thieno[2,3-d]pyrimidine;

(c) 2-(1-imidazolyl)-4-(3,4-methylenedioxybenzyl-amino)-5,6,7,8-tetrahydro[1]benzothieno[2,3-d]-pyrimidine;

(d) 2-(1-imidazolyl)-5-chloro-4-(3,4-methylenedioxy-benzylamino)thieno[2,3-d]pyrimidine;

(e) 2-(1-imidazolyl)-6-chloro-4-(3,4-methylenedioxy-benzylamino)thieno[2,3-d]pyrimidine;

(f) 2-(1,2,4-triazol-1-yl)-4-(3,4-methylenedioxy-benzylamino)-5,6,7,8-tetrahydro[1]benzothieno-[2,3-d]pyrimidine;

(g) 2-(pyrazol-1-yl)-4-(3,4-methylenedioxybenzyl-amino)-5,6,7,8-tetrahydro[1]benzothieno[2,3-d]pyrimidine; or (h) 2-(Pyridin-3-yl)-4-(3,4-methylenedioxybenzyl-amino)-5,6,7,8-tetrahydro[1]benzothieno[2,3-d]pyrimidine.

3. A process for the preparation of compounds of the formula I according to claim 1 and salts thereof in which X is bonded via N, comprising reacting:

a) compound of the formula II

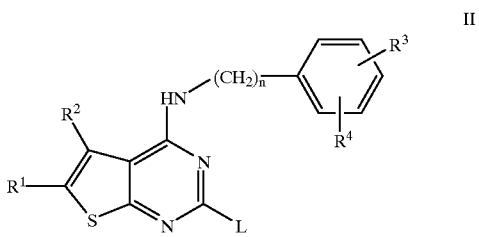

II in which $R^1$, $R^2$, $R^3$, $R^4$ and n have the abovementioned meanings and L, is Cl, Br, OH, $SCH_3$ or a reactive esterified OH group with an unsaturated 5–7-membered heterocycle which has at least one NH group and which is unsubstituted or mono-, di- or tri-substituted by A, Hal or $CF_3$ and in which additionally further $CH_2$ groups can be replaced by NH, NA, S or O, or b) reacting a compound of the formula III

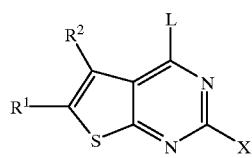

III in which $R^1$, $R^2$ and X has the abovementioned meanings, and L is Cl, Br, OH, $SCH_3$ or a reactive esterified OH group with a compound of the formula IV

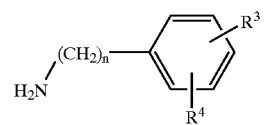

IV in which $R^3$, $R^4$ and n have the abovementioned meanings, or c) converting a compound of the formula I wherein a radical $R^1$, $R^2$, $R^3$ and/or $R^4$ into a different radical $R^1$, $R^2$, $R^3$ and/or $R^4$ by reducing a nitro group, by converting a primary or a secondary amino group into an alkylated amine by reductive amination or by acylating such an amino group, and/or converting a basic compound of the formula I into a salt thereof by treatment with an acid.

4. A process for the preparation of pharmaceutical products, comprising bringing a compound of the formula I according to claim 1 and/or a physiologically acceptable salt thereof into a suitable pharmaceutical form together with at least one solid, liquid or semi-liquid excipient or auxiliary.

5. A pharmaceutical preparation, comprising at least one compound of the formula I according to claim 1 and/or a physiologically acceptable salt thereof.

6. Compounds of the formula I according to claim 1 and the physiologically acceptable salts thereof for combating diseases of the cardiovascular system and for the therapy of impaired potency.

7. Pharmaceuticals of the formula I according to claim 1 and the physiologically acceptable salts thereof as phosphodiesterase V inhibitors.

8. The compounds of the formula I according to claim 1 wherein A is methyl, ethyl, propyl, isopropyl, butyl, isobutyl, sec-butyl, tert-butyl, n-pentyl, neopentyl, or iso-pentyl.

9. The compounds of the formula I according to claim 1 wherein the compound is 2-(imidazol-1-yl)-5,6,7,8-tetrahydro-4-(3,4-methylene-dioxybenzylamino)[1]benzothieno[2,3-d]pyrimidine.

10. The compounds of the formula I according to claim 1 wherein one of $R^1$ or $R^2$ is methyl, ethyl, propyl, or butyl and one of R or $R^2$ is H.

11. The compounds of the formula I according to claim 1 wherein $R^1$ or $R^2$ together are propylene, butylene, or pentylene.

12. The compounds of the formula I according to claim 1 wherein $R^3$ or $R^4$ is methoxy, ethoxy, or propoxy.

13. The compounds of the formula I according to claim 1 wherein X is imidazolyl or pyridinyl.

14. The compounds of the formula I according to claim 13 wherein $R^1$ or $R^2$ are a $C_{3-5}$ alkylene group.

15. The process of claim 3 where the reaction of the compound of formula II further comprises an acid-binding agent.

16. The process of claim 3 where the reaction of the compound of formula II further comprises an inert solvent.

17. The process according to claim 3 wherein the acid of the salt conversion treatment is an inorganic acid, a hydrohalic acid, a phosphorus acid, or an organic acid.

18. A method of treating a cardiovascular disease, an impaired potency, or a disease characterized by raised c GMP comprising administrating to a host a compound of claim 1.

19. A method of treating a cardiac insufficiency comprising administrating to a host a compound of claim 1.

* * * * *